United States Patent
Goldman et al.

(10) Patent No.: US 7,888,025 B2
(45) Date of Patent: Feb. 15, 2011

(54) INTESTINAL FOLATE TRANSPORTER METHOD

(75) Inventors: I. David Goldman, Pelham, NY (US); Andong Qiu, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 5 days.

(21) Appl. No.: 12/074,371

(22) Filed: Mar. 3, 2008

(65) Prior Publication Data

US 2008/0241947 A1 Oct. 2, 2008

Related U.S. Application Data

(60) Provisional application No. 60/904,954, filed on Mar. 5, 2007.

(51) Int. Cl.
*C12Q 1/68* (2006.01)

(52) U.S. Cl. .......................................................... 435/6

(58) Field of Classification Search ........................ None
See application file for complete search history.

(56) References Cited

PUBLICATIONS

Zhao, et al. "The relationship between folate transport activity at low pH and reduced folate carrier function in human Huh7 hepatoma cells" Biochim. Biophys. Acta. 1715(1): abstract only (2005).

Shayeghi, et al. "Identification of an Intestinal Heme Transporter" Cell 122:789-801 (2005).

Zhao, et al. "Antifolate Resistance in a HeLa Cell Line Associated With Impaired Transport Independent of the Reduced Folate Carrier" Clinical Cancer Research 10:8735-8742 (2004).

Zhao, et al. "A Prominent Low-pH Methotrexate Transport Activity in Human Solid Tumors: Contribution to the Preservation of Methotrexate Pharmacologic Activity in HeLa Cells Lacking the Reduced Folate Carrier" Clinical Cancer Research 10:718-727 (2004).

Wang, et al. "Characterization of a Folate Transporter in HeLa Cells with a Low pH Optimum and High Affinity for Pemetrexed Distinct from the Reduced Folate Carrier" Clinical Cancer Research 10:6256-6264 (2004).

Qiu, et al. "Identification of an Intestinal Folate Transporter and the Molecular Basis for Hereditary Folate Malabsorption" Cell 127:917-928 (2006).

*Primary Examiner*—Michael Pak
(74) *Attorney, Agent, or Firm*—Amster, Rothstein & Ebenstein LLP

(57) ABSTRACT

Provided is an isolated and purified DNA molecule comprising the coding region of a PCFT cDNA. Also provided is a segment of the above DNA molecule, capable of serving as a primer for amplifying at least a portion of the DNA molecule. Additionally provided is a pair of the above segments that can be used together as forward and reverse PCR primers for amplifying at least a portion of the above DNA molecule. Further provided is an isolated and purified human PCFT protein. Also provided is a method of evaluating the ability of a human to undergo intestinal folate absorption.

25 Claims, 12 Drawing Sheets

A

B

- pH 5.5
- pH 6.5

INTESTINAL FOLATE TRANSPORTER METHOD

CROSS REFERENCE TO RELATED APPLICATION

This application is a U.S. Utility Application claiming the benefit of U.S. Provisional Application No. 60/904,954, filed Mar. 5, 2007, the content of which is hereby incorporated by reference in its entirety.

STATEMENT REGARDING FEDERALLY SPONSORED RESEARCH OR DEVELOPMENT

This invention is supported in part by NIH Grant No. 5R01 CA082621-08. As such, the U.S. Government has certain rights in the invention.

BACKGROUND OF THE INVENTION (1) Field of the Invention

The present invention generally relates to genetic causes of disease. More specifically, the invention provides compositions and methods relating to a newly identified intestinal folate transporter and the cause of hereditary folate malabsorption.

(2) Description of the Related Art

Folates are essential cofactors required for the provision of one-carbon moieties in key biosynthetic and epigenetic processes (Stover, 2004). Folate deficiency is prevalent in underdeveloped countries and, even in the western world, subtle deficiency is a public health problem most notable in its association with neural tube defects in the developing embryo (Eichholzer et al., 2006). Mammals cannot synthesize folates; hence, dietary sources must meet metabolic needs necessitating an efficient intestinal absorptive mechanism. Absorption of folates occurs primarily in the duodenum and upper jejunum and involves a carrier-mediated process with a low-pH optimum that operates efficiently within the acidic microclimate of the intestinal surface in this region (Selhub and Rosenberg, 1981; Mason and Rosenberg, 1994; McEwan et al., 1990). The specificity and other properties of this process have been well established and similar folate transport activities with a low-pH optimum have been identified in other normal tissues and in human solid tumor cell lines (Horne, 1993; Zhao et al., 2004). Despite the prevalence and importance of this process, a folate transport protein with a low-pH optimum has not been identified.

There are two known, highly specific, mammalian folate transporters. Their properties were the subject of a recent review (Matherly and Goldman, 2003). The reduced folate carrier (SLC19A1) is a facilitative transporter with the characteristics of an anion exchanger. There are two GPI-linked folate receptors, high-affinity binding proteins that mediate cellular uptake by an endocytic mechanism. Folate receptor expression in small intestine is negligible. While the reduced folate carrier is expressed on the brush border membrane of intestinal cells, this transporter has a neutral pH optimum and a specificity profile that differs substantially from that observed in intestinal folate absorption and transport into intestinal cells and cells of other tissue origin at low pH (Selhub and Rosenberg, 1981; Mason and Rosenberg, 1994; Wang et al., 2004). Further, when reduced folate carrier function is lost due to deletion, mutation, or loss of expression of the gene, the low-pH folate transport activity remains intact (Zhao et al., 2004; Zhao et al., 2005b; Wang et al., 2005).

Hereditary folate malabsorption (HFM) (OMIM 229050) is a rare autosomal recessive disorder caused by impaired intestinal folate absorption with folate deficiency characterized by anemia, hypoimmunoglobulinemia with recurrent infections, such as *Pneumocystis carinii* pneumonitis, and recurrent or chronic diarrhea. In many patients, neurological abnormalities such as seizures or mental retardation emerge at some point in early childhood and have been attributed to impaired transport of folates into the central nervous system (Geller et al., 2002). When this disorder is diagnosed early, signs and symptoms of HFM can be obviated by parental administration of folates or with higher doses of folates by the oral route (Geller et al., 2002; Poncz and Cohen, 1996). If untreated, the disease is fatal and, if treatment is delayed, the neurological deficits can become permanent (Corbeel et al., 1985; Jebnoun et al., 2001). Hence, it is important that physicians are aware of this disorder and establish a diagnosis and institute treatment as early as possible in infancy. The clinical characteristics of HFM and its treatment were the subject of a recent comprehensive review (Geller et al., 2002).

Based on the above, it would be desirable to identify the molecular basis for HFM. The present invention addresses that need.

SUMMARY OF THE INVENTION

Accordingly, the inventors have identified the gene and protein responsible for intestinal folate absorption, and have identified several mutations in that gene causing hereditary folate malabsorption.

Thus, the invention is directed to isolated and purified DNA molecules comprising a sequence at least 95% identical to SEQ ID NO:31.

The invention is also directed to segments of a DNA molecule having a sequence at least 95% identical to SEQ ID NO:1. These segments are capable of serving as a primer for amplifying at least a portion of the DNA molecule.

The invention is further directed to segments of a DNA molecule having a sequence at least 95% identical to SEQ ID NO:6. These segments are also capable of serving as a primer for amplifying at least a portion of the DNA molecule.

Additionally, the invention is directed to pairs of the above segments, where the pair can be used together as forward and reverse PCR primers for amplifying at least a portion of the DNA molecule.

The invention is further directed to isolated and purified human proton-coupled folate transporter (PCFT) proteins comprising an amino acid sequence at least 95% identical to SEQ ID NO:4.

The invention is additionally directed to methods of evaluating the ability of a human to undergo intestinal folate absorption. The methods comprise determining whether the human expresses an active PCFT having an amino acid sequence at least 90% homologous to SEQ ID NO:2, where the human is undergoing intestinal folate absorption if the human expresses the active PCFT.

MTX or [³H]folic acid (2 µM) uptake was assayed at pH 5.5 over 30 min. Panel C shows the initial uptake of [³H]MTX or [³H]folic acid (0.5 µM), at pH 5.5 and 37° C., into HepG2 cells stably transfected with pcDNA3.1(+) (Mock-HepG2) or pcDNA3.1(+)G21 (G21-HepG2). Panel D shows the initial uptake of [³H]MTX or [³H]folic acid (0.5 µM), at pH 5.5 and 37° C., into HeLa cells transiently transfected with pcDNA3.1(+) (Mock-HeLa) or pcDNA3.1(+)G21 (G21-HeLa). The data in panels B-D are the mean±SEM from three independent experiments. Panel E shows the detection of G21 protein expressed in *Xenopus oocytes* and HepG2 cells by SDS-PAGE and western blotting. Lane 1: water-injected oocytes, Lane 2: G21-cRNA injected oocytes, Lane 3: Mock-transfected HepG2 cells, Lane 4: G21-transfected HepG2 cells. The blot is representative of three independent experiments. Panel F shows the plasma membrane localization of G21 protein in HeLa cells transiently transfected with G21 cDNA detected by immunofluorescence. The bright fluorescence in the center and around the edges of the cell localizes the G21 protein, and duller fluorescence indicates the counterstaining by propidium iodide. The image shown is representative of three independent studies.

Figure 2:
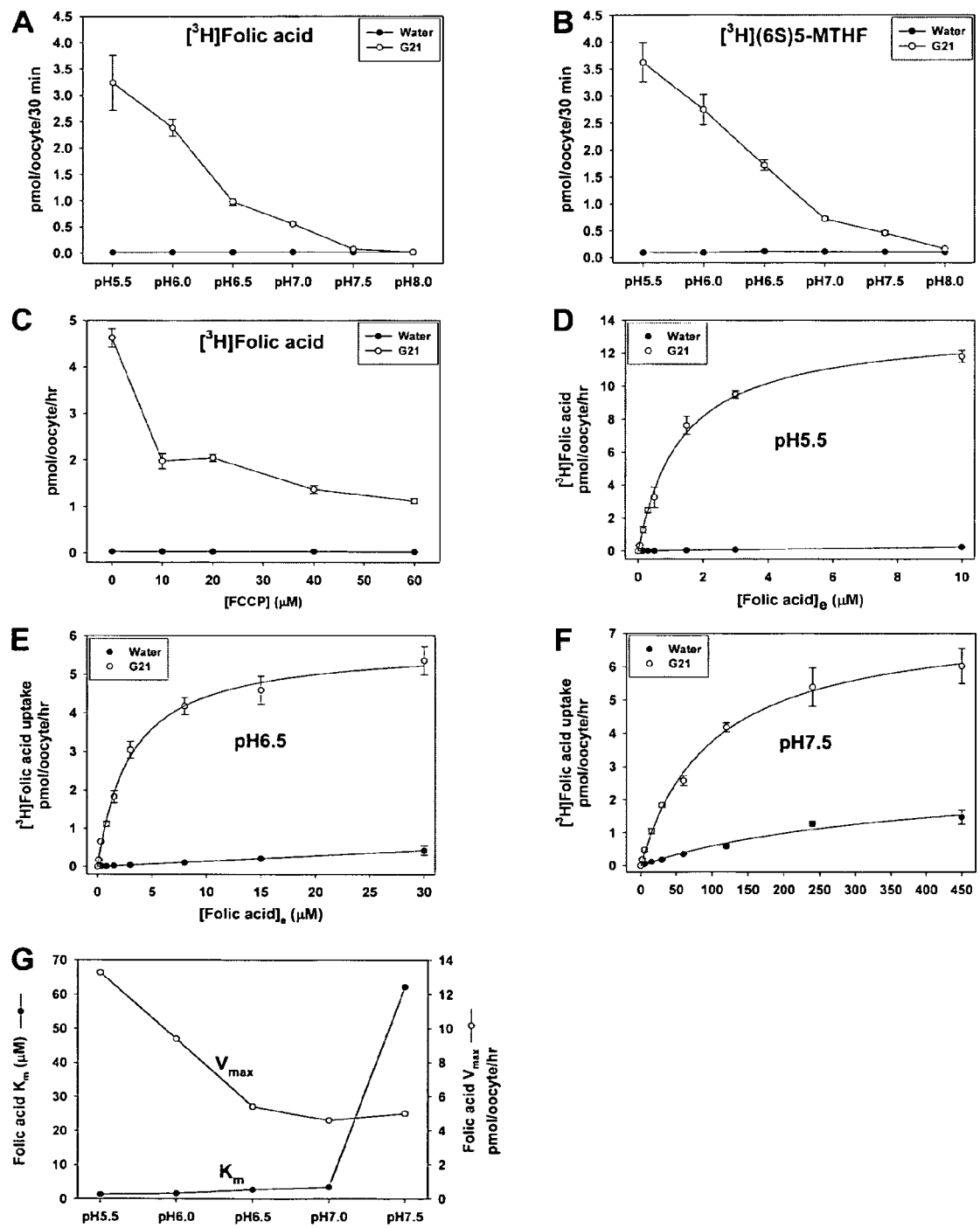

FIG. 2 is graphs showing pH dependence and kinetics of G21-mediated uptake of tritiated folates in *Xenopus oocytes*. Panels A-B show the uptake of 2 µM [³H]folic acid (Panel A) and [³H](6S)5-MTHF (Panel B) in water- and G21 cRNA-injected oocytes over 30 min. Panel C shows results when water- and G21 cRNA-injected oocytes were pre-incubated at pH 5.5 with a series of FCCP concentrations for 20 min. Uptake of [³H]folic acid (2 µM) was subsequently assessed at pH 5.5 over 1 hour. Panels A to C are representative of three independent studies. Panels D-F show the uptake of [³H]folic acid over 60 min at pH 5.5 (Panel D), 6.5 (Panel E) and 7.5 (Panel F) as a function of the extracellular folic acid concentration, [Folic acid]$_e$. The lines were generated, and kinetic constants calculated, based upon Michaelis-Menten kinetics, ($V=V_{max}[S]/(K_m+[S])$). The data is representative of 2 to 4 experiments as summarized in Table 1. Panel G shows the effects of extracellular pH on [³H]folic acid uptake $K_m$ and $V_{max}$. All measurements were made in a single batch of oocytes with the injection of the same amount of G21 cRNA.

Figure 3:
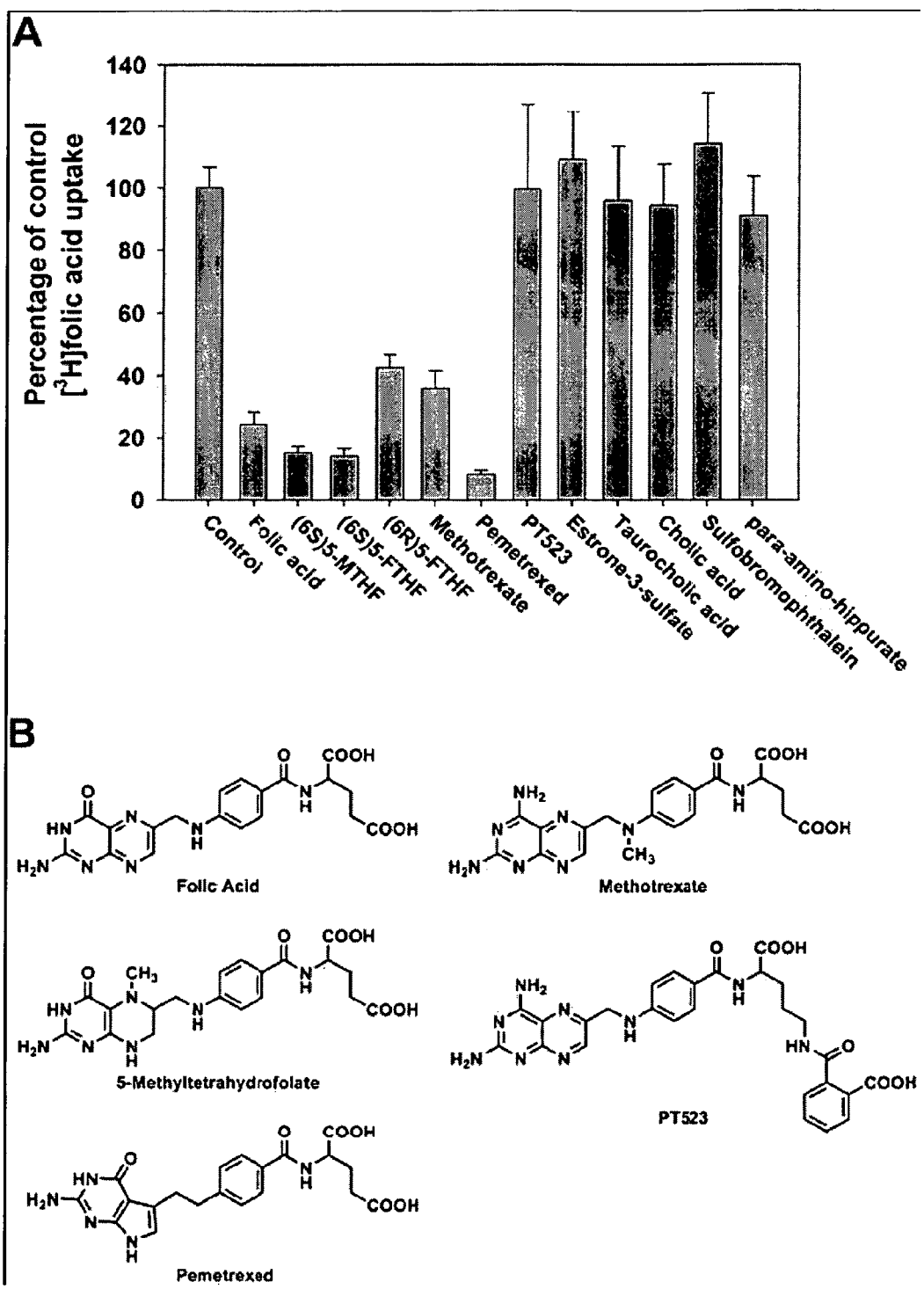

FIG. 3 is a graph and chemical structures showing substrate specificity of G21 in *Xenopus oocytes*. Panel A shows the uptake of 2 µM [³H]folic acid assessed at pH 5.5 over 30 min in the absence (control) or presence of 20 µM nonlabeled folates, antifolates, or other organic anions. The data is the mean±SEM of two independent experiments. Panel B shows the structures of folate and antifolate compounds studied.

Figure 4:
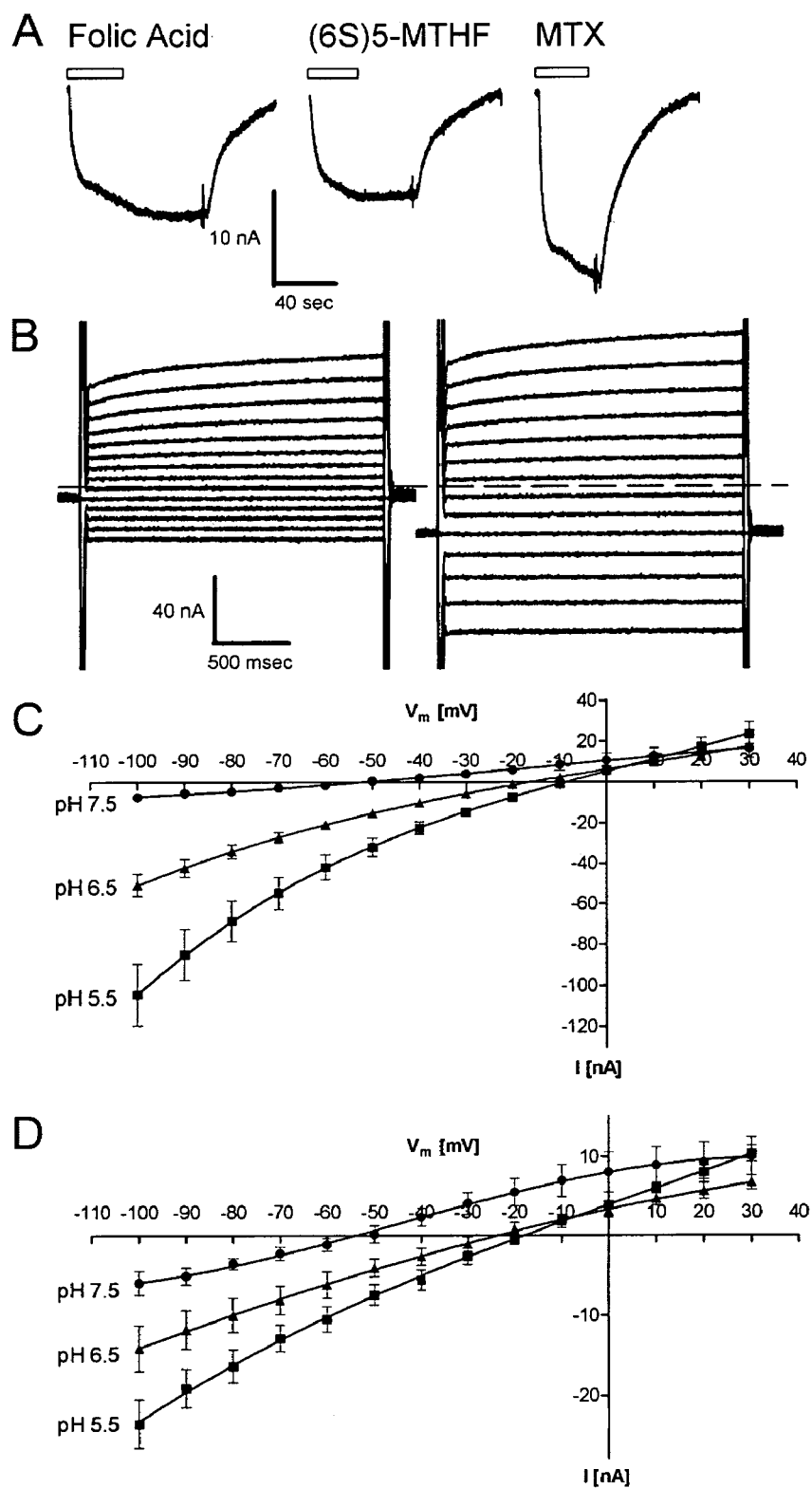

FIG. 4 is graphs of an electrophysiological characterization of the G21 transporter in *Xenopus oocytes*. Panel A shows substrate-induced currents recorded by two-electrode voltage-clamp from G21 expressing oocytes at a −80 mV holding potential with concentrations of folates 20-25 times the Km's at pH 5.5. Currents for all substrates were measured in individual oocytes (n=8 oocytes). A representative experiment from one oocyte is shown. Panel B shows currents from a G21-expressing oocyte, left superfused with buffer at pH 5.5, right superfused with MTX at 25 times the Km at pH 5.5. Responses to depolarizing and hyperpolarizing voltage clamp steps are shown. Oocytes were held at −60 mV and the voltage was stepped for 2 sec in 10 mV increments from −100 mV to +30 mV. The dashed line indicates the level of I=0. Panels C-D shows current-voltage relationships as a function of extracellular pH for MTX (Panel C) and (6S)5-MTHF (Panel D) with concentrations of 20-25 times the $K_m$s. Data are the mean±SEM for three to eight oocytes from two toads.

Figure 5:
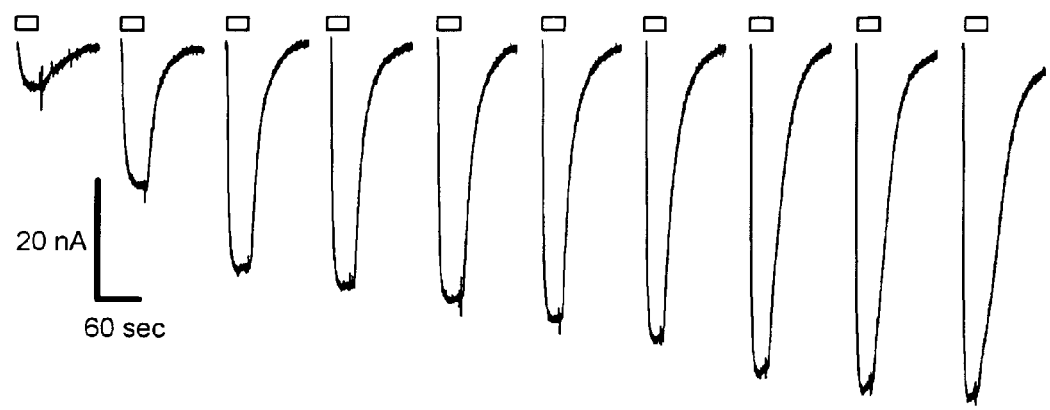
Figure 5:
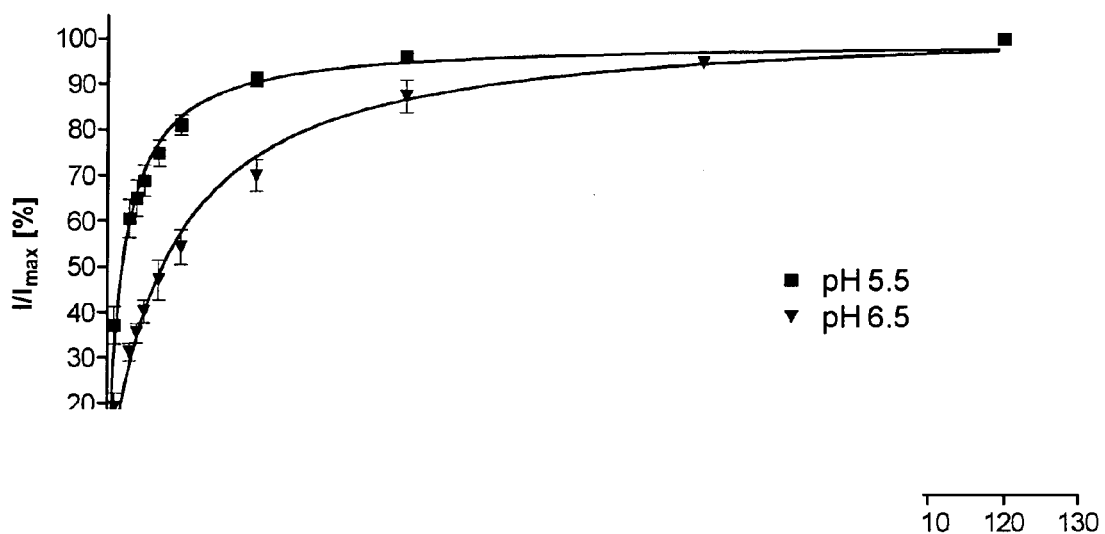

FIG. 5 is graphs showing concentration-dependence of substrate induced currents. Panel A shows currents recorded from an individual oocyte in response to (from left to right) 0.1, 1, 3, 4, 5, 7, 10, 20, 40, and 120 µM MTX (pH 5.5, $V_h$=−80 mV). Bars above current traces denote time of substrate application. Panel B shows currents obtained as described for Panel A at pH 5.5, and in similar experiments at pH 6.5, were normalized to the maximum current $I_{max}$ for each oocyte and plotted as a function of substrate concentration. The normalized currents from different experiments were fit to the equation $I=(I_{max}X[S])/(K_m+[S])$ to obtain $K_m$. Data are the mean±SEM for three to eight oocytes from two toads.

Figure 6:
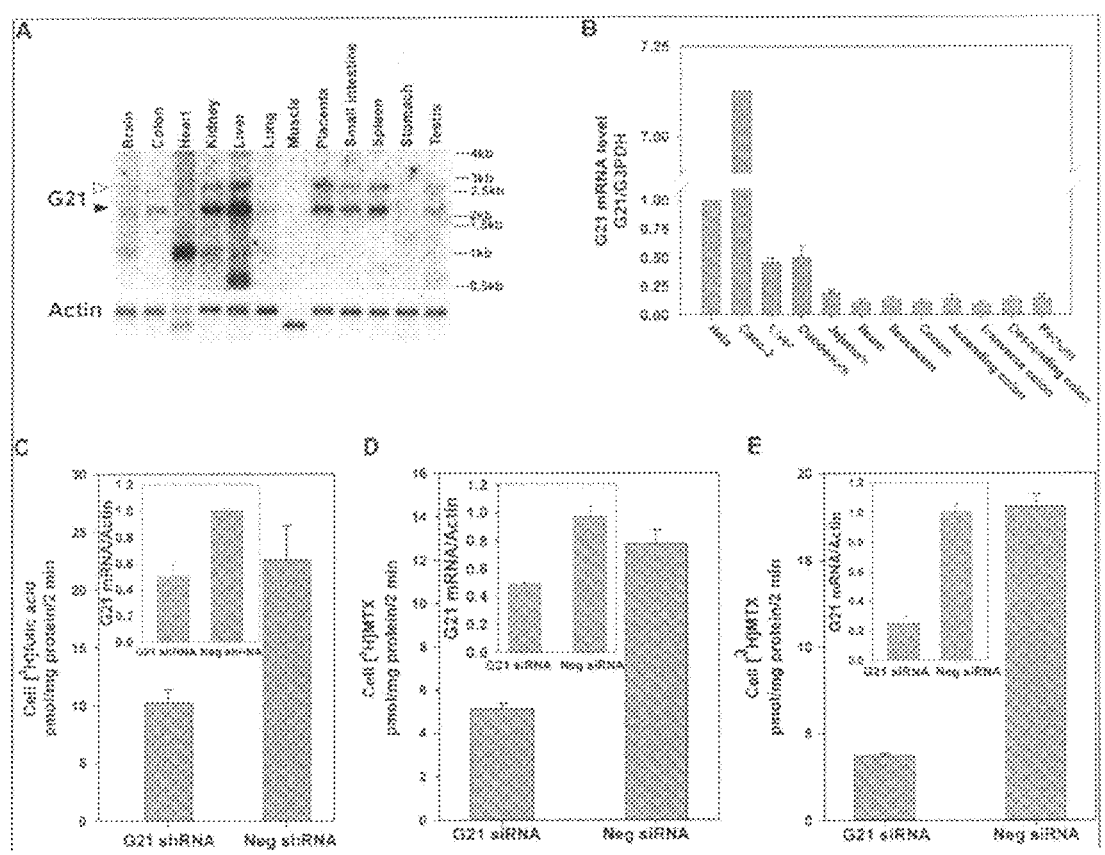

FIG. 6 is a photograph of a blot and graphs showing G21 mRNA levels in human tissues and tumor cell lines and suppression of G21 expression and folate transport activity in Caco2 cells by interfering RNA. Panel A shows the expression of G21 mRNA levels in human tissues by Northern blotting. β-actin was the loading control. Open and filled triangles indicate the location of two G21 major mRNA transcripts. Panel B shows G21 mRNA levels in two human cell lines and tissues as determined by quantitative RT-PCR. G3PDH mRNA was the house-keeping gene used to normalize G21 expression. The ordinate represents expression of G21 mRNA relative to expression in HeLa cells assigned the value of 1. Panel C shows the impact of stable transfection of G21 shRNA constructs into Caco2 cells on G21 mRNA levels determined by RT-PCR (inset) and uptake of [³H]folic acid (0.5 µM) at pH 5.5 and 37° C. for 2 min as compared to cells transfected with negative shRNA plasmids. Panel D shows the impact of transient transfection of Caco2 cells with siRNA duplex, using the Amaxa system, on G21 mRNA (inset) and uptake of [³H]MTX (0.5 µM) at pH 5.5 and 37° C. for 2 min as compared to cells with scrambled (Neg) siRNA. Panel E shows results when Caco2 cells stably transfected with the G21 shRNA constructs were subjected to transient transfection with siRNA duplex using the Amaxa system and both G21 mRNA levels (inset) and uptake of [³H]MTX (0.5 µM) at pH 5.5 and 37° C. for 2 min were assessed. The data in panels B-E are the mean±SEM from three independent experiments.

Figure 7:
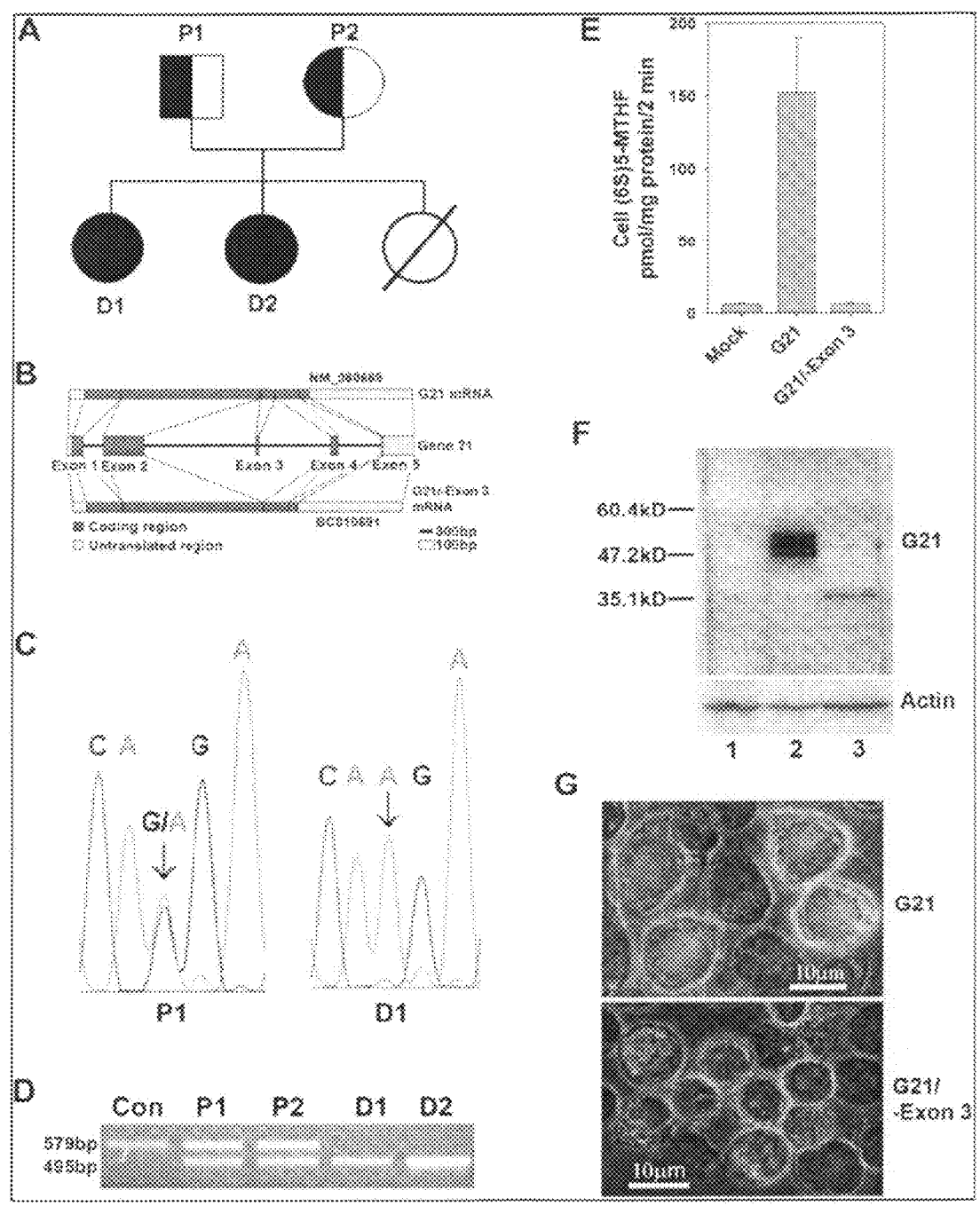

FIG. 7 is diagrams, sequencing chromatograms, photographs of a gel and a blot, and fluorescent micrographs showing results of a genetic and functional analysis of G21 in a family with hereditary folate malabsorption syndrome. Panel A is a genogram of the family members with hereditary folate malabsorption. P1 and P2 are the parents; D1 and D2 are the affected daughters. Panel B shows the genomic organization of G21 and splicing of the wild-type and mutated G21 mRNA. Panel C shows representative chromatograms of sequenced DNA showing a heterozygous mutation in father (P1) and a homozygous mutation in a daughter (D1) in G21. Panel D shows agarose gel analysis of RT-PCR products of mutated and wild-type G21 cDNA from family members. The control is a PCR-fragment derived from normal human intestinal cDNA. Panel E shows a functional analysis of exon 3-deleted G21 in HeLa cells. Exon 3-deleted (G21/-Exon 3), wild-type G21 cDNA (G21), and empty plasmid vector (Mock) were transiently transfected into HeLa cells. Uptake of (6S)[³H]5-MTHF (0.5 µM) was examined at pH 5.5 and 37° C. over 2 min. The data are the mean±SEM for four independent experiments. Panel F shows a western blot analysis of wild-type (Lane 2) and exon 3-deleted (Lane 3) G21 proteins in transiently transfected HeLa cells. Empty plasmid (Mock) was transfected into HeLa cells as a control (Lane 1). β-actin was the loading control. The blot is representative of three independent experiments. Panel G shows the subcellular localization of wild-type (G21) and exon 3-deleted (G21/-Exon 3) G21 proteins expressed in transiently transfected HeLa cells as determined by immunofluorescence. The image shown is representative of three independent studies.

Figure 8:
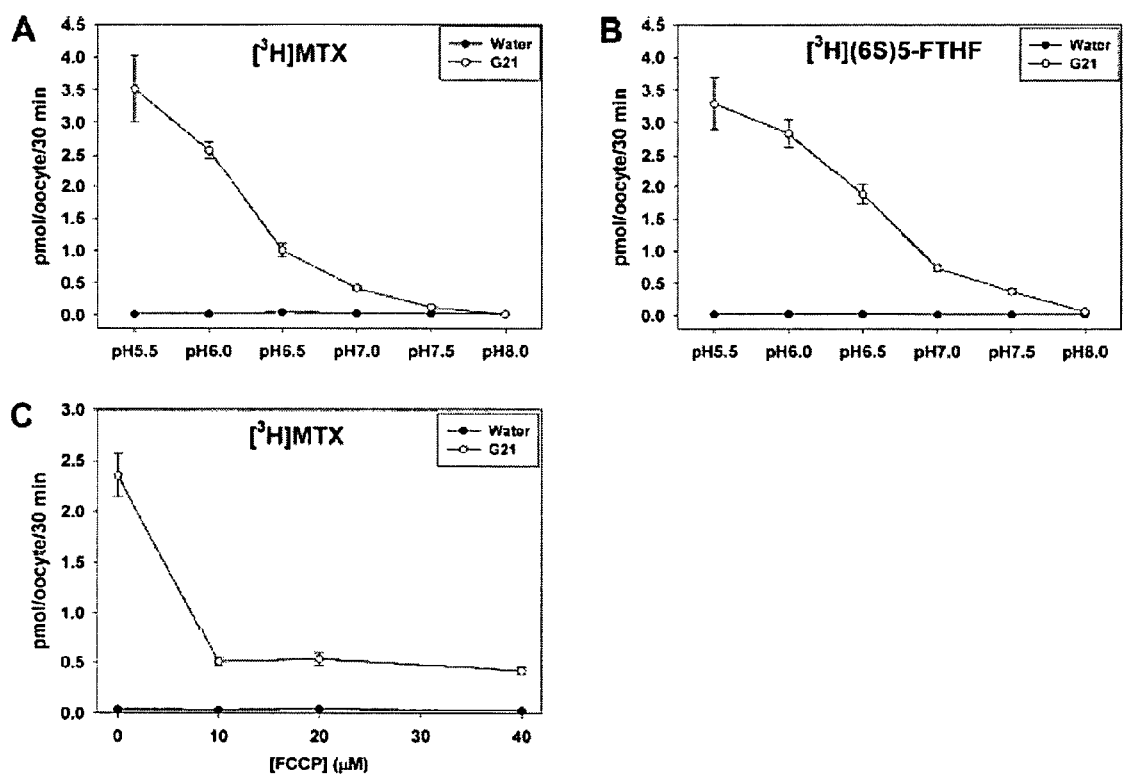

FIG. 8 is graphs showing the pH dependence of G21-mediated uptake of tritiated MTX and (6S)5-FTHF in *Xenopus oocytes*. Panels A and B show uptake of 2 μM [$^3$H]MTX (Panel A) and [$^3$H](6S)5-FTHF (B) in water- and G21 cRNA-injected *Xenopus* oocytes over 30 min. Panel C shows the results when water- and G21 cRNA-injected oocytes were incubated at pH 5.5 with 0, 10, 20, or 40 μM FCCP for 20 min. Uptake of [$^3$H]MTX (2 μM) was subsequently assessed at pH 5.5 over 30 min. Data are the mean±SEM. Panels A to C are representative of three independent studies.

Figure 9:
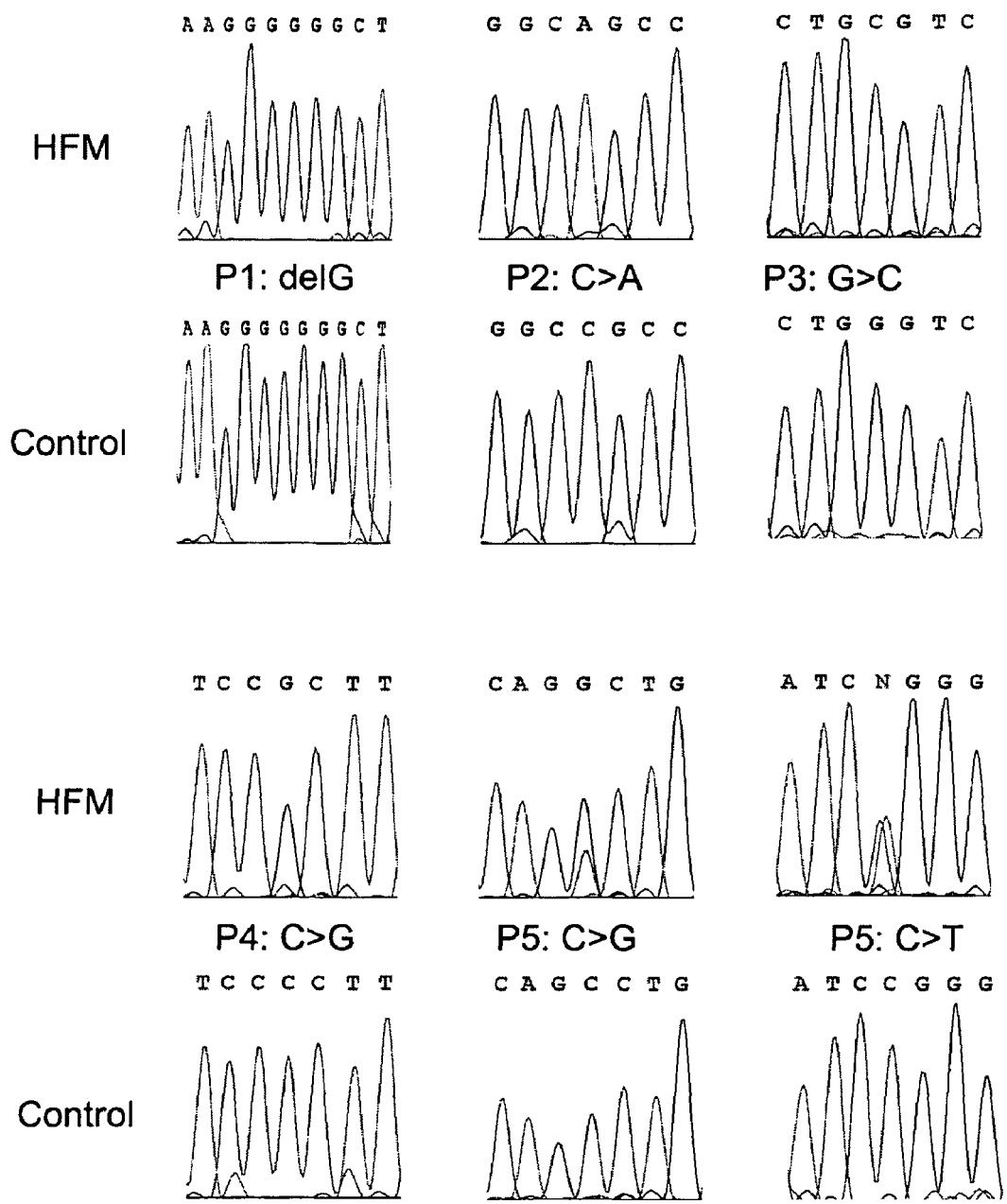

FIG. 9 shows representative chromatograms of DNA sequence data for each PCFT mutation identified. Upper panels (HFM) represent the mutated DNA in HFM patients, whereas the bottom panels (control) are corresponding wild-type sequences.

Figure 10:
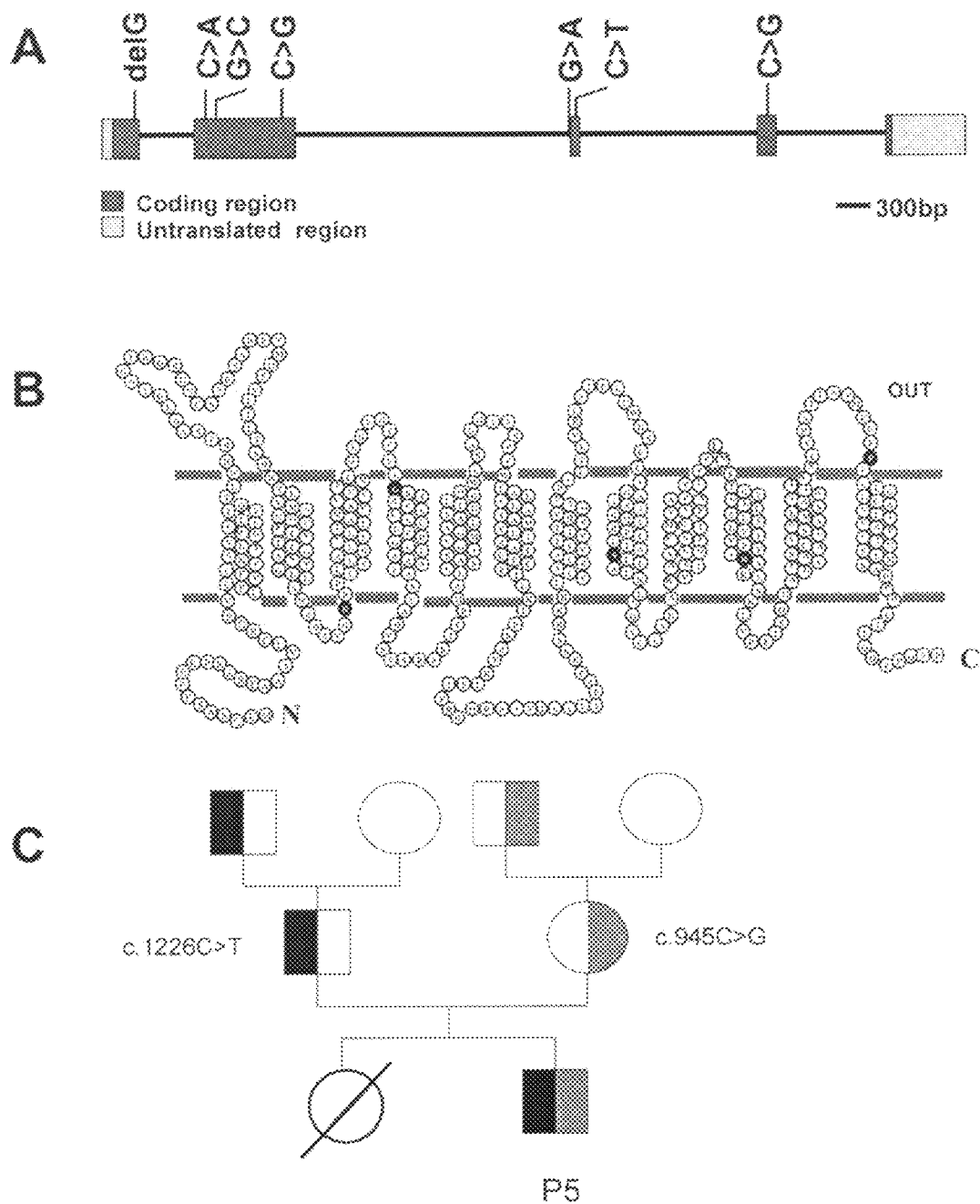

FIG. 10 is diagrams showing the location of the identified mutations in PCFT and the pedigree of a family of an HFM patient. Panel A shows the genomic organization of the PCFT gene and the location of mutations detected in patients with HFM. Panel B shows the location of amino acid substitutions associated with mutations in PCFT within the context of the predicted secondary structure of this carrier protein. Panel C shows the pedigree of the family of patient P5. The black color indicates the c.1126C>T mutation and the gray color indicates the c.954C>G mutation.

Figure 11:
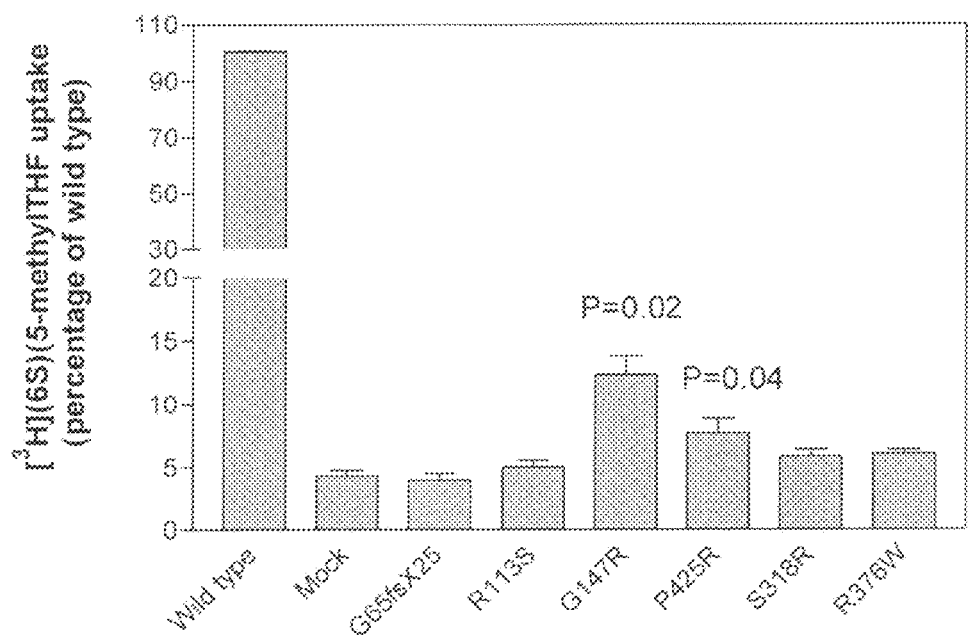

FIG. 11 is a graph showing [$^3$H](6S)5-methylTHF uptake in HeLa cells transiently transfected with the cDNA of PCFT mutants. Uptake of 0.5 μM [$^3$H]5-methylTHF was assessed at pH 5.5 and 37° C. over 2 min; p values reflect differences in activities of the mutated carriers as compared to the mock transfectants. The data are the mean±SEM from three independent experiments.

Figure 12:
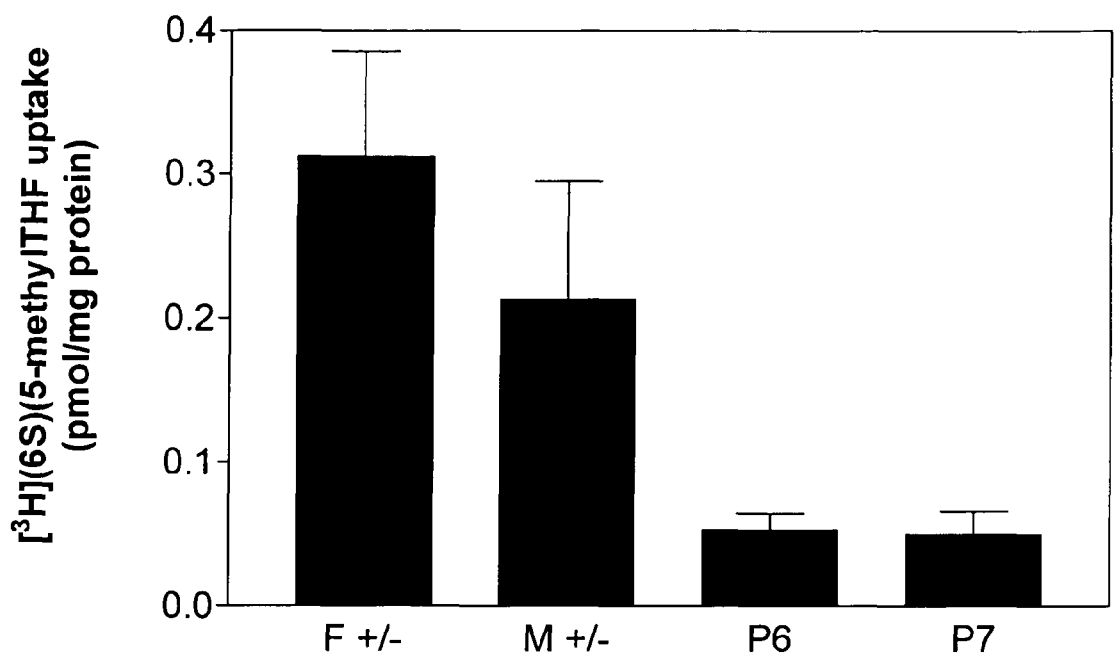

FIG. 12 is a graph showing [$^3$H](6S)5-methylTHF uptake at low pH in lymphocytes derived from patients 6 and 7 and their parents. Uptake at pH 5.5 was assessed as described in the legend to FIG. 11. F± and M± indicate cells derived from father and mother, respectively, who each carry one mutated PCFT allele. The data are the mean±SEM from three independent experiments.

DETAILED DESCRIPTION OF THE INVENTION

The present invention is based on the discovery of the genetic basis for hereditary folate malabsorption, the proton-coupled folate transporter (PCFT) gene, which is required for intestinal absorption of folates, and the identification of several mutations in the PCFT gene. See Examples.

As elaborated in the Examples, the PCFT gene was previously identified as an intestinal heme carrier protein in mice (Shayeghi et al., 2005). The human gene, protein and cDNA was identified in that work using a BLAST search; the isolation of the human gene or cDNA was not described therein. There were two published sequences for the cDNA of that gene, GenBank NM_080669 (SEQ ID NO:1) and GenBank BC010691 (SEQ ID NO:3), providing two alternate protein sequences, GenBank NP_542400 (SEQ ID NO:2) and GenBank AAH10691 (SEQ ID NO:4). Since the human protein and its cDNA was not isolated until the work described in Example 1, there was uncertainty as to the utility of the human gene and protein.

Thus, the present invention is directed to isolated and purified DNA molecules comprising a sequence at least 95% identical to SEQ ID NO:31. SEQ ID NO:31 is the coding region of the human cDNA encoding active PCFT. Preferably, the DNA molecule comprises a sequence at least 99% identical to SEQ ID NO:1. More preferably, the DNA molecule is naturally occurring in a human. In some aspects of the invention, the DNA molecule comprises SEQ ID NO:31.

Some of the invention DNA molecules encodes a non-functional PCFT. Some of these non-functional PCFTs comprise 194delG. Others comprise 337C>A. Still others comprise 439G>C. Additional DNA molecules that encode a non-functional PCFT comprise 1274C>G. Other such DNA molecules comprise 954C>G. Still other such DNA molecules comprise 1126C>T.

Mutations described herein follow the nomenclature derived by the Human Genome Variation Society (http://www.hgvs.org/mutnomen).

As used herein, a "non-functional" or "inactive" PCFT is a PCFT that is incapable of proton-coupled folate transport in vitro (e.g., using the in vitro methods described in the Examples) or in vivo. Conversely, a functional or active PCFT is capable of intestinal folate transport. An active human PCFT would be expected to have an amino acid sequence at least 95% identical to SEQ ID NO:2.

The invention is also directed to segments of a DNA molecule having a sequence at least 95% identical to the cDNA of the cloned active PCFT, having the sequence of SEQ ID NO:1. These invention segments are preferably capable of serving as a primer for amplifying at least a portion of the DNA molecule. More preferably, the DNA segment has a sequence at least 99% identical to SEQ ID NO:1. Even more preferably, the DNA segment comprises the sequence of SEQ ID NO:7, 8, 9, 10, 11, 12, 29 or 30.

Additionally, the invention is directed to segments of a DNA molecule having a sequence at least 95% identical to the PCFT gene, having the sequence of SEQ ID NO:6. These invention segments are preferably capable of serving as a primer for amplifying at least a portion of the DNA molecule. More preferably, the DNA molecule has a sequence at least 99% identical to SEQ ID NO:6. Even more preferably, the DNA molecule has the sequence of SEQ ID NO:6. Most preferably, the segment comprises the sequence of SEQ ID NO: 17, 18, 19, 20, 21, 22, 23, 24, 25, 26, 27, or 28.

With any of the above-described segments (i.e., those homologous to SEQ ID NO:1 as well as those homologous to SEQ ID NO:6), the segment is preferably 15-35 nucleotides long. More preferably, the segment is 17-31 nucleotides long.

The invention is additionally directed to pairs of the above-described segments of a DNA molecule having a sequence at least 95% identical to the cDNA of the cloned active PCFT, having the sequence of SEQ ID NO:1, where the pair can be used together as forward and reverse PCR primers for amplifying at least a portion of the DNA molecule. Preferably, at least one of these segments comprises the sequence of SEQ ID NO: 7, 8, 9, 10, 11, 12, 29 or 30.

The invention is further directed to pairs of the above-described segments of a DNA molecule having a sequence at least 95% identical to the PCFT gene, having the sequence of SEQ ID NO:6, where the pair can be used together as forward and reverse PCR primers for amplifying at least a portion of the DNA. Preferably, at least one of the segments comprises the sequence of SEQ ID NO:7, 8, 9, 10, 11, 12, 29 or 30.

The invention is also directed to isolated and purified human PCFTs comprising an amino acid sequence at least 95% identical to SEQ ID NO:4. SEQ ID NO:4 is an inactive PCFT that lacks exon 3. Preferably, the PCFT comprises an amino acid sequence at least 99% identical to SEQ ID NO:4. More preferably, the PCFT consists of SEQ ID NO:4. Even more preferably, the human PCFT comprises an amino acid sequence at least 95% identical to SEQ ID NO:2. SEQ ID NO:2 is the amino acid sequence of the wild-type, active human PCFT. Still more preferably, the human PCFT comprises an amino acid sequence at least 99% identical to SEQ ID NO:2. Most preferably, the human PCFT here consists of SEQ ID NO:2.

Some of the human PCFTs here have less than 20% of the activity of the wild-type PCFT consisting of the amino acid sequence of SEQ ID NO:2. Others have less than 5% of the activity of the PCFT consisting of the amino acid sequence of SEQ ID NO:2. Still others are inactive, i.e., the PCFT has no folate transport activity. One of the human PCFTs here comprises the amino acid sequence of SEQ ID NO:2 except for the mutation 337C>A. Another of the human PCFTs comprises the amino acid sequence of SEQ ID NO:2 except for the mutation 439G>C. Still another of the human PCFTs here comprises the amino acid sequence of SEQ ID NO:2 except for the mutation 1274C>G. An additional human PCFT comprises the amino acid sequence of SEQ ID NO:2 except for the mutation 954C>G. A further human PCFT here comprises the amino acid sequence of SEQ ID NO:2 except for the mutation 1126C>T.

The invention is further directed to methods of evaluating the ability of a human to undergo intestinal folate absorption. The methods comprise determining whether the human expresses an active PCFT having an amino acid sequence at least 95% homologous to SEQ ID NO:2, where the human has the ability to undergo intestinal folate absorption if the human expresses the active PCFT. Preferably, the active PCFT has an amino acid sequence at least 99% identical to SEQ ID NO:2. More preferably, the active PCFT has the amino acid sequence of SEQ ID NO:2.

The skilled artisan can, without undue experimentation, determine what tissue to use to evaluate whether the human can undergo intestinal folate absorption. With some of these methods, peripheral blood lymphocytes are evaluated for expression of an active PCFT. With others, tissue from a biopsy is evaluated for expression of an active PCFT.

In some aspects of these methods, the human is a fetus. In those cases, amniotic fluid or chorionic villus are preferably evaluated. In other aspects, the human is a pregnant woman.

With some of these methods, activity of intestinal folate absorption is measured directly, e.g., using the in vitro methods described in the Examples. In others of these methods, the genotype of the PCFT gene in the human is determined. Here, a PCFT gene having a DNA sequence at least 95% identical to SEQ ID NO:6 encodes an active PCFT. Preferably, a PCFT gene having a DNA sequence at least 99% identical to SEQ ID NO:6 encodes an active PCFT. Most preferably, a PCFT gene having the DNA sequence of SEQ ID NO:6 encodes an active PCFT.

In some cases, the gene comprises a mutation causing a reduction or elimination of intestinal folate absorption. Here, the gene can comprise a mutation causing a deletion in the amino acid sequence of the expressed protein, where the full length amino acid sequence is at least 99% identical to SEQ ID NO:2. The gene can also comprise a mutation causing an amino acid substitution. In some cases, the mutation in the gene is 5882G>A of SEQ ID NO:6. In other cases, the mutation in the gene is 2284delG of SEQ ID NO:6. In still other cases, the mutation in the gene is 2844C>A of SEQ ID NO:6. In additional cases, the mutation in the gene is 2946G>C of SEQ ID NO:6. In further cases, the mutation in the gene is 3461C>G of SEQ ID NO:6. In still additional cases, the mutation in the gene is 5927C>T of SEQ ID NO:6. In still further cases, the mutation in the gene is 7548C>G of SEQ ID NO:6.

In these methods, the human can be heterozygous for an inactive PCFT. Such humans would be expected to undergo intestinal folate absorption, although likely at a reduced rate. In other cases, the human does not have an active PCFT. In these cases, both PCFT alleles would usually be expected to comprise a mutation causing a reduction or elimination of intestinal folate absorption activity.

With other of these methods, PCFT mRNA from the mammal is evaluated to determine whether mRNA of an active PCFT is present. Preferably here, the mammal is human and the PCFT mRNA is evaluated by making a cDNA from the PCFT mRNA and determining whether the cDNA comprises a sequence at least 95% identical to SEQ ID NO:31 and encodes a protein having the amino acid sequence of SEQ ID NO:2. In these methods, the presence of cDNA having a sequence at least 95% identical to SEQ ID NO:31 and encoding a protein having the amino acid sequence of SEQ ID NO:2 indicates the presence of an active PCFT in the human. More preferably, the mammal is human and the PCFT mRNA is evaluated by making a cDNA from the PCFT mRNA and determining whether the cDNA comprises a sequence at least 99% identical to SEQ ID NO:31 and encodes a protein having the amino acid sequence of SEQ ID NO:2. Here, the presence of cDNA comprising a sequence at least 99% identical to SEQ ID NO:31 and encoding a protein having the amino acid sequence of SEQ ID NO:2 indicates the presence of an active PCFT in the human. Most preferably, the mammal is human and the PCFT mRNA is evaluated by making a cDNA from the PCFT mRNA and determining whether the cDNA comprises the sequence of SEQ ID NO:31, wherein the presence of cDNA comprising the sequence of SEQ ID NO:31 indicates the presence of an active PCFT in the human.

In some of these methods, tissue of the mammal is tested for PCFT activity. Here, the PCFT activity is preferably determined by measuring uptake of a radiolabeled substrate of PCFT. Most preferably, the radiolabeled substrate of PCFT is [$^3$H]folic acid, [$^3$H]pemetrexed, [$^3$H]methotrexate, [$^3$H]5-methyltetrahydrofolate, or [$^3$H]5-formyltetrahydrofolate.

These methods can be used to evaluate the ability of a healthy human to undergo intestinal folate absorption. Alternatively, the methods can be used to evaluate the ability of a human with a disorder associated with low folate levels to undergo intestinal folate absorption. Preferably, the human has low serum folate levels. In severe cases, the human has megaloblastic anemia, immune deficiency and infections, diarrhea, and/or neurological defects such as mental retardation, seizures, paralysis and gait abnormalities. The human can also have a neural tube defect. Additionally, the human can be at a high risk for cancer or cardiovascular disease. The human can also have cancer or cardiovascular disease. Additionally, mothers carrying one defective gene may be at risk for delivering a baby with congenital neural tube defects.

In other cases, the methods can be used with a human that takes methotrexate. The human can also have Alzheimer's disease. The human can further have cancer, chronic fatigue syndrome or depression. These methods are also useful where the human is an alcoholic. Also, the human can have, or be at risk for, nitroglycerine-induced nitrate tolerance. The human can further have, or be at risk for, phenytoin-induced gingival hyperplasia. The human can also have, or be at risk for, pregnancy-related gingivitis. The human can additionally have, or be at risk for, vitiligo.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Identification of an Intestinal Folate Transporter and the Molecular Basis for Hereditary Folate Malabsorption Example Summary Folates are essential nutrients required for one-carbon biosynthetic and epigenetic processes. While folates are absorbed in the acidic milieu of the upper small intestine, the underlying absorption mechanism has not been defined. We now report the identification of a human proton-coupled, high-affinity, folate transporter that recapitulates properties of folate transport and absorption in intestine and in various cell types at low pH. We demonstrate that a loss-of-function mutation in this gene is the molecular basis for Hereditary Folate Malabsorption in a family with this disease. This transporter was previously reported to be a lower affinity, pH-independent, heme carrier protein, HCP1. However, the current study establishes that the major function of this gene product is proton coupled folate transport required for folate homeostasis in man and we have thus amended the name to PCFT.

Introduction

This report describes the identification of a proton-coupled, electrogenic, high-affinity folate transporter with properties that are similar to folate transport in intestinal and other cells at low pH. A database mining approach was utilized based upon the conserved amino acid sequence of SLC19 family members and the screening of candidate mRNAs in cell lines developed in this laboratory in which the reduced folate carrier was deleted but the low pH activity was either retained or markedly decreased (Zhao et al., 2004; Zhao et al., 2004a). Having identified this carrier as a candidate intestinal folate transporter, a loss-of-function mutation is demonstrated in this gene in a family with the syndrome of hereditary folate malabsorption.

Results

Figure 1:
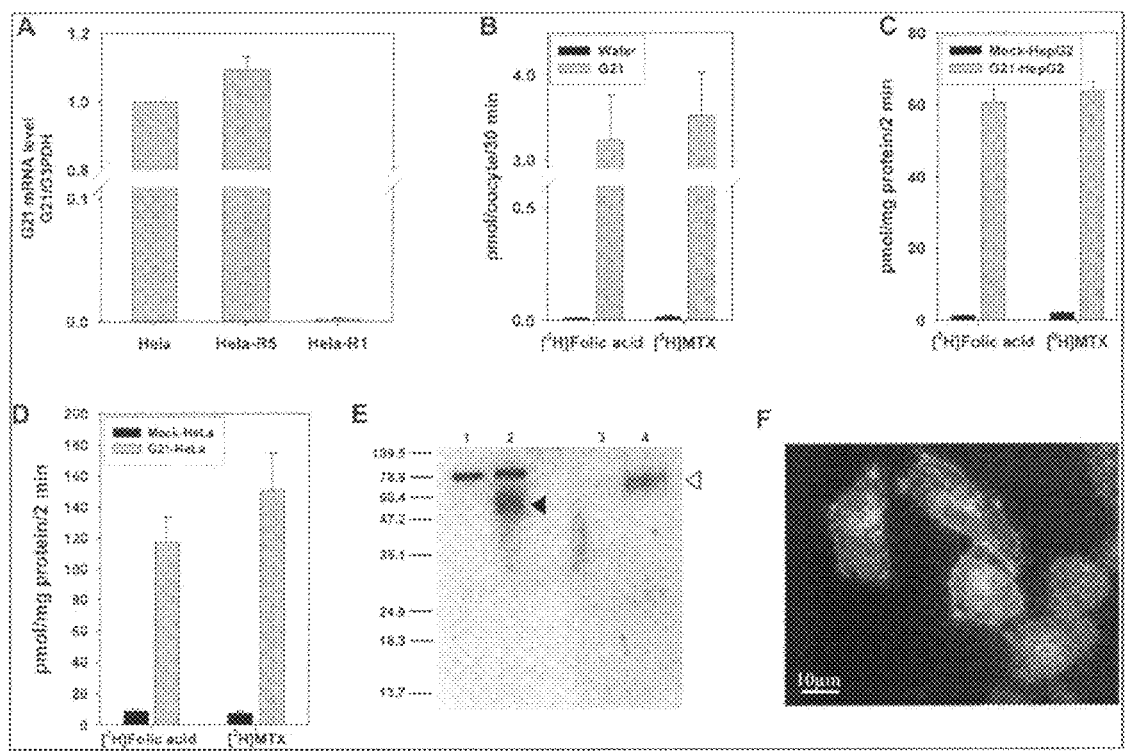
FIG. 1 is graphs, a photograph of a blot, and a fluorescent micrograph showing the identification and initial characterization of the low-pH folate transporter. Panel A shows G21 (SEQ ID NO:1) mRNA levels in HeLa, HeLa-R5, and HeLa-R1 cells determined by quantitative RT-PCR. G21 mRNA in HeLa cells was assigned the value of 1. The values are the mean±SEM for two independent experiments. Panel B shows the functional expression of G21 in *Xenopus oocytes*. [$^3$H]

Identification of a low-pH folate transporter. To identify the low-pH folate transporter, the Ensembl human peptide database was mined at low stringency as described in Experimental Procedures below. Twenty-three human genes encoding membrane proteins with unknown functions were identified and mRNA expression levels were screened in the following two HeLa cell lines: (1) The HeLa-R5 (Zhao et al., 2004), with a genomic deletion of the reduced folate carrier gene but a high level of low-pH folate transport activity and (2) the HeLa-R1 line (Zhao et al., 2004a), a HeLa-R5 derivative, cloned by antifolate selective pressure, in which the low-pH activity is markedly diminished. Gene 21 (to be referred to as G21) was identified in this screen as a likely candidate based upon a high mRNA level in HeLa-R5 cells versus a very low level of expression in HeLa-R1 cells (FIG. 1A). G21 (GenBank accession No. NP_542400) is predicted to be a membrane protein of 459 amino acids with a MW of ~50 kDa. A BLAST-search of the Swissprot database revealed that the human protein shares 91% similarity and 87% identity to both its mouse and rat counterparts (GenBank accession No. AAH57976 and AAH89868). During the course of the studies described below, this protein was reported by another group to be a heme carrier protein (HCP1) and entered into GenBank as such (Shayeghi et al., 2005). This protein was designated as SLC46A1 in the Human Genome Organization (HUGO) Nomenclature Committee Database.

Folate transport properties mediated by this carrier were assessed by injection of G21 cRNA into *Xenopus laevis* oocytes. As indicated in FIG. 1B, uptake of 2 μM [$^3$H]folic acid and [$^3$H]methotrexate (MTX) was increased >200-fold into G21 cRNA-injected oocytes at pH 5.5 as compared to water-injected oocytes. Similarly, uptake of these folates into HepG2 cells stably transfected with G21 cDNA (FIG. 1C) and into HeLa cells transiently transfected with G21 cDNA (FIG. 1D) was increased >30 and >13-fold, respectively. A western blot using a polyclonal antibody directed to the C-terminus of G21 indicated a broad band in G21 cRNA-injected, but not water-injected, *Xenopus* oocytes and in HepG2 cells stably transfected with this cDNA but not in mock-transfected cells (FIG. 1E). Differences in migration in the two systems may be due to differences in glycosylation. When expressed in HeLa cells, G21 protein targeted to the plasma membrane in permeabilized cells as demonstrated with the polyclonal antibody (FIG. 1F). Staining could not be detected in mock-transfected HeLa cells (data not shown).

The pH-dependence of G21-mediated transport. Transport of folates mediated by G21 was highly pH-dependent as illustrated for tritiated folic acid (FIG. 2A), (6S)5-methyltetrahydrofolate, ((6S)5-MTHF, FIG. 2B), MTX (FIG. 8A) and (6S)5-formyltetrahydrofolate ((6S)5-FTHF, FIG. 8B). Activity was highest at the lowest pH and declined as the pH was increased although the pattern of decrease, and the extent of retention of activity at neutral pH, was different among the folates. For both (6S)5-MTHF, the major blood folate in man and rodents, and (6S)5-FTHF, there was residual activity at pH 7.5 and for all the folates there was substantial activity at pH 6.5. The dependence of G21 activity on the inward-directed electrochemical H$^+$ gradient was further characterized by exposure of *Xenopus* oocytes to carbonyl cyanide 4-(trifluoromethoxy) phenylhydrazone (FCCP), an ionophore that collapses the transmembrane H+ gradient (Benz and McLaughlin, 1983). As shown in FIG. 2C and FIG. 8C, respectively, at an extracellular pH of 5.5, [$^3$H]folic acid and [$^3$H]MTX uptake were markedly decreased by 10 μM FCCP.

The kinetics of folate transport mediated by G21 as a function of pH. Uptake mediated by G21 conformed to Michaelis-Menten kinetics with a $K_m$ for [$^3$H]folic acid uptake, which increased as pH increased, from 1.3±0.1 μM at pH 5.5 to 56.2±5.6 μM at pH 7.5 (FIG. 2D-2G, Table 1). $V_{max}$ as well as $K_m$ were evaluated as a function of pH using the same batch of oocytes each injected with the same amount of G21 cRNA. As shown in FIG. 2G, the $V_{max}$ for folic acid uptake decreased from 13 pmol/oocyte/hr at pH 5.5 to 5 pmol/oocyte/hr at pH 7.5. The major change (2.4-fold) occurred over the pH range of 5.5 to 6.5, with only a small decline beyond pH 6.5. The pattern of change was different for the folic acid $K_m$ measured at the same time. There was a small (2.6-fold) increase in $K_m$ as the pH was increased from 5.5 to 7.0; but there was a 18-fold increase when the pH was increased from 7.0 to 7.5. Table 1 indicates a two- to three-fold higher uptake $K_m$ for MTX as compared to folic acid over this pH range with a similar pattern of increase as the pH was increased.

TABLE 1

Summary of uptake $K_m$ for MTX and folic acid as a function of extracellular pH. All data are the mean ± SEM

| | $K_m$ [μM] | |
|---|---|---|
| | MTX | Folic acid |
| pH 5.5 | 3.4 ± 0.8 (n = 3) | 1.3 ± 0.1 (n = 4) |
| pH 6.0 | 3.4 ± 0.5 (n = 3) | 1.5 ± 0.1 (n = 2) |
| pH 6.5 | 7.3 ± 0.6 (n = 3) | 2.7 ± 0.2 (n = 3) |
| pH 7.0 | 16.3 ± 2.8 (n = 4) | 6.0 ± 2.6 (n = 2) |
| pH 7.5 | 130.7 ± 11.6 (n = 3) | 56.2 ± 5.6 (n = 2) |

Structural specificity of G21-mediated transport. FIG. 3A shows the inhibitory effects of a variety of compounds, at a concentration of 20 μM, on uptake of 2 μM [$^3$H]folic acid into Xenopus oocytes injected with G21 cRNA. There was a high degree of structural specificity among the folate/antifolate compounds tested; pemetrexed was the most potent competitor. This is a novel antifolate inhibitor of thymidylate synthase with the highest affinity for the low-pH transporter in human tumor cell lines (Zhao et al., 2005b; Wang et al., 2004). Transport is stereospecific, the natural 6S isomer of 5-FTHF was more potent than the unnatural 6R isomer in reducing [$^3$H]folic acid uptake. The 6S isomer of 5-MTHF had effects comparable to those of (6S)5-FTHF. MTX was a less effective competitor than folic acid, consistent with the difference in transport $K_m$s. PT523 is a dihydrofolate reductase inhibitor with a high affinity for the reduced folate carrier at high and low pH but a very low affinity ($K_i$>50 μM) for the low-pH folate transporter in HeLa and other cells (Zhao et al., 2005b; Wang et al., 2004). That antifolate did not inhibit under these conditions. All the folates that inhibited [$^3$H]folic acid uptake are transport substrates of G21. Thus, the inhibition of [$^3$H] folic acid uptake was due to competition for transport via G21. FIG. 3B compares the structures of these folate compounds. The major difference between PT523 and the other folates/antifolates is at the γ-carboxyl moiety suggesting the importance of this group to folate binding to G21. Bromosulphophthalein, para-aminohippuric acid, taurocholic acid, cholic acid, and estrone-3-sulfate, substrates for organic anion solute carriers (SLC21 and SLC 22) (Hagenbuch and Meier, 2003; Koepsell and Endou, 2004) did not inhibit [$^3$H] folic acid influx. Hemin was a weak inhibitor. At a [$^3$H]folic acid concentration of 2 μM, 100 μM hemin inhibited uptake by 42±7% in Xenopus oocytes injected with G21 cRNA and by 30±5% in HepG2 cells stably transfected with G21 cDNA. In the same experiments, 100 μM non-labeled folic acid inhibited 2 μM [$^3$H]folic acid uptake by 92±2% and 90±0.02%, respectively (based upon the average of three separate experiments at pH 6.5).

Electrophysiological properties of G21-mediated transport in Xenopus oocytes. Electrophysiological characteristics were evaluated in two-electrode voltage-clamp experiments. In G21 cRNA-injected oocytes, folic acid, (6S)5-MTHF, and MTX induced currents of up to 80 nA at a −80 mV holding potential (FIG. 4A). These folates did not induce current in water-injected oocytes. These substrate-induced currents imply that net charge translocation occurred across the cell membrane during each transport cycle. Consistent with this, substrate currents were proportional to both applied voltage and substrate concentration, increasing with more negative voltage and higher substrate concentration (FIGS. 4B-4D and 5).

In order to distinguish between whether folate transport was coupled to proton transport (i.e. protons are transported with the folate) or whether protons just bind to the transporter and regulate its activity, the effect of changing extracellular pH from 5.5 to 7.5 was determined on the substrate current-voltage relationship. The reversal potential of the current-voltage relationship is the voltage at which the substrate-induced current is zero (the x-axis intercept in FIGS. 4C and 4D) and is a measure of the net driving force for substrate transport. If folate and proton transport are coupled, then the reversal potential would become more negative as the extracellular pH is raised and the slope would decrease. In contrast, if the folate transport rate was only regulated by pH then the slope of the current-voltage relationship would decrease but the reversal potential would not change. As the pH increased, the reversal potential became more negative (FIGS. 4C and 4D). Changing the pH from 5.5 to 6.5 shifted the reversal potentials for MTX and (6S)5-MTHF by −8 mV and −6 mV, respectively, whereas increasing the pH from 6.5 to 7.5 shifted the reversal potentials by −36 mV and −30 mV, respectively. This change in the reversal potential with a change in pH provides direct evidence that the transmembrane proton gradient is coupled to folate transport. These results are consistent with the loss of net proton influx driving transport as the extracellular pH increased to a value comparable to an intracellular pH of ~7.3. At pH 7.5, the transmembrane proton gradient is close to zero and folate influx is driven solely by the folate concentration gradient due to the higher extracellular folate concentration. Thus, the reversal potential is more negative at pH 7.5 than at lower pHs where the transmembrane proton gradient also contributes to the net driving force for transport. FIG. 5A shows the currents recorded from an individual oocyte as the extracellular MTX concentration was increased from 0.1 to 120 μM. Current was detected at a MTX concentration as low as 0.1 μM. FIG. 5B illustrates the dependence of current on the MTX concentration at pH 5.5 and 6.5. The $K_m$s for folic acid, (6S)5-MTHF, and MTX (Table 2) and their pH dependence, were comparable in the electrophysiological and the tritiated substrate uptake assays (Tables 1 and 2). The $K_m$s at pH 6.5 for folic acid and MTX were nearly four times greater than those at pH 5.5 while the $K_m$ for (6S)5-MTHF was only minimally increased. The relative current magnitude induced by the different substrates was assessed by applying saturating concentrations of each substrate to the same oocyte at pH 5.5 (FIG. 4A). When normalized to the (6S)5-MTHF-induced current magnitude, the current amplitudes were 39±6%, and 86±11% (n=8) larger for folic acid and MTX, respectively, despite the fact that the latter substrates had higher $K_m$s (Table 2). This implies that the transport $V_{max}$ for these substrates was higher than for (6S)5-MTHF.

TABLE 2

Summary of the electrophysiologically determined $K_m$ values for folic acid, (6S)5-MTHF and MTX as a function of extracellular pH. The data is the mean ± SEM for 3 to 7 experiments.

| | $K_m$ [μM] | |
|---|---|---|
| Substrate | pH 5.5 | pH 6.5 |
| Folic Acid | 0.83 ± 0.05 | 2.99 ± 0.09 |
| (6S)5-MTHF | 0.53 ± 0.04 | 0.78 ± 0.14 |
| MTX | 2.01 ± 0.16 | 8.07 ± 0.60 |

An attempt was made to determine if hemin transport could be detected by current flow into oocytes injected with G21 cRNA. In two separate experiments using two different batches of oocytes, 3-4 oocytes for each condition, folic acid produced substantial currents, while no current could be detected with 100 μM hemin either when hemin was stabilized with 0.1% bovine serum albumin or with 200 μM arginine (data not shown). If hemin were transported by G21 in an electrogenic fashion similar to the folates, then the "expected" currents from this approximately EC50 hemin concentration (reported hemin $K_m$ of 125 μM (Shayeghi et al., 2005)) would be well within the detection limits of this system.

Lack of impact of other extracellular ions on G21-mediated transport into oocytes. Substitution of extracellular $Na^+$ with N-methyl-glucosamine did not decrease [$^3$H]MTX uptake into G21 cRNA-injected oocytes excluding a sodium-dependent process. Similarly, folic acid-induced currents were unchanged when $K^+$, $Ca^{2+}$, or $Mg^{2+}$ were removed from the extracellular solution or when the extracellular $Cl^-$ concentration was reduced from 95.6 mM to 5.6 mM by replacement of NaCl with Na-gluconate. Thus, folate transport was not dependent on extracellular $Na^+$, $K^+$, $Ca^{2+}$, $Mg^{2+}$ or $Cl^-$ implying that none of these ions are involved in the folate transport cycle (data not shown).

G21 expression in human tissues and tumor cell lines. G21 mRNA levels were examined in a variety of human tissues by northern blotting (FIG. 6A). After hybridization followed by high stringency washes, two G21 mRNA forms were detected with molecular sizes of ~2.7 kb and 2.1 kb. The latter, short form, was dominant with a molecular size consistent with G21 mRNA in the NCBI database (2.096 kb, Genbank accession No. NM_080669). Substantial amounts of both G21 mRNA forms were detected in kidney, liver, placenta, small intestine, spleen and, to a lesser extent, in colon and testis. There was very low expression in brain, lung, stomach, heart and muscle. A smaller G21 transcript (~1 kb) was detected in brain, heart, kidney and an even smaller transcript was detected in liver (~0.5 kb). Quantitative RT-PCR was employed to further quantify G21 mRNA expression in intestine along with two human tumor cell lines (FIG. 6B). Expression in Caco2 cells, a colon carcinoma cell line, was >7 fold higher than in HeLa cells. In intestine, the highest level of mRNA expression was in duodenum, with lesser expression in jejunum and lower levels in ileum, cecum, segments of the colon, and rectum. Consistent with the northern blot, there was a high level of expression in liver.

The impact of suppression of G21 expression by interfering RNA on folate transport in human Caco2 cells. As indicated above, Caco2 cells have a very high level of G21 mRNA expression. To establish the extent to which constitutive low-pH folate transport activity in Caco2 cells could be attributed to this transporter, two shRNA vectors, targeted to two different regions of the G21 transcript, were stably co-transfected into Caco2 cells. This resulted in a 55% reduction in [$^3$H]folic acid influx at pH 5.5 and a similar (50%) decrease in G21 mRNA as quantified by RT-PCR (FIG. 6C). Wild-type Caco2 cells were subjected to transient transfection with siRNA duplex using the Amaxa system resulting in a 60% reduction in [$^3$H]MTX influx and a 50% decrease in G21 mRNA as compared to negative siRNA transfected cells (FIG. 6D). When the stably transfected Caco2 cells were also subjected to transient transfection with the Amaxa protocol there was a further suppression of G21 mRNA resulting in an 80% decrease in [$^3$H]MTX influx at pH 5.5 and a 75% decrease in G21 mRNA as compared to vector control-transfected cells (FIG. 6E). Taken together, these studies demonstrate that G21 is the major, and possibly the only, low-pH folate transporter in Caco2 cells.

An analysis of the role of G21 in the pathogenesis of hereditary folate malabsorption in a family with that disease. Hereditary folate malabsorption (OMIM 229050) is a rare recessive familial disorder characterized by signs and symptoms of folate deficiency that appear within a few months after birth. Infants exhibit low blood and cerebrospinal fluid folate levels with anemia, diarrhea, immune deficiency, infections and neurological deficits. There is a profound defect in intestinal folate absorption (Geller et al., 2002). To determine whether an alteration in G21 is the molecular basis for this disorder, blood was obtained from a family with progeny manifesting this disease that were the subject of a recent report (Geller et al., 2002; FIG. 7A). The mother and father were both normal, one of their children died in infancy, two of their other daughters displayed classical signs and symptoms of hereditary folate malabsorption. One daughter was diagnosed at the age of 8 months with a serum folate level of 0.2 nM (normal: 10-30 nM) and the other daughter was diagnosed at the age of 2 months with a blood folate level of less than 0.2 nM. Both children were treated with high doses of oral 5-FTHF with complete resolution of the signs and symptoms of their disease; they have developed normally and remain completely well on their folate supplement now at ages 9 and 6.

G21 is composed of 5 exons and 4 introns (FIG. 7B). Each of the five exons of G21 along with their flanking intron regions was sequenced from these family members. This revealed a homozygous mutation in gene 21 from both daughters and the same mutation in one allele of gene 21 from each parent (FIG. 7C). This G to A mutation (position 5882, GenBank accession number: DQ496103; SEQ ID NO:6) is located in the splice acceptor of intron 2 (intron 2/exon 3 boundary). To determine the consequences of this genomic mutation on RNA splicing, the exon 3 region of G21 mRNA was analyzed by RT-PCR from these family members. Two DNA fragments of 579 bp and 495 bp were detected from the parents transformed lymphocyte cDNAs, whereas only a single DNA fragment was detected from the daughters with a size identical to the shorter fragment from the parents. In comparison, the control cDNA from normal intestine exhibited a single amplified DNA fragment with a size identical to the longer DNA fragment from the parents (FIG. 7D). Subsequent DNA sequencing showed that the longer DNA fragment contained exon 3 whereas the shorter one did not. Hence, the single nucleotide mutation of G21 results in skipping of exon 3 and consequent in-frame deletion of 28 amino acids. Interestingly, the cDNA of this mutated transporter can be found in the GenBank (Accession number: BC010691), and appears to represent an alternatively spliced form (FIG. 7B). When transiently transfected into HeLa cells, this mutated G21 carrier lacked transport function based upon an analysis of (6S)5-MTHF uptake (FIG. 7E). Western blot analysis showed that the mutated G21 protein was less efficiently expressed and had a lower molecular weight than the wild-type protein when transiently transfected into HeLa cells (FIG. 7F). Further, immunofluorescence analysis indicated that when expressed in HeLa cells, the mutated G21 carrier was trapped intracellularly without detectable localization to the cell membrane (FIG. 7G). Thus, the parents carried both a functional wild-type, and the nonfunctional mutated, G21 mRNA and the daughters with the disease had only the nonfunctional mutated G21 mRNA. No mutation was detected in the reduced folate carrier mRNA amplified from the transformed lymphocyte cDNA from both daughters.

Discussion

These studies have identified G21, previously identified as HCP1 (SLC46A1), as a proton-coupled, electrogenic, folate transporter that has the properties of the low-pH folate transport activity associated with transport of folates in intestinal and other human cells—a high affinity for folic acid ($K_t$~0.6 µM), and a low affinity for the PT523 antifolate ($K_t$~>50 µM) at pH 5.5. This is in contrast to what is observed for the reduced folate carrier, a facilitative transporter (SLC19A1) ubiquitously expressed in human tissues. This carrier has low affinity for folic acid ($K_t$~200 µM), and high affinity for PT523 ($K_t$~0.7 µM), and a pH optimum of 7.4. The affinity of the reduced folate carrier for these folates, also in contrast to the low-pH transporter, does not change appreciably between pH 5.5 and 7.4 (Matherly and Goldman, 2003; Wang et al., 2004).

The identification of a loss-of-function mutation in HCP1 that results in the deletion of the third exon in a family with hereditary folate malabsorption, establishes that this gene is an intestinal transporter required for normal folate absorption and homeostasis. Accordingly, we amend the name of the transporter to PCFT. This takes into consideration the fact that this carrier is expressed in other tissues and may have functions beyond intestinal folate absorption. Consistent with the role of PCFT in intestinal absorption are the observations that: (1) PCFT mRNA is expressed in small intestine, particularly in the duodenum and, to a lesser extent in jejunum, segments that account for the bulk of folate absorption. These are areas in which the pH at the microenvironment of the intestinal surface is in the range of 6.0-6.2 (McEwan et al., 1990). (2) PCFT protein is localized to the apical brush border of intestinal cells (Shayeghi et al., 2005), (3) PCFT is highly expressed in Caco2 cells which manifests a high level of low-pH folate transport activity and have been used as a model for intestinal transport (Hidalgo et al., 1989), and (4) this constitutive folate transport activity in Caco2 cells can be nearly abolished (~80% suppression) by PCFT interfering RNA. The pH dependence of folate transport mediated by PCFT is consistent with studies in everted jejunal sacs and rings (Mason and Rosenberg, 1994). Quantitatively, in rat jejunum brush border membranes the uptake Km for folic acid increased from 0.6 µM at pH 5.5 to 12.3 µM at pH 7.4 and was competitively inhibited ($K_i$=1.4 µM) by racemic 5-MTHF (Mason et al., 1990; Selhub and Rosenberg, 1981). The identification of this carrier not only confirms the earlier conclusion that low-pH folate transport must be mediated by a mechanism genetically distinct from the reduced folate carrier, but also argues against an important role for the reduced folate carrier in intestinal folate absorption as has been proposed (Said, 2004). Hence, while the reduced folate carrier is expressed in the upper small intestine, its activity must be negligible since it cannot compensate for the loss of the PCFT in individuals with hereditary folate malabsorption under the acidic conditions of the absorptive surface. Likewise, the level of reduced folate carrier expression and function in the more alkaline distal small intestinal compartments is, apparently, insufficient to meet folate requirements at usual dietary folate levels. However, with the pharmacologic doses of 5-FTHF that are used to treat individuals with this disease (Geller et al., 2002), the route of delivery under these conditions may be by this mechanism.

This transporter was recently reported to be an intestinal heme carrier protein (HCP1). The murine ortholog was characterized as pH-independent over a range of 6.5 to 8.0 and with a Km of 125 µM for [$^{55}$Fe]hemin uptake in HeLa cells infected with a cDNA-containing adenovirus vector (Shayeghi et al., 2005). In that study, only a low level of transport activity was observed in Xenopus oocytes microinjected with the murine cRNA. Transporter mRNA was highly expressed in duodenum and protein was localized to the apical brush border membrane of murine intestinal cells. We found that hemin was an inhibitor of folic acid uptake into both Xenopus oocytes injected with PCFT cRNA and HepG2 cells stably transfected with this carrier. However, we were unable to detect a hemin-induced current in Xenopus oocytes expressing this transporter under conditions in which currents for the folate compounds were easily detectable. This implies that either there is no electrogenic hemin transport or that the $V_{max}$ for hemin transport must be more than an order of magnitude lower than that of folic acid. Based on the high affinity of this transporter for folates (~two orders of magnitude greater than the reported affinity for $^{55}$Fe-hemin), the high degree of specificity (including stereospecificity) for, and among folate/antifolate compounds, and the etiologic role of the mutated protein as the molecular basis for hereditary folate malabsorption, it is clear that the major physiological substrates for this transporter are folates. Further, the apparent complete correction of the hematological disorder with high doses of folates in individuals with hereditary folate malabsorption who lack both wild-type copies of this gene, argues against an important role of this carrier in the intestinal absorption of iron (Geller et al., 2002).

While PCFT operates most optimally at low pH, there is residual transport activity for 5-MTHF, the major blood folate (Opladen et al., 2006), at pH 7.4 suggesting that PCFT plays a role in the delivery of this folate to systemic cells under physiological conditions. Hence, the physiological importance of PCFT may extend to other organs in which PCFT mRNA is expressed, especially where transport activity at low pH has been documented, i.e. liver, which is a major folate storage site (Horne, 1993), but an acidic microenvironment is not present. From a pharmacological perspective, PCFT may play an important role in the delivery of antifolates into the acidic interior of solid tumors (Helmlinger et al., 1997; Wike-Hooley et al., 1984). The data in this paper, along with previous reports (Zhao et al., 2005b; Wang et al., 2004) suggest that transport of pemetrexed, a new-generation antifolate now in clinical use, would be especially favored in solid tumors because of its very high affinity for PCFT at acidic and neutral pH.

Besides its role in cellular transport, the PCFT may contribute to folate receptor-mediated endocytosis (Anderson et al., 1992). In this process, folate binds to glycosyl-phosphoinositol (GPI)-linked folate receptors at the cell surface which are internalized in endocytic vesicles. Within the cytoplasm, the vesicles acidify resulting in a marked transvesicular proton gradient. Acidification results in the dissociation of folate from the receptor and a strong driving force that would favor folate export from the vesicle via the PCFT (Murphy et al., 1984; Paulos et al., 2004). Similarly, PAT1-mediated export of amino acids from lysosomal vesicles in brain neurons has been proposed in addition to the role of this proton-coupled transporter in intestinal amino acid absorption (Boll et al., 2002; Sagne et al., 2001).

The identification of a molecular basis underlying folate transport mediated by a proton-coupled carrier offers a new dimension to the understanding of the physiology of folate transport, in particular, intestinal folate absorption and the mechanism of delivery of folates to peripheral tissues in which this activity is expressed. The molecular basis for hereditary folate malabsorption has been established. It is now possible to assess the role that alterations in this transporter might play in folate deficiency conditions. The observation that patients with this disease have no evidence of neural tube defects and that neurological deficits and other signs and symptoms appear months after birth implies that this gene is not absolutely required for delivery of folates to cells in the neural crest during embryonic neural tube formation. Rather, polymorphisms or mutations in this gene might contribute to maternal folate deficiency, especially in the developing world, compounding dietary folate deficiency, and thereby increasing the chances of neural tube defects in the developing embryo (Eichholzer et al., 2006). Indeed, the incidence of hereditary folate malabsorption may be greater than previously appreciated since most infants with this disorder in areas with endemic folate deficiency would be expected to die early in infancy, undiagnosed.

Experimental Procedures

Cell lines and cell culture conditions. HeLa, HepG2 and Caco2 cells were obtained from the American Type Tissue Collection (Manassas, Va.). HeLa, HeLa-R5 and HepG2 cells were maintained in RPMI 1640 medium. HeLa-R1 cells were maintained in the same medium at pH 6.9 in the presence of 500 nM MTX. Caco2 cells were grown in DMEM. All media were supplemented with 10% fetal bovine serum (Gemini Bio-Products, Calabasas, Calif.), 2 mM glutamine, 20 μM 2-mercaptoethanol, 100 units/ml penicillin, and 100 μg/ml streptomycin.

Reagents. [$^3$H]Folic acid, [$^3$H]MTX, [$^3$H](6S)5-FTHF, and [$^3$H](6S)5-MTHF were obtained from Moravek Biochemicals (Brea, Calif.) and purity monitored and maintained by HPLC. (6S)- and (6R)5-FTHF and (6S)5-MTHF were obtained from Schircks Laboratories (Jona, Switzerland). PT523, an antifolate analog, was a gift from Andre Rosowsky (Dana Farber Cancer Institute, Boston, Mass.). Folic acid, MTX, FCCP, hemin, estrone-3-sulfate, taurocholic acid, cholic acid, sulfobromophthalein, and para-amino hippurate were obtained from Sigma-Aldrich (St. Louis, Mo.). Hemin was dissolved in DMSO as a 5 mM stock solution. FCCP was dissolved in 95% ethanol to a concentration of 5 mM.

Database mining of the human genome. The Ensembl human peptide database was blasted with search sensitivity of Distant Homology using the conserved domains across species of the three SLC19 family members (Genbank accession No. pfam01770.12) and the human reduced folate carrier (Genbank accession No. NP_919231) as query. The predicted proteins, with similarity to SLC19 family transporters and unknown function, were chosen and used for subsequent screening of differential mRNA expression between HeLa-R5 and HeLa-R1 cells by RT-PCR.

Cloning and construction of G21. The open reading frame of G21 was amplified from cDNA of HeLa-R5 cells with pfuUltra DNA polymerase (Stratagene, Cedar Creek, Tex.) and primers which contain BglII restriction sites (underlined, Table 3), and subsequently cloned into the BglII site of the pSPT64 vector for synthesis of capped sense G21 cRNA from the SP6 promoter using the mMESSAGE mMACHINE system (Ambion, Austin, Tex.), and into the BamHI site of pcDNA3.1(+) to generate pcDNA3.1(+)G21.

TABLE 3

PCR primers for G21 open reading frame and quantitative RT-PCR

| | Primer sequence (5' to 3') |
|---|---|
| G21 open reading frame | Forward: TAT<u>AGATCT</u>CACCATGGAGGGGAGCGCGAGC (SEQ ID NO: 7)<br>Reverse: TAT<u>AGATCT</u>CAGGGGCTCTGGGGAAACTG (SEQ ID NO: 8) |
| Quantitative PCR | |
| Pair 1 for G21 | Forward: ATGCAGCTTTCTGCTTTGGT (SEQ ID NO: 9)<br>Reverse: GGAGCCACATAGAGCTGGAC (SEQ ID NO: 10) |
| Pair 2 for G21 | Forward: CTGTCATCCGGGCTAAACTC (SEQ ID NO: 11)<br>Reverse: AGGCCACAGCAGAAAAGAGA (SEQ ID NO: 12) |
| G3PDH | Forward: CGACCACTTTGTCAAGCTCA (SEQ ID NO: 13)<br>Reverse: CCCTGTTGCTGTAGCCAAAT (SEQ ID NO: 14) |
| β-actin | Forward: CGTGCTGCTGACCGAGC (SEQ ID NO: 15)<br>Reverse: GAAGGTCTCAAACATGATCTGGGT (SEQ ID NO: 16) |

Construction of G21 small hairpin RNA (shRNA). The Silencer Express (Human U6) kit (Ambion, Austin, Tex.) was used to produce shRNA expression cassettes (SECs) according to the manufacturer's protocol, which were screened by transient transfection into HeLa cells followed by measurement of MTX initial uptake and quantitative RT-PCR of G21 mRNA. The most effective SEC targeting G21 mRNA (1000-ACTAATCGGCTATGGTTCT-1020, GenBank accession number NM_080669) and the negative SEC were cloned into the pSEC hygromycin vector (Ambion). A commercial shRNA targeting G21 mRNA (841-CGATCCATTGTC-CAGCTCTAT-861) and a negative nonsilencing shRNA in a pSM2 retroviral vector were obtained from Open Biosystems (Huntsville, Ala.).

Transfection. Transfection of plasmid DNA was performed in HepG2, HeLa, and Caco2 cells with Lipofectamine 2000 (Invitrogen). HepG2 cells, stably transfected with either pcDNA3.1(+) or pcDNA3.1(+)G21, were generated by G418 selection (600 μg/ml). Double selection with puromycin (5 μg/ml) and hygromycin (50 μg/ml) was adopted to obtain stably transfected Caco-2 cells with both G21-silencing shRNA vectors, or with both non-silencing negative control plasmids.

Amaxa nucleofection of G21 small interfering RNA oligonucleotides. The Nucleofector™ II unit and the Nucleofector® cell line kit T (Amaxa Inc., Gaitherburg, Md.) were employed to nucleofect Caco-2 cells with SMARTpool® siRNA containing 4 different siRNA duplexes (Catalog #L-018653, Dharmacon, Inc., Lafayette, Colo.) which target G21 mRNA or siCONTROL non-targeting siRNAs (Catalog #D-001210-01, Dharmacon) which lack homology to any human gene. The nucleofected cells were assayed on day 3 post-seeding for initial [$^3$H]MTX uptake measurements and mRNA expression of G21 by quantitative RT-PCR.

Uptake studies in Xenopus oocytes. Defolliculated Xenopus laevis oocytes were prepared as described (Jansen and Akabas, 2006) and injected with 50 nl of water or G21 cRNA (30 ng). Radiotracer uptake was determined 3 or 4 days later. Seven to 10 oocytes were incubated in 500 µl of Modified Barth's Solution (MBS, in mM, 88 NaCl, 2.4 NaHCO$_3$, 2.5 Na pyruvate, 1 KCl, 0.82 MgSO$_4$, 0.41 CaCl$_2$, 0.3 Ca(NO$_3$)$_2$, 15 MES or HEPES) and uptake of tritiated folate substrates assessed at room temperature. Uptake was halted by the addition of ice-cold MBS (pH 7.5). Oocytes were washed 10 times thereafter, and solubilized with 10% SDS for measurement of radioactivity. To collapse the pH gradient across the oocyte membrane, seven to 10 oocytes were incubated in MBS (pH 5.5) containing 0, 10, 20, 40, 60 µM FCCP for 20 min, and uptake of transport substrates assessed at pH 5.5.

Transport of folates in HepG2, HeLa and Caco2 cells. Initial uptake of tritiated folates in HepG2, HeLa, or Caco2 cells was assessed using a protocol designed for rapid uptake determinations in cells growing in monolayer culture in liquid scintillation vials (Sharif and Goldman, 2000) except that cells were incubated at pH 7.4 and 37° C. for 20 min before initiation of uptake. Substrate uptake was normalized to protein content.

Electrophysiological analyses in Xenopus oocytes. Defolliculated oocytes were injected with 50 nl of water (control) or G21 cRNA (50 ng), and kept at 17° C. in horse serum medium (in mM, 82.5 NaCl, 2.5 KCl, 1 MgCl$_2$, 2.3 CaCl$_2$, 5 HEPES, 5% horse serum, pH 7.5). Electrophysiological recordings were conducted 3-7 days after cRNA injection in buffer (in mM, 90 NaCl, 1 KCl, 1 MgCl$_2$, 1.8 CaCl$_2$, 5 TRIS, 5 MES) as described previously (Jansen and Akabas, 2006). Oocyte holding potential was −80 mV for $K_m$ determination. For current-voltage (I-V) relationships, from a −60 mV holding potential step changes in membrane potential were applied for 2 s in 10 mV increments between −100 and 30 mV in the absence and presence of substrate.

Production of peptide antibody and immunofluorescence. To generate antisera to human G21 protein, a peptide ([C]ADPHLEFQQFPQSP) corresponding to amino acids 446-459 of this protein, was synthesized, conjugated with KLH, and injected into rabbits by Open Biosystems. The IgG fraction was isolated from the antiserum using a protein A-conjugated agarose column (Bio-Rad, Hercules, Calif.), and antibodies specific for G21 purified with the Sulfolink® Trial Kit (Pierce, Rockford, Ill.). Immunofluorescence was performed using affinity-purified anti-G21 and FITC-conjugated swine anti-rabbit antibody (Dako, Carpinteria, Calif.). HeLa cells were permeabilized with 0.2% Triton X-100 in phosphate buffer (PBS) at pH 7.4 for 15 min. The stained samples were mounted on slides with Vectashield mounting medium containing 1.5 µg/ml propidium iodide (Vecta Laboratories, Burlingame, Calif.).

SDS-PAGE and Western blotting. Water- and G21 cRNA-injected oocytes were homogenized in MBS with a protease inhibitor cocktail (Sigma-Aldrich). The homogenate was spun at 1000×g and 4° C. for 5 min to collect supernatant, the membrane fraction was pelleted by centrifugation at 13,200×g and 4° C. for 30 min and resuspended in MBS with protease inhibitors. To obtain HepG2 cell membranes, cells were incubated on ice for 30 min in hypotonic buffer (50 mM Na$_2$HPO$_4$, 1 mM EDTA, pH 7.4) containing protease inhibitors, following which the membrane fraction was pelleted by centrifugation at 13,200×g and 4° C. for 10 min, and resuspended in the same buffer. SDS-PAGE and protein blotting were conducted to detect G21 protein using rabbit anti-G21 antibody and secondary goat anti-rabbit IgG-horseradish peroxidase conjugate (Cell Signaling Technology, Danvers, Mass.).

Northern blotting. A Human PolyA+ Northern RNA blot containing polyA+ RNA (2 µg per lane) of 12 tissues (Origene, Rockville, Md.) was hybridized with $^{32}$P-dCTP-labelled cDNA probes from a G21 cDNA segment (97 bp-396 bp, Genbank accession No. NM_080669) overnight at 42° C. followed by four, 20 min high stringency washes at 65° C. β-actin mRNA was probed as the loading control.

Quantitative RT-PCR. cDNA was synthesized from DNase I-treated total RNA from HeLa, HeLa-R5, HeLa-R1 and Caco-2 cells with Superscript™ Reverse Transcriptase II (Invitrogen). cDNAs of the human digestive system were obtained from Clontech (Mountain View, Calif.). Real-time PCR was performed with SYBR® green PCR Master Mix (Applied Biosystems, Foster City, Calif.) and primers specific for G21 (Table 4). G3PDH or β-actin was simultaneously amplified with specific primers (Table 3) as house-keeping genes to normalize the G21 expression.

TABLE 4

PCR primers for genomic DNA and cDNA of G21 as well as RFC cDNA

| | Primer sequence (5' to 3') |
|---|---|
| Exons of G21[a] | |
| Exon 1 | Forward: TACGCACACTTTACAGGTGAGGTCATC (SEQ ID NO: 17)<br>Reverse: CCAAAATGCACCCTCCCTCCAGTTAC (SEQ ID NO: 18) |
| Exon 2 | Forward: TTCTCTGAGGTTTAGGGCTCCAAAGG (SEQ ID NO: 19)<br>Reverse: TAGTTGTCTGTTCTCCAGTGCAGGCT (SEQ ID NO: 20) |
| Exon 3 | Forward: TTCCTCCTTGACTACTGTCTTCCCAC (SEQ ID NO: 21)<br>Reverse: TCTGCTGACTGCAAATCCCAACTCTG (SEQ ID NO: 22) |
| Exon 4 | Forward: TAGCAGGATTTACTGGTGAGGAAGGG (SEQ ID NO: 23)<br>Reverse: TGCCAAGCAGCAATGTTAGCCTGATC (SEQ ID NO: 24) |
| Exon 5 | Forward: TATTGTCCTCCAGCTCTCAGCTTCTC (SEQ ID NO: 25)<br>Reverse: AAGGTTGCACAGCGAGTCAGTAGAAG (SEQ ID NO: 26) |

TABLE 4-continued

PCR primers for genomic DNA and cDNA of G21 as well as RFC cDNA

Primer sequence (5' to 3')

G21 cDNA[a]

Exon 3 region    Forward: CAGCTCAGCATCTCCCCTAC
                 (SEQ ID NO: 27)
                 Reverse: AAGAGAGCACTGCCCTTAGACAAG
                 (SEQ ID NO: 28)

RFC cDNA[b]

Full-length      Forward: CGTCACCTTCGTCCCCTCCG
                 (SEQ ID NO: 29)
ORF              Reverse: TAGCAGGATAAGCGGAGGCC
                 (SEQ ID NO: 30)

[a]PCR conditions are 35 cycles of 95° C. for 30 sec, 50° C. for 30 sec and 68° C. for 1 min.
[b]PCR conditions are 35 cycles of 95° C. for 45 sec, 60° C. for 45 sec and 72° C. for 1.5 min.

Analysis of G21 in a family with hereditary folate malabsorption. Members of a family with hereditary folate malabsorption were studied according to a protocol and Informed Consent in the subjects' native language approved by the Albert Einstein College of Medicine IRB (CCI#2006-279). Whole blood was used for isolation of genomic DNA by a Genomic DNA Purification Kit (Gentra Systems, Minneapolis, Minn.) and to generate EBV-transformed human B-lymphoblastoid cell lines in the Einstein Human Genetics Cell Culture Core. Each G21 exon with flanking regions was amplified using Taq DNA polymerase, Q-solution (Qiagen, Valencia, Calif.) and primers listed in Table 4. G21 or RFC cDNA were amplified from lymphoblastoid cells by RT-PCR. PCR products were gel-purified and sequenced in an ABI 3730 DNA Analyzer (Applied Biosystems). The mutated region was verified by sequencing both DNA strands. An expression vector of the mutated G21 in which exon 3 was skipped (GenBank accession number: BC010691) was purchased from Open Biosystems and, along with pcDNA3.1(+) G21 (wild type), was used for an assay of transport function. Western blot analysis on whole cell lysate and cellular localization was performed as described above.

Example 2

Mutations in the PCFT Gene Encoding an Intestinal Folate Transporter are the Basis for Hereditary Folate Malabsorption Example Summary Background. Hereditary folate malabsorption (HFM) is a rare autosomal recessive disorder caused by impaired intestinal folate absorption and impaired folate transport into the central nervous system. Infants present with anemia, hypoimmunoglobulinemia with severe infections, recurrent diarrhea and, often, neurological defects. Recent studies in one family established that the molecular basis for this disorder is a loss-of-function mutation in the PCFT gene encoding a proton-coupled folate transporter that mediates intestinal folate absorption. This gene was previously reported to encode a heme carrier protein, HCP1.

Methods. Five patients with HFM were identified for study, several of whom were subjects of previous case reports. PCFT was analyzed and the function of mutated carrier proteins was assessed by transient transfection into mammalian cells.

Results. Six different mutations in the PCFT gene were identified in five patients encompassing four of the five exons; five were homozygous, one was heterozygous and was traced back two generations. There was no racial, gender, or ethnic predilection. Four of the mutated transporters resulted in a complete loss of folate transport function, while two retained a low level of residual activity. Transformed lymphocytes from one family manifested a defect in folate transport at low pH. In three patients from two families, administration of high oral doses of leucovorin resulted in complete correction of their disorder.

CONCLUSIONS

Loss-of-function mutations in the PCFT gene are the molecular basis for HFM. Since HFM responds to treatment with parental or high oral doses of folate, it is important that physicians are aware of this disorder in infants with unexplained anemia, immune deficiency, and neurological deficits. The identification of the genetic basis for HFM will allow rapid diagnosis and treatment of this disorder in infants, and prenatal diagnosis in families that carry a mutant gene. The observation that provision of adequate folate to patients with HIFM fully corrects the abnormalities associated with disorder suggests that the contribution of PCFT to iron homeostasis is negligible or nonexistent.

Introduction

This Example focuses on the molecular pathogenesis of HFM that was recently shown, in one family, to be due to a mutation in a novel proton-coupled folate transporter (PCFT) that mediates intestinal folate absorption (Qiu et al., 2006, provided herewith as Example 1). PCFT has a low pH optimum that allows efficient transport of folates in the acid microclimate of the duodenum and jejunum, the major sites of folate absorption, where this transporter is highly expressed (McEwan et al., 1990). This same gene was recently reported to be a heme carrier protein (HCP1), that mediates heme-iron absorption (Sheyeghi et al., 2005), but its major function appears to be folate transport (Qiu et al., 2006).

The objective of this study was to extend the understanding of the spectrum of genomic alterations in PCFT gene that are the basis for HFM along with an analysis of the functional properties of the protein in five additional families with this disease, two of whom were the subject of case reports prior to the characterization of the underlying genetic defect (Corbeel et al., 1985; Malatack et al., 1999). In one family, the genetic defect was traced through three generations.

Materials and Methods

Patients. Patient P1 is a male child of two African-American parents who denied consanguinity. He presented at age 3 months with pancytopenia, a megaloblastic marrow, hypoimmunoglobulinemia, and *Pneumocystis carinii* pneumonia. He is mentally retarded and has a seizure disorder and has been treated with parental 5-formylTHF. This patient was the subject of a previous case report (Malatack et al., 1999).

Patient P2 was also the subject of a prior case report (Corbeel et al., 1985) and was the 9th child (female) of Turkish parents who denied consanguinity. She presented at five months of age with a history of fever, diarrhea and convulsions. She was anemic, leukopenic, with a megaloblastic bone marrow and hypoimmunoglobulinemia. Despite treatment with parental folate she had chronic seizures, persistent neurological defects including hemiplegia and mental retardation.

The third child (P3-female) is of European ancestry and presented in infancy with a folate responsive megaloblastic anemia, and a developmental delay in speech receptive language and fine motor skills. The parents were second cousins.

The fourth patient (P4-female) is an Arab child from Israel who presented at the age of 4 months with anemia, diarrhea, and failure to thrive. Another member of her family had been diagnosed with folic acid malabsorption.

The fifth patient, of Latino origin, (P5-male) presented in October 2005 at the age of 4 months with severe anemia. He subsequently developed *Pneumocystis carinii* pneumonia. The child had a sister who developed pancytopenia at age 3 months and died due to cytomegalovirus pneumonia. In the hospital, the patient's Hb fell to a low of 5.5 gm %; matricies and hypersegmented neutrophils were noted and the bone marrow was megaloblastic. There was a falling platelet count that reached a nadir of 44,000/mm$^3$. The patient's serum folate was <0.4 ng/ml (nl>2.8). Serum immunoglobulins were low: IgG-134 mg/dl (nl, 700-1600), IgA-13 mg/dl (nl, 70-400 mg/dl), and IgM-8 mg/dl (nl, 40-230 mg/dl). The patient was treated with IV folate then subsequently placed on oral 5-formylTHF (formyltetrahydrofolate). The pneumonia was treated successfully and the patient had a rapid onset of reticulocytosis, his hemogram normalized, and the pneumonia resolved. He was subsequently maintained on an oral dose of 10 mg of 5-formylTHF b.i.d. He is currently developing normally with a Hb of 12.5 g/dl, Hct of 37%, WBC of 10.6/mm$^3$ and platelets of 371/mm$^3$ with a blood folate level of 5.33 ng/ml. Blood was also obtained for analysis from the child's parents and grandparents.

Patients six (P6) and seven (P7) were female siblings, diagnosed and treated in infancy, that were the subject of a previous case report (Geller et al., 2002) and studies that established a mutation in PCFT as the basis for HFM (qiu et al., 2006). One of the siblings is on 200 mg of oral 5-formylTHF/d and currently has a Hb of 13.9 g/dl, HCT of 42.4%, WBC of 8.4/mm$^3$, platelets of 297 K/mm$^3$, and a serum ferritin of 54 ng/ml (nl, 10-105). The other sibling, on 150 mg of oral 5-formylTHF/d has a Hb of 12.8 g/dl, HCT of 39.5%, WBC of 8.3/mm$^3$, platelets of 189/mm$^3$, serum Fe of 92 µg/dl (nl, 40-190), TIBC of 253 µg/dl (nl, 250-400), and ferritin of 97 ng/ml. These patients, now at ages 6 and 9 have developed normally.

Cell lines and chemicals. HeLa cells were maintained in RPMI-1640 medium supplemented with 10% fetal bovine serum, 100 units/ml penicillin and 100 µg/ml streptomycin. The natural 6S isomer of tritiated 5-methyltetrahydrofolate ([$^3$H]5-methylTHF) was obtained from Moravek Biochemicals (Brea, Calif.); unlabeled (6S)5-methylTHF was purchased from Schircks Laboratories (Jona, Switzerland).

Identification of mutations in PCFT gene. This study and the associated Informed Consent were approved by Albert Einstein College of Medicine IRB (CCI#2006-279). Blood was obtained from patients with the clinical diagnosis of HFM (P1-P7) and from their relatives (P5, P6, P7) and genomic DNA was extracted by the Gentra Systems purification Kit (Minneapolis, Minn.). For three HFM patients (P2, P3, P4), genomic DNA was obtained from their fibroblasts. The primers and conditions for genomic PCR were reported previously 5. PCFT DNA fragments were purified from agarose gel and sequenced on an ABI 3730 DNA analyzer. When required, the mutated regions were sequenced with both sense and antisense primers.

Site-directed mutagenesis. PCFT cDNA was cloned in pCDNA 3.1 (+) and mutations in the coding region were introduced by site-directed mutagenesis using PfuTurbo® DNA polymerase (Stratagene, La Jolla, Calif.) as described previously (Zhao et al., 2000). The entire PCFT coding region in the plasmid was sequenced to verify the presence of the mutation.

Transient transfections and assessment of 5-methylTHF transport. Plasmid concentrations were determined by UV absorption and verified by agarose gel analysis. HeLa cells were seeded and transiently transfected in 20 ml glass scintillation vials (Research Products International Corp., Mt. Prospect, Ill.) and after two days, [$^3$H]5-methylTHF uptake was assessed (Qiu et al., 2006). EBV-transformed B-lymphoblastoid cells, generated from blood (P6 and P7), were washed twice with, and resuspended in, unbuffered saline (160 mM NaCl, 5 mM KCl, 2 mM MgCl$_2$, 5 mM glucose). Uptake was initiated by injection of the cell suspension into MES-buffered saline (pH 5.5) containing 0.5 µM [$^3$H]5-methylTHF. Surface binding was assessed by measuring [$^3$H]5-methylTHF associated with cells at 0° C. and the bound component was subtracted from total uptake.

Results

Identification of mutations in the PCFT. A single homozygous mutation was identified in patients P1, P2, P3 and P4 while two different mutations were identified in patient P5 (Table 5). Except for a "G" deletion found in P1, all mutations were base substitutions. Whereas the deletion of a "G" resulted in a truncated protein that ends after 88 amino acids due to a frame shift at position 65, all base substitutions resulted in point mutations in PCFT (Table 5). In patient P5, c. 1126C>T was detected in the father and paternal grandfather, and c.954C>G was detected in the mother and maternal grandfather (FIG. 10C). No PCFT mutations were found in the maternal and paternal grandmothers. The genomic locations of these mutations are indicated in FIG. 10A and the amino acids affected are depicted in the predicted secondary structure of the transporter in FIG. 10B.

TABLE 5

PCFT mutations identified in patients with HFM and the resultant changes in protein composition

| Patient | Nucleotide change[a] | Amino acid changes |
|---|---|---|
| 1 | c.194delG[b] | p.G65AfsX25 |
| 2 | c.337C > A | p.R113S |
| 3 | c.439G > C | p.G147R |
| 4 | c.1274C > G | p.P425R |
| 5 | c.954C > G | p.S318R |
|   | c.1126C > T | p.R376W |
| 6, 7[c] | c.1082-1G > A | p.Y362__G389del |

[a]The mutations are described according to the nomenclature derived by the Human Genome Variation Society (http://www.hgvs.org/mutnomen).
[b]Genbank reference sequence, NM_080669. The cDNA is numbered from the initiation codon.
[c]Since there is a span of seven G's from position 188-194, the deleted G was arbitrarily assigned to the last G or G194.
[d]The PCFT mutation in this family was recently reported (Qiu et al., 2006).

Assessment of the function of PCFT mutants. Nucleotide changes corresponding to the wild-type and mutant proteins were individually introduced into a PCFT expression vector by site-directed mutagenesis and then transiently transfected into HeLa cells. [$^3$H](6S)5-methylTHF, the physiological blood folate in humans, was used as the transport substrate. As indicated in FIG. 11, while HeLa cells transfected with the wild-type transporter cDNA demonstrated high levels of 5-methylTHF uptake at pH 5.5, there was essentially no uptake detected in cells transfected with the cDNA of R113S, G65fsX25, S318R and R376L. There was, however, a low but statistically significant level of residual transport activity, (7.0% and 3.4% for the G147R and P425R mutants, respectively), as compared to the wild-type transporter when the background activity of mock-transfected cells was subtracted.

Transformed lymphocytes were available for analysis of [$^3$H]5-methylTHF transport from the father, mother, and two affected daughters (P6 and P7) in the initial report (Qiu et al., 2006). It can be seen that transport into the daughter's lymphocytes was ¼ to ⅕ the rate of transport into the parents lymphocytes at pH 5.5 (FIG. 12). Since both parents carry one mutated non-functional allele, the transport rate in their lymphocytes would be expected be one-half the level if both alleles were wild-type. Hence, the degree of loss of transport activity noted in the daughter's lymphocytes would be much lower if compared to transport into cells that contain two wild-type PCFT alleles.

Discussion

HFM was first described in 1961 (Lubhy et al., 1961) and since then there have been 12 reported families with this disorder (Geller et al., 2002; Jebnoun et al., 2001). The molecular basis for HFM in one family in which two children were affected (P6 and P7) was subsequently shown to be due to a mutation in a novel proton-coupled folate transporter, PCFT, a member of the family of solute carriers, (SLC46A1) (Qiu et al., 2006). In that family, the mutation occurred in an intron splice acceptor site resulting in deletion of the third exon and a smaller transcript, a known splice-variant, coding for a protein that is not functional. This report extends the understanding of the genetic basis of HFM to five additional patients with this disease, from five different families. There was no consistent racial, ethnic, or gender pattern in this group; families were of Latino, African-American, Turkish, Arabic and European origin.

A single loss-of-function mutation was identified in each of four patients which represented either a homo- or hemizygous alteration. In a fifth patient each PCFT allele carried a different mutation that could be traced back two generations. There did not appear to be any specific "hot-spot" for mutations in the PCFT gene associated with HFM; mutations were found in four of the five exons. All the point mutations were at highly conserved residues and resulted in substitutions of amino acids with different charge. In two cases there were some residual transport activity mediated by the mutant carrier but there was insufficient information to relate this to the severity of the disease or the amount of folate required for treatment. In two sisters, previously reported (Geller et al., 2000; Qiu et al., 2006), a marked transport defect was demonstrated in their transformed lymphocytes at the low pH optimum of the PCFT carrier.

In addition to impaired intestinal folate absorption, patients with HFM have a defect in the transport of folates into the central nervous system (CNS). The CSF:blood folate ratio in normal subjects is 3:1. In HFM, CSF folate is very low or not detectable. In HFM subjects, it is only when blood folate levels are above normal that CSF folate concentrations rise to the normal range (Geller et al., 2000). Folates are actively transported across the blood brain barrier and the choroid plexus (Wu and Pardridge, 1999; Spector and Lorenzo, 1975). Folate receptor alpha (FRα—an endocytic process) and the reduced folate carrier (RFC—an anion exchanger) are expressed in the choroid plexus (Holm et al., 1991; Wang et al., 2001). PCFT is also expressed in brain and in the choroid plexus (unpublished); however, because the pH at these sites is physiological, the activity of this gene under these conditions would be very low. FRα appears to play an important role in the delivery of folates to the brain since autoantibodies to this receptor are associated with cerebral folate deficiency, a disorder in which blood folate levels are normal, but CSF folate is very low (Ramaekers et al., 2005). The defect in transport of folates into the brain and CSF in HFM indicates that PCFT also plays a critical role in this process. This may be due to its requirement for folate receptor function. Hence, in the endocytic process mediated by FRα, folate bound to the receptor is internalized in vesicles that traffic intact within the cytoplasm where the vesicles acidify and folate is released from the receptor. The mechanism of folate export from the vesicle has not been clarified but may be mediated by PCFT propelled by the high transvesicular pH gradient, as suggested previously (Qiu et al., 2006; Prasad et al., 1994). This has been proposed for the dual function of proton-coupled intestinal absorption and lysosomal transport of the amino acid transporter PAT1 (Boll et al., 2004; Sagne et al., 2001).

The mechanism by which therapeutic doses of folates are absorbed in subjects with mutated PCFT is uncertain. If the kinetic change in the mutated PCFT is due to a decreased affinity for folates, and there is some retention of residual activity, as occurs with the G147R and P425R variants, high oral doses could achieve sufficient intestinal absorption to meet the requirements for this vitamin. Also, since RFC is expressed along the entire small intestine, with sufficient folate intake some absorption may occur within the unfavorable acid environment of the upper small intestine. Alternatively, the delivery of high levels of folate to distal alkaline areas of the small intestine could result in folate absorption via RFC, which operates most efficiently at physiological pH. This notion is consistent with the observation that RFC expression in intestine is upregulated when mice are fed a folate-deficient diet (Said et al., 2000; Liu et al., 2005). In this regard, the active isomers of 5-formylTHF (leucovorin) or 5-methylTHF (metafolin) would be the preferred forms of folate since their affinity for RFC is more than two orders of magnitude greater than the affinity of folic acid for this transporter (Matherly and Goldman, 2003).

PCFT was recently identified as a heme carrier protein (HCP1) (Shayeghi et al., 2005). However, the affinity of this transporter for hemin is about two orders of magnitude lower than its affinity for folates, and while folate transport mediated by PCFT is both electrogenic and proton-coupled, uptake of hemin is not (Shayeghi et al., 2005). Further, the anemia of HFM, along with the other signs and symptoms of this disorder, can be corrected by the administration of folate alone, rendering patients normal, without any evidence of iron deficiency. Hence, it is unlikely that this transporter plays an important role in the intestinal absorption of iron or makes a significant contribution to iron homeostasis or the utilization of iron by hematopoietic cells.

With the identification of the mechanism of intestinal folate absorption it will be important to determine the prevalence of mutations or polymorphisms in PCFT that may account for variations in folate status among individuals. It does not appear that this gene is required for embryonic neural tube development since patients with HFM have not been reported to have spina bifida. However, alterations in the PCFT gene could contribute to abnormalities in the mother's folate status during pregnancy, especially when folate intake is low or marginal, so that defects in expression or function of this gene could, on this basis, be a contributing factor to neural tube defects in the developing embryo. In any event, the identification of mutations in PCFT as the basis for HFM will allow rapid diagnosis and treatment of this disease in infants, and prenatal diagnosis in families that carry a mutant gene.

REFERENCES

Anderson, R. G. W., Kamen, B. A., Rothberg, K. G., and Lacey, S. W. (1992). Potocytosis: sequestration and transport of small molecules by caveolae. Science 255, 410-411.

Benz, R. and McLaughlin, S. (1983). The molecular mechanism of action of the proton ionophore FCCP (carbonylcyanide p-trifluoromethoxyphenylhydrazone). Biophys. J. 41, 381-398.

Boll, M., Foltz, M., Rubio-Aliaga, I., Kottra, G., and Daniel, H. (2002). Functional characterization of two novel mammalian electrogenic proton-dependent amino acid cotransporters. J. Biol. Chem. 277, 22966-22973.

Boll M, Daniel H, Gasnier B. (2004). The SLC36 family: proton-coupled transporters for the absorption of selected amino acids from extracellular and intracellular proteolysis. Pflugers Arch 447, 776-779.

Corbeel L, Van den B G, Jaeken J, Van Tornout J, Eeckels R. (1985). Congenital folate malabsorption. Eur J Pediatr 143, 284-290.

Eichholzer, M., Tonz, O., and Zimmermann, R. (2006). Folic acid: a public-health challenge. Lancet. 367, 1352-1361.

Geller, J., Kronn, D., Jayabose, S., and Sandoval, C. (2002). Hereditary folate malabsorption: family report and review of the literature. Medicine (Baltimore). 81, 51-68.

Hagenbuch, B. and Meier, P. J. (2003). The superfamily of organic anion transporting polypeptides. Biochim. Biophys. Acta 1609, 1-18.

Helmlinger, G., Yuan, F., Dellian, M., and Jain, R. K. (1997). Interstitial pH and pO2 gradients in solid tumors in vivo: high-resolution measurements reveal a lack of correlation. Nat. Med. 3, 177-182.

Hidalgo, I. J., Raub, T. J., and Borchardt, R. T. (1989). Characterization of the human colon carcinoma cell line (Caco-2) as a model system for intestinal epithelial permeability. Gastroenterology. 96, 736-749.

Holm J, Hansen S I, Hoier-Madsen M, Bostad L. (1989). High-affinity folate binding in human choroid plexus. Characterization of radioligand binding, immunoreactivity, molecular heterogeneity and hydrophobic domain of the binding protein. Biochem J 280, 267-271.

Horne, D. W. (1993). Transport of folates and antifolates in liver. Proc. Soc. Exp. Biol. Med. 202, 385-391.

Jansen, M. and Akabas, M. H. (2006). State-dependent cross-linking of the M2 and M3 segments: functional basis for the alignment of GABAA and acetylcholine receptor M3 segments. J. Neurosci. 26, 4492-4499.

Jebnoun S, Kacem S, Mokrani C H, Chabchoub A, Khrouf N, Zittoun J. (2001). A family study of congenital malabsorption of folate. J Inherit Metab Dis 24, 749-750.

Koepsell, H. and Endou, H. (2004). The SLC22 drug transporter family. Pflugers Arch. 447, 666-676.

Liu, M, Ge Y, Cabelof D C, Aboukameel A, Heydari A R, Mohammad R et al. (2004) Structure and regulation of the murine reduced folate carrier gene: identification of four noncoding exons and promoters and regulation by dietary folates. J Biol Chem 280, 5588-5597.

Lubhy A L, Eagle F J, Roth E, Cooperman J M. (1961). Relapsing megaloblastic anemia in an infant due to a specific defect in gastraointestinal absorption of folic acid. Am J Dis Child 102, 482-483.

Malatack J J, Moran M M, Moughan B. (1999). Isolated congenital malabsorption of folic acid in a male infant: insights into treatment and mechanism of defect. Pediatrics 104, 1133-1137.

Mason, J. B. and Rosenberg, I. H. (1994). Intestinal absorption of folate. In Physiology of the gastrointestinal tract, L. R. Johnson, ed. (New York: Raven Press), pp. 1979-1995.

Mason, J. B., Shoda, R., Haskell, M., Selhub, J., and Rosenberg, I. H. (1990). Carrier affinity as a mechanism for the pH-dependence of folate transport in the small intestine. Biochim. Biophys. Acta Bio-Membr. 1024, 331-335.

Matherly, L. H. and Goldman, D. I. (2003). Membrane transport of folates. Vitam. Horm. 66, 403-456.

McEwan, G. T., Lucas, M. L., Denvir, M., Raj, M., McColl, K. E., Russell, R. I., and Mathan, V. I. (1990). A combined TDDA-PVC pH and reference electrode for use in the upper small intestine. J. Med. Eng Technol. 14, 16-20.

Murphy, R. F., Powers, S., and Cantor, C. R. (1984). Endosome pH measured in single cells by dual fluorescence flow cytometry: rapid acidification of insulin to pH 6. J. Cell Biol. 98, 1757-1762.

Opladen, T., Ramaekers, V. T., Heimann, G., and Blau, N. (2006). Analysis of 5-methyltetrahydrofolate in serum of healthy children. Mol. Genet. Metab. 87, 61-65.

Paulos, C. M., Reddy, J. A., Leamon, C. P., Turk, M. J., and Low, P. S. (2004). Ligand binding and kinetics of folate receptor recycling in vivo: impact on receptor-mediated drug delivery. Mol. Pharmacol. 66, 1406-1414.

Poncz M, Cohen A. (1996). Long-term treatment of congenital folate malabsorption. J Pediatr 129, 948.

Prasad P D, Mahesh V B, Leibach F H, Ganapathy V. (1994). Functional coupling between a bafilomycin Al-sensitive proton pump and a probenecid-sensitive folate transporter in human placental choriocarcinoma cells. Biochim Biophys Acta Mol Cell Res 1222, 309-314.

Qiu A, Jansen M, Sakaris A, Min S H, Chattopadhyay S, Tsai E et al. (2006). Identification of an intestinal folate transporter and the molecular basis for hereditary folate malabsorption. Cell 127, 917-928.

Ramaekers V T, Rothenberg S P, Sequeira J M, Opladen T, Blau N, Quadros E V et al. (2005). Autoantibodies to folate receptors in the cerebral folate deficiency syndrome. N Engl J Med 352, 1985-1991.

Spector R, Lorenzo A V. Folate transport in the central nervous system. (1975). Am J Physiol 229, 777-782.

Sagne, C., Agulhon, C., Ravassard, P., Darmon, M., Hamon, M., El Mestikawy, S., Gasnier, B., and Giros, B. (2001). Identification and characterization of a lysosomal transporter for small neutral amino acids. Proc. Natl. Acad. Sci. U. S. A. 98, 7206-7211.

Said, H. M. (2004). Recent advances in carrier-mediated intestinal absorption of water-soluble vitamins. Annu. Rev. Physiol. 66, 419-446.

Said H M, Chatterjee N, Haq R U, Subramanian V S, Ortiz A, Matherly L H et al. (2000). Adaptive regulation of intestinal folate uptake: effect of dietary folate deficiency. Am J Physiol Cell Physiol 279, C1889-C1895.

Selhub, J. and Rosenberg, I. H. (1981). Folate transport in isolated brush border membrane vesicles from rat intestine. J. Biol. Chem. 256, 4489-4493.

Sharif, K. A. and Goldman, I. D. (2000). Rapid determination of membrane transport parameters in adherent cells. BioTechniques 28, 926-8, 930, 932.

Shayeghi, M., Latunde-Dada, G. O., Oakhill, J. S., Laftah, A. H., Takeuchi, K., Halliday, N., Khan, Y., Warley, A., McCann, F. E., Hider, R. C., Frazer, D. M., Anderson, G. J., Vulpe, C. D., Simpson, R. J., and McKie, A. T. (2005). Identification of an intestinal heme transporter. Cell. 122, 789-801.

Stover, P. J. (2004). Physiology of folate and vitamin B12 in health and disease. Nutr. Rev. 62, S3-12.

Wang Y, Zhao R, Russell R G, Goldman I D. (2001). Localization of the murine reduced folate carrier as assessed by immunohistochemical analysis. Biochim Biophys Acta 1513, 49-54.

Wang, Y., Rajgopal, A., Goldman, I. D., and Zhao, R. (2005). Preservation of folate transport activity with a low-pH optimum in rat EC-6 intestinal epithelial cell lines that lack reduced folate carrier function. Am. J. Physiol Cell Physiol 288, C65-C71.

Wang, Y., Zhao, R., and Goldman, I. D. (2004). Characterization of a folate transporter in HeLa cells with a low pH optimum and high affinity for pemetrexed distinct from the reduced folate carrier. Clin. Cancer Res. 10, 6256-6264.

Wike-Hooley, J. L., Haveman, J., and Reinhold, H. S. (1984). The relevance of tumour pH to the treatment of malignant disease. Radiother. Oncol. 2, 343-366.

Wu D, Pardridge W M. (1999). Blood-brain barrier transport of reduced folic acid. Pharm Res 16, 415-419.

Zhao R, Gao F, Wang P J, Goldman I D (2000). Role of the amino acid 45 residue in reduced folate carrier function and ion-dependent transport as characterized by site-directed mutagenesis. Mol Pharmacol 57, 317-323.

Zhao, R., Chattopadhyay, S., Hanscom, M., and Goldman, I. D. (2004a). Antifolate resistance in a HeLa cell line associated with impaired transport independent of the reduced folate carrier. Clin. Cancer Res. 10, 8735-8742.

Zhao, R., Gao, F., Hanscom, M., and Goldman, I. D. (2004). A prominent low-pH methotrexate transport activity in human solid tumor cells: Contribution to the preservation of methotrexate pharmacological activity in HeLa cells lacking the reduced folate carrier. Clin. Cancer Res. 10, 718-727.

Zhao, R., Hanscom, M., and Goldman, I. D. (2005b). The relationship between folate transport activity at low pH and reduced folate carrier function in human Huh7 hepatoma cells. Biochim. Biophys. Acta. 1715, 57-64.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NOs

SEQ ID NO: 1 - human full length PCFT cDNA (G21 clone), GenBank NM_080669

```
   1 acagcgcaag ccccacgcca cgcgtcgctg gtcccaggca gcgagtcgct cgcgcgcccc
  61 gccgcccgcc tggcgacagc tccgccgcgc acgcacatgg aggggagcgc gagcccccg
 121 gaaaagcccc gcgcccgccc tgcggctgcc gtgctgtgcc ggggcccggt agagccgctg
 181 gtcttcctgg ccaactttgc cttggtcctg cagggcccgc tcaccacgca gtatctgtgg
 241 caccgcttca gcgccgacct cggctacaat ggcacccgcc aaaggggggg ctgcagcaac
 301 cgcagcgcgg accccaccat gcaggaagtg gagaccctta cctcccactg gaccctctac
 361 atgaacgtgg gcggcttcct ggtggggctc ttctcgtcca ccctgctggg agcttggagc
 421 gacagtgtgg gccgccgccc gctgctagtg ctggcctcgc tgggcctgct gctccaggcc
 481 ctagtgtccg tttttgtggt gacgctgcag ctccacgtcg gctacttcgt gctgggtcgc
 541 atcctttgtg ccctcctcgg cgacttcggt ggccttctgg ctgctagctt tgcgtccgtg
 601 gcagatgtca gctccagtcg cagccgcacc ttccggatgg ccctgctgga agccagcatc
 661 ggggtggctg ggatgctggc aagcctcctc ggggggccact ggctccgggc ccagggttat
 721 gccaacccct tctggctggc cttggccttg ctgatagcca tgactctcta tgcagctttc
 781 tgctttggtg agaccttaaa ggagccaaag tccaccccggc tcttcacgtt ccgtcaccac
 841 cgatccattg tccagctcta tgtggctccc gcccagaga agtccaggaa acatttagcc
 901 ctctactcac tggccatctt cgtggtgatc actgtgcact ttggggccca ggacatctta
 961 accctttatg aactaagcac accctctgc tgggactcca aactaatcgg ctatggttct
1021 gcagctcagc atctccccta cctcaccagc ctgctggccc tgaagctcct gcagtactgc
1081 ctggccgatg cctgggtagc tgagatcggc ctggccttca acatcctggg gatggtggtc
1141 tttgcctttg ccactatcac gcctctcatg ttcacaggat atgggttgct tttcctgtca
1201 ttagtcatca cacctgtcat ccgggctaaa ctctccaagc tggtgagaga gacagagcag
1261 ggtgctctct tttctgctgt ggcctgtgtg aatagcctgg ccatgctgac ggcctccggc
1321 atcttcaact cactctaccc agccactctg aactttatga aggggttccc cttcctcctg
1381 ggagctggcc tcctgctcat cccggctgtt ctgattggga tgctggaaaa ggctgatcct
1441 cacctcgagt tccagcagtt tccccagagc ccctgatctg cctgaccag aagacagagg
1501 gcaagaggag caaagtgaac accaagcaac tggaggtctg cagctggaag cccagcccac
1561 agcaggacaa gcaactcttg tctaagggca gtgctctctt tggacgaggt agtcaagaga
1621 gaccaaggca ccacccatc cacagctgac ccagcctctg tctaggatct agaatcataa
1681 cccacacagg cccactgcag gacaggtggc agaggagcta tttgggacag gagtcagttc
1741 tcccttctg ctatccatca cttataaccc cacaggccag aggagaggtc ctgagagagg
1801 tgacacttca gggaccagag gcagcacgag ggctggcatc tctccttcca gcccaaactg
1861 cacagcccca accaggttcc caacacgtgt agcagtcatc agccattcct taacaatgaa
1921 tgtggtacct ggttagtgcc agccttggga aggagggagg gaggtaagag gggcttggtg
1981 atctctggag gaagatgtt ggtttgggga atcgatcctt ggctatggcc
2041 tacccactcc cctggctgaa gagtgccaat cattacaaat cagcttcagc aaactgaaac
2101 aaaccttctg gtgccttggg ctttggggcc ctctgttttc ctgctcccag tctgcctgcc
2161 atacgttaga caacagaagc tgctgggctg ggcaggagcc ctgagctgcc tggtggattg
2221 gtaccaagtg gggccagcca gggcttctac tgactcgctg tgcaaccttg agcaagcccc
2281 actaggaacg gctagatcag caatgcccca aattgttgaa tcgtggtgat cacatttgga
```

APPENDIX-continued

SEQ ID NOs

```
2341 tggacaagtt aggaaactta gctgattctc tgagatactt cccacttcct catacattct
2401 acaatgagat gcctctcttc atgggcctgg ggaaaggatg aatgagtgtg gctggacttt
2461 tgacctttaa tgtccctgag cagttcttgg cccttgggga gaagtagggg gaggatctgg
2521 ctgactcagc cccaaccgag gggtagcagc tgcagcccag ccaagcagaa caccctggcc
2581 ctacagacct gtgtctgagc aggctttgga ggaaaggcca cttctgagtc tctgtctca
2641 ggagaagcca ggcctaggtg cttgacctgg tgatctgagc tgtgtttgtc ctagtatggg
2701 tggcagtcac ctctgaacac actggcctg gcttagagga ggcttgtgac ttcagctgtt
2761 ccagctgggg ctggatgctg gactctgatt ccctcagaga gacagaagat cgggcagagg
2821 tcaaccagaa ggccacacag ggcagtggac aacagtggag ggtataccaa atagaaataa
2881 aacgcaggaa acctctctga atactgccct tggggaccct aggagggagt gggactgatt
2941 ggagacaaag agccagaaat catccctgg agatactcag acactgtatt gttattggcg
3001 ctgtcctgtg agggcagtgt ccaggctgcc ctgcttgtca tatccatgcc ctggctctgg
3061 ccccgtgag cacttgtgct gcatgaggaa aggaggatca ggtggggtca aaaccaaagc
3121 atcgaggctg gcactggcca agacagactc tggcagggag gggagtggaa ggaaggagcc
3181 ccaaacctgg agtgagacct ttgactttct gatgatgtgg ccaagaacta ggagtcacct
3241 ggccagcaca gccaagagtg gggctggggg cgccagcttt aaggtgtcaa cacctggccc
3301 ttgcgggaa agagccttca gcagccccca cggcctggag cctgggttta ttggagggtg
3361 ctttcttacc ctctgaaccc agtggaggag ggggcaatgg gatattcctg ctctgtatgg
3421 cctctgggtc agcttttttgt tgcaaaatcc tatccccgc tgctagattc tttgaagcaa
3481 gggagaagca atagcccagc ctcagaatga ttctcaggaa agcaattcca ctgccagtgg
3541 actgggtgcc aggaggccta ggtctggatc tggggctgcc actaatgaca ggaaagtggg
3601 cttatcctca acctttctga gcctcagtgt cattatctgt aaaatgggga tgataatacc
3661 aggtagagtt gctctgatga ctggagacca tggagcggag tgttttgggaa atggcaaaga
3721 tttgtgaggg cttcgtgctt tagagatttg ctacccttaa ccaccagcat cagctcacct
3781 gggaatctgt aagaaatgca gagtcctagg ccccacccca gatctcctga ttttaacaac
3841 attcccaggt gacttggatg catgttaaag ttggagaagc tgccctaagt gacaaccctt
3901 tgcctttttca ggactttgcc tctttccaca gagctgcagg ttctgtctag gctgctttta
3961 ctgccatggg ggctgcctgg tccctgagta agcagtgggt agccctggat ggctgagggg
4021 ctggggaagc cagctgggcc agaccaggaa ggagcctgag gcacagcacc aaggcatggg
4081 gtagggtggg ctttgaggca cggcctcccc atgcccagac ccaggcccaa acaggaggct
4141 cctgtgcacc agcaagtgca gcaaagctgg ctgcagtgac aaggaagtca gagggagggc
4201 tggtttgcct caaccctcgc cctggatgtg gcaaaagata ccacaccgaa ggaagctgta
4261 ggggatctgg gacttagtca ggctagctaa gggcactgag tgattacagg gcaaggccac
4321 agagcggcag gaagttgtaa gtgcaggggc caggcacagt ctgagtggag agccatgatg
4381 gcactcatcc ctggctggct cctgggccca ggccttttgct cagaatacag tgcccaggcc
4441 cgcctgggca ttgccttaat tcctgtctga ggctgccttc cttcatcctc ctcaagctga
4501 ctgctatcag caggagaagg gaatgcagaa ccaccccac cccaactcca gtgtctccag
4561 aactgagcag ggaccctccc catgacggag acagacaacc caatggcagg cctggggga
4621 gttctaacct cccgtgccca agctgactt ccctttccctc tccagatact gaggaaagtg
4681 ggttggaggt gggccatgag ggtggggggac aggggaggg agagccattt cctaagaaga
4741 gcccaggttg tctcagccca gggagactgg tttcaggagc tgttccttca gaaaggacga
4801 tggaaatgga agtcacagca gggctgggga actggggact ggttaggttg gacccatggg
4861 tgcagcaccc tccaaactgg tgtcagagcc tgcagatgag tcccgggagg agcggccctg
4921 caggaagcgg atgatcttct caatgtggc ctcctggtat tcgtgggacc acctgtgggc
4981 acaggagcca atgtggttca gacagctggg cagagggagc tgctagtcag ctgtttgccc
5041 acactctgcc tgtcatggtg atttgtaccc taccccctg gtcccagggc cctggggctc
5101 acttgatacc gttgaaagta agcacagcct gcatgtcctc aggcaggacc tggggctcag
5161 gccactcgaa gccatcaagt atgggcacaa tgttcttgcc gcagcttaaa gcagtcacaa
5221 tctcctggag aaagaaagga aaggaggaag ataccccgt acccatctag ggacccttgt
5281 agccaggcag gtgctgggag gcccactggc ccgaggctgg gcccagggca ggacaccagt
5341 cctgatgtcc accttgatgt ctacctaac ccttgtagtg taataaaaaa taaatatttt
5401 tcctttgccc agagttcctg gcacagagct gctaaaaccc ttggaatctc ttgagtgatg
5461 agtgtctttg tatgctaaag agatgattcc ccactgggga ccggggggt gctatggggg
5521 tagcctagat agtttcagga agagggctgg tcaccaggga gaccagggca tgactagagg
5581 attggaactt tcagccccac ctcccagcct ccagagaggt gctggagatt gagttcaatc
5641 accaatggcc aatgatttaa tcaatcatgc ctacataatg gaacctccat aaaaaccccc
5701 aaacaagggg tttttgaagag cctccaggtt gataaacagg tgtaggtgct gggaaggttg
5761 tagaaggcat ggcatccaca cctccaccct ccatacgtag agatcctatg tatctcttcc
5821 atttggctat tcttgagctg tgtcctttat aactgtgaaa ttaaataatt cagctgggca
5881 tggtgggtca cgcctgtaat cccaacactt tgggaggctg aggcaggagg atcacttgag
5941 cccaggattt tgagattaat aatattattt attactatta ttcaagctt gttaaatcaa
6001 acctaaagct cttggaactt taagttattc tgagccttga caggaattgg tctctgcagc
6061 ctgagtcatg gggcatgcag ctgcaacttc cacctatttt tttttttct gtaattactt
6121 aggaagacca aatggcacca gagataagac tcccttagat cccacttag atcaccaccc
6181 tttctcaggg ggtaataaag tcatcttcct tggaatgtag caatctataa ccaatcaaag
6241 cactgtaaca tacgcactgg tcttgtatgg aaaatgttgt aatcctgcta aaattcctct
6301 ctctttgcct gtggaagtga aaccttaact tctccagttt ggaatgctca ccccatgcct
6361 ttggagtcaa tgcttactgg gtggctattc tcaaactttg cactcaaaga aactctatac
6421 ttagtcttat tttctgaatc tcattattta aggttgacat aataaacaac taatagtaag
6481 taaagtgaaa aaaaaaaaa aaaa
```

SEQ ID NO: 2 - human PCFT full length protein, GenBank NP_542400
```
  1 megsasppek prarpaaavl crgpveplvf lanfalvlqg plttqylwhr fsadlgyngt
 61 rqrggcsnrs adptmqevet ltshwtlymn vggflvglfs stllgawsds vgrrpllvla
121 slglllqalv svfvvqlqlh vgyfvlgril callgdfggl laasfasvad vssssrsrtfr
181 malleasigv agmlasllgg hwlraqgyan pfwlalalli amtlyaafcf getlkepkst
241 rlftfrhhrs ivqlyvapap eksrkhlaly slaifvvitv hfgaqdiltl yelstplcwd
```

APPENDIX-continued

SEQ ID NOs

```
 301 skligygsaa qhlpyltsll alkllqycla dawvaeigla fnilgmvvfa fatitplmft
 361 gygllflslv itpviraklS klvreteqga lfsavacvns lamltasgif nslypatlnf
 421 mkgfpfllga glllipavli gmlekadphl efqqfpqsp SEQ ID NO: 3 - human PCFT cDNA shortened w/o exon 3, GenBank BC010691
    1 gccccacgcc acgcgtcgct ggtcccaggc agcgagtcgc tcgcgcgccc cgccgcccgc
   61 ctggcgacag ctccgccgcg cacgcacatg gaggggagcg cgagcccccc ggaaaagccc
  121 cgcgcccgcc ctgcggctgc cgtgctgtgc cggggcccgg tagagccgct ggtcttcctg
  181 gccaactttg ccttggtcct gcagggcccg ctcaccacgc agtatctgtg gcaccgcttc
  241 agcgccgacc tcggctacaa tggcacccgc caaagggcgg gctgcagcaa ccgcagcgcg
  301 gaccccacca tgcaggaagt ggagacccct acctcccact ggacccteta catgaacgtg
  361 ggcggcttcc tggtgggget cttctcgtcc accctgctgg gagcttggag cgacagtgtg
  421 ggccgccgcc cgctgctagt gctggcctcg ctgggcctgc tgctccaggc cctagtgtcc
  481 gtttttgtgg tgcagctgca gctccacgtc ggctacttcg tgctgggtcg catccttttgt
  541 gccctcctcg gcgacttcgg tggccttctg gctgctagct ttgcgtccgt ggcagatgtc
  601 agctccagtc gcagccgcac cttccggatg gccctgctgg aagcagcat cggggtgggct
  661 gggatgctgg caagcctcct cgggggccac tggctccggg cccagggtta tgccaaccccc
  721 ttctggctgg ccttggcctt gctgatagcc atgactctct atgcagcttt ctgctttggt
  781 gagaccttaa aggagccaaa gtccacccgg ctcttcacgt tccgtcacca ccgatccatt
  841 gtccagctct atgtggctcc cgcccccagag aagtccagga aacatttagc cctctactca
  901 ctggccatct tcgtggtgat cactgtgcac tttggggccc aggacatctt aaccctttat
  961 gaactaagca cacccctctg ctgggactcc aaactaatcg gctatggttc tgcagctcag
 1021 catctccccct acctcaccag cctgctggcc ctgaagctcc tgcagtactg cctggccgat
 1081 gcctgggtag ctgagatcgg cctggccttc aacatcctgg ggatggtggt ctttgccttt
 1141 gccactatca cgcctctcat gttcacaggt gctctctttt ctgctgtggc ctgtgtgaat
 1201 agcctggcca tgctgacggc ctccggcatc ttcaactcac tctacccagc cactctgaac
 1261 tttatgaagg ggttccccctt cctcctggga gctggcctgc tgcteateee ggctgttctg
 1321 attgggatgc tggaaaaggc tgatcctcac ctcgagttcc agcagttttcc ccagagcccc
 1381 tgatctgcct ggaccagaag acagagggca agaggagcaa agtgaacacc aagcaactgg
 1441 aggtctgcag ctggaagccc agccacagc aggacaagca actcttgtct aagggcagtg
 1501 ctctctttgg acgaggtagt caagagagac caaggcacca cccatccac agctgaccca
 1561 gcctctgtct aggatctaga atcataaccc acacaggccc actgcaggac aggtggcaga
 1621 ggagctattt gggacaggag tcagttctcc ctttctgcta tccatcactt ataaccccac
 1681 aggccagagg agaggtcctg agagaggtga cacttcaggg accagaggca gcacgagggc
 1741 tggcatctct ccttccagcc caaactgcac agccccaacc aggttcccaa cacgtgtagc
 1801 agtcatcagc cattccttaa caatgaatgt ggtacctggt tagtgccagc cttgggaagg
 1861 agggagggag gtaagagggg cttggtgatc tctggaggaa gagtgttgcc tttgctgtgg
 1921 ttggggaatc gatccttggc tatggcctac ccactcccct ggctgaagag tgccaatcat
 1981 tacaaatcag cttcagcaaa ctgaaaaaaa aaaaaaaa SEQ ID NO: 4 - human PCFT protein shortened w/o exon 3, GenBank AAH10691
    1 megsasppek prarpaaavl crgpveplvf lanfalvlqg plttqylwhr fsadlgyngt
   61 rqrggcsnrs adptmqevet ltshwtlymn vggflvglfs stllgawsds vgrrpllvla
  121 slglllqalv svfvvqlqlh vgyfvlgril callgdfggl laasfasvad vsssrsrtfr
  181 malleasigv agmlasllgg hwlraqgyan pfwlalalli amtlyaafcf getlkepkst
  241 rlftfrhhrs ivqlyvapap eksrkhlaly slaifvvitv hfgaqdiltl yelstplcwd
  301 skligygsaa qhlpyltsll alkllqycla dawvaeigla fnilgmvvfa fatitplmft
  361 galfsavacv nslamltasg ifnslypatl nfmkgfpfll gagllipav ligmlekadp
  421 hlefqqfpqs p SEQ ID NO: 5 - mouse PCFT protein, GenBank NP_081016
    1 megrvssvgs phsflnapvl frgpveplvf lanfalvlqg plttqylwhr fstelgyngt
   61 rhrencgnqs adplmkevet ltshwtlymn vggflvglfw stllgawsdr vgrrpllvla
  121 slglllqavv sifvvqlelh vgffvlgral callgdfngl laasfasvad vssnhsrtfr
  181 malleacigv agtlasllgg hwlraqgyan pfwlalalli vmalyaafcf getvkepkst
  241 rlftlrhhrs iarlyvvpap eksrmhlaly slaifvvviv hfgaqdiltl yelsaplcwd
  301 skligygsaa qhlpyltsll glrllqfcla dtwvaeigla fnilgmvvfa fatitplmft
  361 gygllflslv ttpviraklS klvseseqga lfsavacvns lvmlmasgif nsiypatlnf
  421 mkgfpfllga gllfipaili gvlekvnphp efqqfpqsp SEQ ID NO: 6 - human full length PCFT gene, GenBank DQ496103
    1 acctctaccc tagtgggtac tgcaggctct ggctctggga tgagccacac cctgtcccat
   61 tcctgatgag ggaccttggc ctctcctagc cttagttctt tatctaagaa ataattccaa
  121 ggatttagcc aagtacccct ccctcactgc agctgaccta actgggcaa gcttttgtgt
  181 aagtggtagg gaggagttgg aaggggaggg aggagagtgg agccaatcca gaggcttgaa
  241 tgtttaatgt ggaatttcct ctctctaggg gaccacaggt ggggcagct gcaggggga
  301 ggttattcag ttcactagta tctagccagc acctaccat cctgagtctc ggactcctgg
  361 ctcaggggag gtgggtagc taacaagctc caacaggccc aggcacagtc acagtggcca
  421 gaattggagc catccatcct cccaagaatc aggcctgcc tgacctgcct ccagaaaccc
  481 actcagctgc tctgttctca gggaaggtgg cctttcctga ttctgctccc cctacctcca
  541 gccctgaat tagcacccct ggagttcaaa actattttcc acggttgaa ttttgtatca
  601 attagtagga ttctttgact attttttcct tccaccatt ctagaaacta acgggcctgg
  661 tgagggcttt gtctattttcc tttcctgttg tggtcccgga gtcccccagc acagtgcctg
  721 gcacgtaagg ggcactcagt aaatgagctg aatgaatgaa agatagggga gtaaggaagg
  781 taatgctgtt ccttttaca ggcaataaaa cagaggccca gacagggtct gacctcctca
  841 gcagcagagc aggtgactgc cttctgcct aattcctata atgggagcca cccaggagca
  901 taggttcaca cccaaggacc tcccaggccc tcccccatct tctctaaggg aactgcagag
```

APPENDIX-continued

SEQ ID NOs

```
 961 ccaggccctg cctgacccca gaaacaagac tagtttccca ggaaaagatc ctagggcagg
1021 agtggagcaa gtgacagctt gtttttttatt ttattttttat tttatattttt ttgagacagg
1081 gtcttgctct gtcacccagg ctggagtgca gtggtgcgat ctcagcccac tgcaacctct
1141 gcctcctggg ctcaattgat cctcccacct cagccacccg agtacctggg actacaggta
1201 tctgctacta cgcctggcta attttttgtgt attttttgta gagacagggt tttaccatgt
1261 tgcccagatt ggtctcgaac tcctgggttc aagcgatcca tgcgcctcag cctccaaaag
1321 tgctgggatt acaggtgtga gccaccactc ccagacgtga cagcctgtta atagcaataa
1381 tagcactttg aatataccag acactgcttt tccacaactt tttgagacat gttttgttag
1441 caactccatt ttacagatga aaaacagag gctcagggtg gtaagtggca tgccgaaggt
1501 agtggcagag cctaggtgtt ccagcccagg cagctgggct cagcccactc cgatcctctc
1561 cagctgcctc tctgttacag cgcagaacat cagcagcatc aggagtcatg tgctcttcca
1621 gctctgcctt gagtacccga tgacctcgtt tcctcagcgg tagatagcga tggttaatat
1681 tggctagcct gtagagttat cgggagacca acgcacaaaa agggtttaat accgtgccca
1741 gcacatagta agtggtcaat acatgttaat tgttgatatt cttgttatct gtggtgtgtc
1801 tgggccggga gggagggctg cagggcggtg tctacgcaca ctttacaggt gaggtcatcc
1861 cgcgggctgg gggtgccggg ccctcgctg gcccacgccc agccaggtgc acccgcggcg
1921 agagtccggt ggcctcaggt cacaggcccc tccccgccgg acatttaagg agggacgccg
1981 ggcgcaggcg cagacagcgc aagcccacg ccacgcgtcg ctggtcccag gcagcgagtc
2041 gctcgcgcgc cccgcgcccc gcctggcgac agctccgccg cgcacgcaca tggaggggag
2101 cgcgagcccc ccggaaaagc cccgcgcccg cctgcgggct gccgtgctgt gccggggccc
2161 ggtagagccg ctggtcttcc tggccaactt tgccttggtc ctgcagggcc cgctcaccac
2221 gcagtatctg tggcaccgct tcagcgccga cctcggctac aatggcaccc gccaaagggg
2281 gggctgcagc aaccgcagcg cggaccccac catgcaggta gcgggggcgc gaggagcctg
2341 gcaggtggag ggccctggtc tggagcgtgg gggcagcgga ggggcgggc ctgcgtaatg
2401 gtagtggcgg gtaactggag ggagggtgca ttttggatgg tgggcgggac cagagcaaag
2461 gggcctgacc gagaacctca gcgggtggga tgcgaaaagc tgagctaaag tctggccttg
2521 caggttaaca aaagggggg gaaaggaaag ggaatgggagc cttggtccat gtccttcccc
2581 ctctccactg gcagatttttg aaagctgtgc taagattctc tgaggtttag ggctccaaag
2641 gaagtcctca tccctgtagc tcccgggatg gcgaggattt ggggattgtg gaacccagag
2701 tgaggaaccg caccctggtc attgtgcccc tacaggaagt ggagacccctt acctcccact
2761 ggaccctcta catgaactg ggcggcttcc tggtgggggct cttctcgtcc accctgctgg
2821 gagcttggag cgacagtgtg ggccgccgcc cgctgctagt gctggcctcg ctgggcctgc
2881 tgctccaggc cctagtgtcc gttttttgtgg tgcagctgca gctccacgtc ggctacttcg
2941 tgctgggtcg catcctttgt gccctcctcg gcgacttcgg tggccttctg gctgctagct
3001 ttgcgtccgt ggcagatgtc agctccagtc gcagccgcac cttccggatg gccctgctgg
3061 aagccagcat cggggtggct gggatgctgg caagcctcct cggggggccac tggctccggg
3121 cccagggtta tgccaacccc ttctggctgg ccttggcctt gctgatagcc atgactctct
3181 atgcagcttt ctgctttggt gagaccttaa aggagccaaa gtccacccg ctcttcacgt
3241 tccgtcacca ccgatccatt gtccagctct atgtgcctcc cgcccccagag aagtccagga
3301 aacatttagc cctctactca ctggccatct tcgtggtgat cactgtgcac tttggggggcc
3361 aggacatctt aacccttttat gaactaagca caccccctctg ctgggactcc aaactaatcg
3421 gctatggttc tgcagctcag catctcccct acctcaccag cctgctggcc ctgaagctcc
3481 tgcagtactg cctggccgat gcctgggtag ctgagatcgg cctgccttc aacatcctgg
3541 ggatggtggt ctttgccttt gccactatca cgcctctcat gttcacaggt aaagtgtgtg
3601 ggctcaggga cagccttgtcc cagaggcact gggtaagaac tgggggccgg ccactcactg
3661 cccccagatg tggttcattc ctgtgtcttt ggaaacatag ttatgccccc agcctgcact
3721 ggagaacaga caactaagaa atccctcaaa aatgccatct ttgatacatg gaaaatatag
3781 accttcagta gctaaagtaa ttaacccact gttatcaacc attaatattg ttagtaatat
3841 agagcaaaag acaaaagtgt ggctcataca ctaattgctt taccccttgg cctcccaccg
3901 cctattcata tgttcttaaa caaagtccat gccattaatg cctggtactc acttctctga
3961 taagaatcac aggacctacc tcaaatccc ttagtcagct tctttgggtt ttttaaaaac
4021 cagtcttctc ggaccacaga tatgaaattc ctgcttcagt tcctcttctc ctcttttctcc
4081 ttctccttttc cctcctcact tcctccccttt ctttttttga tgggagaggg tcaacaggcc
4141 agtaaatgag gaagttaact ttttaaaatt tttatttgat tgatgtattt agagacaggg
4201 tctcgctttg ttacccaggc tagagtgcag tggcacgatc atggctcact gcagcctcat
4261 cccccgggcc cagatgatcc tcccaccttg gcctctctag tagctgggac cactggtgca
4321 cattaccaca ccttgctaat ttttgtattt tttatagaga tgggggtcctc accattttgc
4381 ccagtccagg tctctaactc ctgagctcaa ggatccgcct gcctcagcct cccaaagtgt
4441 tgggattaca ggcatgagcc accgtgcccg gctttagtta actttttttta aagggacaga
4501 tttatttttga tagagcccta aaatgtgctg tgtatagtca acaatacaat aatcacagat
4561 ttcttaactc aactgcttgt ctgacaatta agcagaaggg aacctttccc tcctgctgat
4621 ggccctgggg gatgcagaga tgataaagat gctgtcattg ctctgggtcg ggggaggtc
4681 tcaacagagt gggatttgag gggcctgaca ctgctagggt ccctggatgc ctcatcgtat
4741 accttctttg gaggatccac tgtcctgtag gagttttgcag ttttgctgag gagtcagcag
4801 tcgcacaggg agagaaatgg ttatgaagaa aacaggaagc ctgtaagtaa ctgaatgcaa
4861 agggaaaagg aactcccatt tgctgtgtcc ctatgccatg tcttcatag atgttacctt
4921 tttacctcat gtattggttc cctgagattg ctgtaatgac ataccacaaa cttgggggct
4981 taacacaaca gaaacatatt ctctcacagt tctggaggcc agaagtccaa agtcagtacc
5041 accgggctga atggaagcag tcagcaggca gtgctccctt gcaagcctcc aggagagaac
5101 gtgtttctca tttcttccag cttctgggc tgctggcatt ccttggcttg gggcggccat
5161 caccagtctc tgcctctgtg ctcacattga ctctcctcct ctttgtgcct tctcaattct
5221 gtcggtgcca aatctccgtc tgctttcctc ttataaagat atgtgtgacg gcatttaggg
5281 cccaacctaa tccaggataa atctgctctc tcaggaggct taactgcaca cctgcataga
5341 ctcattttcc aaataaggta gtatttacag gttccagggc tatgaatctg atgccattgg
5401 gcaccattat tcagcctcct atgcctcaga accatcctgt gatgaaggcc ttattatctt
5461 cctcatacag ggagtcagga tcagagaggg taagtacccc aggccacaca gataatatgt
5521 aatggcatca ggttttgaac tcagggctga ctccaaagcc catgcttgtt ttctgtgccc
```

APPENDIX-continued

SEQ ID NOs

```
5581 tgccatatcc ctactaagtg ccaagtgggt gggtgatgcc tgctgtgacc acaagaggtt
5641 cagacaagaa agcaatcaat gggaattagc attcattcat gagagctgag aggtggccaa
5701 gcccagacaa gggcagtctc cattcctcct tgactactgt cttcccaccc tcaccatcaa
5761 ggaagttctt cctgggtcta acctaagccc cacatggggt atggatagga gctctgctgc
5821 ctttcccttg gacgccctc tccccagccc cattttcctg atgagtgttt gtttctccac
5881 aggatatggg ttgcttttcc tgtcattagt catcacacct gtcatccggg ctaaactctc
5941 caagctggtg agagagacag agcagggtga gtgtcagaac ccacctgtgt ctggttcctc
6001 atgtccagtg ctgcccgaaa cgggctgatg ggcagccatg gctgggggaa cagcttgcct
6061 tcccccctct caccctggag aagtaagtgg ccaaaacaaa cacatttctg tgaaattgcc
6121 cacaatgggc agaggatcat gccaccttgg attttcaaac cgcagagttg ggatttgcag
6181 tcagcagagc acaattatgt tctttctaga taaccagagc agaggattta ctctctgcag
6241 acctcagctt ttccgtctgt aagatgggtg tggtgatgcc agagttccct gtttctctgg
6301 ggtcagcgtg tacaagccca gaagtgaaca accttgtgac atgggtttca ttttccacag
6361 ttgacagata aagaaacaga gacccagggg gttacattgg ctcacccaag gttactcagt
6421 aaatggtgga gctaggatgc aaacctacgt ctgtgtttaa aagcagctgg tctcaggatc
6481 tgggttttag tccgagccct gccacaggcc tgtttcttca tctgtgatgt gggtggtttg
6541 cttttgatga catcacagac ccctctagat gtgacagaat ttaatctcaa cttctgttgg
6601 gttgttgcac attttgtaaa ctgtgggttc tcctggtata tctataaaga acagcttctc
6661 cagcctctgg gtctttatgc cccagtctgg aaacattcat ctttttccat ctgtcctgga
6721 atgaggatct gatgatgaca gagactctgg tgccatacag agcccactgt gggttctggt
6781 gtccccagaa tccatgtgtc ttcattcatt cacctaaact ttttttccca gcactttctc
6841 tgtgcccaga gatgtcaaga gaaacaggag aaaagaacag cccttactaa ctagctactt
6901 ccaggggacc aggcccagtg atgggtgatt tccatgtgaa cttaatgttg ctcacaatct
6961 aggaaatagg tattatcctt atttagcaga aggaggaaca ggaacccaaa ggataagaag
7021 ctattcagtg gtgacaccgc tatgaatatt ggaactgatc agaccagcag ttaatcccaa
7081 acaggagatg attccaaaga ggataaacca gaaaaagcc atttccatca agctttcatc
7141 agacaatatc acatgtactt ttttttttct tttatgtgct gggttctgtc agatcacatg
7201 tactttttaat gtggatttaa tagcagccat ttgttagta gcccctctgt gccagctact
7261 gtccacatat gaccttactg aatccttgtc acagtacatg atgtagcagg atttactggt
7321 gaggaagggg agacataggt taagtgacta ctcccggtca cacagctgtg aggtggtggt
7381 gccagagttg gaatatggcc ctttcggact ccagatgtg gtatttattt cttcacaggt
7441 gctctctttt ctgctgtggc ctgtgtgaat agcctggcca tgctgacggc ctccggcatc
7501 ttcaactcac tctacccagc cactctgaac tttatgaagg ggttcccctt cctcctggga
7561 gctggcctcc tgctcatccc ggctgttctg attgggtaat gcagggccct gaacccatgc
7621 tcataatgga gcccttctc ttaaaagttt cctcttctc tcccaaccag aaatggcaag
7681 ttcattcctg gaatccttac cctctgggtg tcttgtccca ggttgccct ctccttgcag
7741 atggctgcct aatcctccag gagccatttt ccaagggcga gatggcgagc taggtggagg
7801 aaggatcagg ctaacattgc tgcttggcaa ggctgtgttc tctatcccag ttcccctatt
7861 tccctccatt cccatttat agatgaact atggcagcag aactgtgtta aagggaaggc
7921 caggaagctt tgtcagctag ttgtggctgg gccacaggct agcttgaccc gctgacttt
7981 tcctgtatga tattaagaat tatatttcat ggccgggcgt ggaggctctt gcctgtaatc
8041 ccgatcctgt gggaggctga ggcaggagga ccacttgagc ccgggaattc aagatcagcc
8101 tgggcaacat agcaagacct tgtctgtata aaaaatttaa aaaatcaaac aggcatggtg
8161 gtatgcactg gtagtcccag ctactaagga ggctgaggca ggaggatcac ttgagcccag
8221 gagttcaagg gtacagtgag ctatgattat gtcactgccc tccagcctgg acaacagagc
8281 aagaccctgt ctcttaaaaa aaaaaaagtt attttccaga gccatgtccc tggatattgt
8341 cctccagctc tcagcttctc agcttgggga aggaggaggt tcaggagagc tacctggacc
8401 agcccaccc agtaaatcct gtgtcacttc tccagacagg cctgagggt tccccacatg
8461 aaatccaaac tctctctctg gtctctcaca ggatgctgga aaaggctgat cctcacctcg
8521 agttccagca gtttcccag agccctgat ctgcctggac cagaagacag agggcaagag
8581 gagcaaagtg aacaccaagc aactggaggt ctgcagctgg aagcccagcc cacagcagga
8641 caagcaactc ttgtctaagg gcagtgctct ctttggaaga ggtagtcaag agagaccaag
8701 gcaccacccc atccacagct gacccagcct ctgtctagga tctagaatca taacccacac
8761 aggcccactg caggacaggg gcagaggag ctatttggga caggagtcag ttctcccttt
8821 ctgctatcca tcacttataa ccccacaggc cagaggagag gtcctgagag aggtgacact
8881 tcaggacca gaggcagcac gagggctggc atctctcctt ccagcccaaa ctgcacagcc
8941 ccaaccaggt tcccaacacg tgtagcagtc atcagccatt ccttaacaat gaatgtggta
9001 cctggttagt gccagccttg ggaaggaggg agggaggtaa gaggggcttg tgatctctg
9061 gaggaagagt gttgcctttg ctgtggttgg ggaatcgatc cttggctatg gcctacccac
9121 tccctggct gaagagtgcc aatcattaca aatcagcttc agcaaactga aacaaacctt
9181 ctggtgcctt gggctttggg gccctctgtt ttcctgctcc cagtctgcct gccatacgtt
9241 agacaacaga agctgctggg ctgggcagga gccctgagct gcctggtgga ttggtaccaa
9301 gtggggccag ccagggcttc tactgactcg ctgtgcaacc ttgagcaagc cccactagga
9361 acggctagat cagcaatgcc ccaaattgtt gaatcgtggt gatcacattt ggatggacaa
9421 gttaggaaac ttagctgatt ctctgagata cttcccactt cctcatacat tctacagtga
9481 gatgcctctc ttcatgggcc tggggaaagg atgaatgagt gtggctggac ttttgacctt
9541 taatgtccct gagcagttct tggcccttgg ggagaagtag ggggaggatc tggctgactc
9601 agcccaacc gagggtagc agctgcagcc cagccaagca gaacaccctg gccctacaga
9661 cctgtgtctg agcaggcttt ggaggaaagg ccacttctga gtcctctgtc tcaggagaag
9721 ccaggcctag gtgcttgacc tggtgatctg agctgtgttt gtcctagtat gggtggcagt
9781 cacctctgaa cacactggcc ttggcttaga ggaggcttgt gacttcagct gttccagctg
9841 gggctggatg ctggactctg attccctcag agagacagaa gatcgggcag aggtcaacca
9901 gaaggccaca cagggcagtg gacaacagtg gagggtatac caaatagaaa taaaatgcag
9961 gaaacctctc tgaatactgc ccttggggac ctcaggaggg agtgggactg attggagaca
10021 aagagccaga aatcatcccc tggagatact cagacactgt attgttattg gcgctgtcct
10081 gtgagggcag tgtccaggct gccctgcttg tcatatccat gcctggctc tggccccggt
10141 gagcacttgt gctgcatgag gaaaggagga tcaggtgggg tcaaaaccaa agcatcgagg
```

APPENDIX-continued

SEQ ID NOs

```
10201 ctggcactgg ccaagacaga ctctggcagg gaggggagtg gaaggaagga gccccaaacc
10261 tggagtgaga cctttgactt tctgatgatg tggccaagaa ctaggagtca cctggccagc
10321 acagccaaga gtggggctgg gggcgcagcc agctttaagg tgtcaacacc tggcccttgc
10381 ggggaaagag ccttcagcag cccccacggc ctggagcctg ggtttattgg agggtgcttt
10441 cttaccctct gaacccagtg gaggaggggg caatgggata ttcctgctct gtatggcctc
10501 tgggtcagct ttttgttgca aaatcctatc ccccgctgct agattctttg aagcaaggga
10561 gaagcaatag cccagcctca gaatgattct caggaaagca attccactgc cagtggactg
10621 ggtgccagga ggcctaggtc tggatctggg gctgccacta atgacaggaa agtgggctta
10681 tcctcaacct ttctgagcct cagtgtcatt atctgtaaaa tgggatgat aataccaggt
10741 agagttgctc tgatgactgg agaccatgga gcggagtgtt tgggaaatgg caaagatttg
10801 tgagggcttc gtgctttaga gatttgctac ccttaaccac cagcatcagc tcacctggga
10861 atctgtaaga aatgcagagt cctaggcccc accccagatc tcctgatttt aacaacattc
10921 ccaggtgact tggatgcatg ttaaagttgg agaagctgcc ctaagtgaca acccttgcc
10981 ttttcaggac tttgcctctt tccacagagc tgcaggttct gtctaggctg cttttactgc
11041 catgggggct gcctggtccc tgagtaagca gtgggtagcc ctggatggct gaggggctgg
11101 ggaagccagc tgggccagac caggaaggag cctgaggcac agcaccaagg catggggtag
11161 ggtgggcttt g
```

SEQ ID NO: 7 - forward primer for amplifying human full length PCFT cDNA
TATAGATCTCACCATGGAGGGGAGCGCGAGC SEQ ID NO: 8 - reverse primer for amplifying human full length PCFT cDNA
TATAGATCTCAGGGGCTCTGGGGAAACTG SEQ ID NO: 9 - forward primer for quantitative PCR of PCFT cDNA - pair 1
ATGCAGCTTTCTGCTTTGGT SEQ ID NO: 10 - reverse primer for quantitative PCR of PCFT cDNA - pair 1
GGAGCCACATAGAGCTGGAC SEQ ID NO: 11 - forward primer for quantitative PCR of PCFT cDNA - pair 2
CTGTCATCCGGGCTAAACTC SEQ ID NO: 12 reverse primer for quantitative PCR of PCFT cDNA - pair 2
AGGCCACAGCAGAAAAGAGA SEQ ID NO: 13 forward primer for quantitative PCR of G3PDH cDNA
CGACCACTTTGTCAAGCTCA SEQ ID NO: 14 - reverse primer for quantitative PCR of G3PDH cDNA
CCCTGTTGCTGTAGCCAAAT SEQ ID NO: 15 - forward primer for quantitative PCR of β-actin cDNA
CGTGCTGCTGACCGAGC SEQ ID NO: 16 - reverse primer for quantitative PCR of β-actin cDNA
GAAGGTCTCAAACATGATCTGGGT SEQ ID NO: 17 - forward primer for PCR of exon 1 of the PCFT gene
TACGCACACTTTACAGGTGAGGTCATC SEQ ID NO: 18 - reverse primer for PCR of exon 1 of the PCFT gene
CCAAAATGCACCCTCCCTCCAGTTAC SEQ ID NO: 19 - forward primer for PCR of exon 2 of the PCFT gene
TTCTCTGAGGTTTAGGGCTCCAAAGG SEQ ID NO: 20 - reverse primer for PCR of exon 2 of the PCFT gene
TAGTTGTCTGTTCTCCAGTGCAGGCT SEQ ID NO: 21 - forward primer for PCR of exon 3 of the PCFT gene
TTCCTCCTTGACTACTGTCTTCCCAC SEQ ID NO: 22 - reverse primer for PCR of exon 3 of the PCFT gene
TCTGCTGACTGCAAATCCCAACTCTG SEQ ID NO: 23 - forward primer for PCR of exon 4 of the PCFT gene
TAGCAGGATTTACTGGTGAGGAAGGG SEQ ID NO: 24 - reverse primer for PCR of exon 4 of the PCFT gene
TGCCAAGCAGCAATGTTAGCCTGATC

APPENDIX-continued

SEQ ID NOs

SEQ ID NO: 25 forward primer for PCR of exon 5 of the PCFT gene
TATTGTCCTCCAGCTCTCAGCTTCTC SEQ ID NO: 26 - reverse primer for PCR of exon 5 of the PCFT gene
AAGGTTGCACAGCGAGTCAGTAGAAG SEQ ID NO: 27 - forward primer for PCR of exon 3 of PCFT cDNA
CAGCTCAGCATCTCCCCTAC SEQ ID NO: 28 - reverse primer for PCR of exon 3 of PCFT cDNA
AAGAGAGCACTGCCCTTAGACAAG SEQ ID NO: 29 - forward primer for PCR of full length open reading frame of PCFT cDNA
CGTCACCTTCGTCCCCTCCG SEQ ID NO: 30 - reverse primer for PCR of full length open reading frame of PCFT cDNA
TAGCAGGATAAGCGGAGGCC SEQ ID NO: 31 - coding region of PCFT cDNA - nt 97-1476 of SEQ ID NO: 1. Mutants are bold-underlined

```
   1 atgg aggggagcgc gagcccccg
  25 gaaaagcccc gcgcccgccc tgcggctgcc gtgctgtgcc ggggcccggt agagccgctg
  85 gtcttcctgg ccaactttgc cttggtcctg cagggcccgc tcaccacgca gtatctgtgg
 145 caccgcttca gcgccgacct cggctacaat ggcacccgcc aaaggggggg ctgcagcaac
 205 cgcagcgcgg accccaccat gcaggaagtg gagacccta cctcccactg gaccctctac
 265 atgaacgcgg gcggcttcct ggtggggctc ttctcgtcca ccctgctggg agcttggagc
 325 gacagtgtgg ccgccgccc gctgctagtg ctggcctcgc tgggctgct gctccaggcc
 385 ctagtgtccg tttttgtggt gcagctgcag ctccacgtcg gctacttcgt gctgggtcgc
 445 atcctttgtg ccctcctcgg cgacttcggt ggccttctgg ctgctagctt tgcgtccgtg
 505 gcagatgtca gctccagtcg cagccgcacc ttccgatggg ccctgctgga agccagcatc
 565 ggggtggctg ggatgctggc aagcctcctc gggggccact ggctccgggc ccagggttat
 625 gccaacccct tctggctggc ctttggccttg ctgatagcca tgactctcta tgcagctttc
 685 tgctttggtg agaccttaaa ggagccaaag tccacccggc tcttcacgtt ccgtcaccac
 744 cgatccattg tccagctcta tgtggctccc gccccagaga agtccaggaa acatttagcc
 805 ctctactcac tggccatctt cgtggtgatc actgtgcact tggggccca ggacatctta
 865 acccttatg aactaagcac accctctgc tgggactcca aactaatcgg ctatggttct
 925 gcagctcagc atctccccta cctcaccagc ctgctgcc tgaagctcct gcagtactgc
 985 ctggccgatg cctgggtagc tgagatcggc ctggccttca acatcctggg gatggtggtc
1045 tttgcctttg ccactatcac gcctctcatg ttcacaggat atgggttgct tttcctgtca
1105 ttagtcatca cacctgtcat ccgggctaaa ctctccaagc tggtgagaga gacagagcag
1165 ggtgctctct tttctgctgt ggctgtgtg aatagcctgg ccatgctgac ggcctccggc
1225 atcttcaact cactctaccc agccactctg aactttatga aggggttccc cttcctcctg
1285 ggagctggcc tcctgctcat cccggctgtt ctgattggga tgctggaaaa ggctgatcct
1345 cacctcgagt ccagcagtt tccccagagc cctga
```

---

What is claimed is:

1. A method of diagnosing folate malabsorption in a human or determining whether a human may be a carrier of a nucleic acid associated with folate malabsorption, said method comprising (i) determining whether or not the human has a mutation in one or both copies of nucleic acid encoding proton-coupled folate transporter (PCFT), in comparison to a wild type PCFT nucleic acid, resulting in a loss of PCFT function or reduced PCFT activity, wherein a mutation in both copies of the nucleic acid encoding PCFT resulting in loss of PCFT function or reduced PCFT activity is diagnostic of folate malabsorption and a mutation in one copy of the nucleic acid encoding PCFT is indicative that the human may be a carrier of a gene associated with folate malaborption, wherein the wild type PCFT nucleic acid encodes the amino acid sequence of SEQ ID NO:2, wherein the mutation is selected from 5882G>A of SEQ ID NO:6, 2284delG of SEQ ID NO:6, 2844C>A of SEQ ID NO:6, 2946G>C of SEQ ID NO:6, 3461C>G of SEQ ID NO:6, 5927C>T of SEQ ID NO:6 or 7548C>G of SEQ ID NO:6; or (ii) determining whether or not the human expresses an active PCFT, wherein an active PCFT is indicative that the human has the ability to undergo intestinal folate absorption and the absence of an active PCFT is diagnostic of folate malabsorption, wherein the active PCFT has the amino acid sequence of SEQ ID NO:2.

2. The method of claim 1, wherein peripheral blood lymphocytes are evaluated for expression of an active PCFT.

3. The method of claim 1, wherein tissue from a biopsy is evaluated for expression of an active PCFT.

4. The method of claim 1, wherein the human is a fetus and amniotic fluid or chorionic villus are evaluated.

5. The method of claim 1, wherein the human is a pregnant woman.

6. The method of claim 1, wherein activity of intestinal folate absorption is measured directly.

7. The method of claim 1, wherein the genotype of the nucleic acid encoding PCFT in the human is determined.

8. The method of claim 7, wherein a PCFT nucleic acid having the DNA sequence of SEQ ID NO:6 encodes an active PCFT.

9. The method of claim 7, wherein the nucleic acid encoding PCFT comprises a mutation causing a reduction or elimination of intestinal folate absorption.

10. The method of claim 9, wherein the nucleic acid encoding PCFT comprises a mutation causing a deletion in the amino acid sequence of the expressed protein.

11. The method of claim 9, wherein the mutation in the nucleic acid is 5882G>A of SEQ ID NO:6.

12. The method of claim 9, wherein the mutation in the nucleic acid is 2284delG of SEQ ID NO:6.

13. The method of claim 9, wherein the mutation in the nucleic acid is 2844C>A of SEQ ID NO:6.

14. The method of claim 9, wherein the mutation in the nucleic acid is 2946G>C of SEQ ID NO:6.

15. The method of claim 9, wherein the mutation in the nucleic acid is 3461C>G of SEQ ID NO:6.

16. The method of claim 9, wherein the mutation in the nucleic acid is 5927C>T of SEQ ID NO:6.

17. The method of claim 9, wherein the mutation in the nucleic acid is 7548C>G of SEQ ID NO:6.

18. The method of claim 9, wherein the human is heterozygous for an inactive PCFT.

19. The method of claim 9, wherein the human does not have an active PCFT.

20. The method of claim 19, wherein both PCFT alleles comprise a mutation causing a reduction or elimination of intestinal folate absorption activity.

21. The method of claim 1, wherein PCFT mRNA from the human is evaluated to determine whether mRNA of an active PCFT is present.

22. The method of claim 21, wherein the PCFT mRNA is evaluated by making a cDNA from the PCFT mRNA and determining whether the cDNA comprises the sequence of SEQ ID NO:31, wherein the presence of cDNA comprising the sequence of SEQ ID NO:31 indicates the presence of an active PCFT in the human.

23. The method of claim 1, wherein tissue of the mammal is tested for PCFT activity.

24. The method of claim 23, wherein the PCFT activity is determined by measuring uptake of a radiolabeled substrate of PCFT.

25. The method of claim 24, wherein the radiolabeled substrate of PCFT is [$^3$H]folic acid, [$^3$H]pemetrexed, [$^3$H]methotrexate, [$^3$H]5-methyltetrahydrofolate, or [$^3$H]5-formyltetrahydrofolate.

* * * * *

SEQUENCE LISTING

<160> NUMBER OF SEQ ID NOS: 31

<210> SEQ ID NO 1
<211> LENGTH: 6505
<212> TYPE: DNA
<213> ORGANISM: Homo sapiens

<400> SEQUENCE: 1

```
acagcgcaag ccccacgcca cgcgtcgctg gtcccaggca gcgagtcgct cgcgcgcccc    60
gccgcccgcc tggcgacagc tccgccgcgc acgcacatgg aggggagcgc gagcccccg   120 gaaaagcccc gcgcccgccc tgcggctgcc gtgctgtgcc ggggcccggt agagccgctg   180
gtcttcctgg ccaactttgc cttggtcctg cagggcccgc tcaccacgca gtatctgtgg   240
caccgcttca gcgccgacct cggctacaat ggcacccgcc aaaggggggg ctgcagcaac   300
cgcagcgcgg accccaccat gcaggaagtg gagacccta cctcccactg gaccctctac   360
```

-continued

```
atgaacgtgg gcggcttcct ggtggggctc ttctcgtcca ccctgctggg agcttggagc    420
gacagtgtgg gccgccgccc gctgctagtg ctggcctcgc tgggcctgct gctccaggcc    480
ctagtgtccg ttttgtggt gcagctgcag ctccacgtcg gctacttcgt gctgggtcgc     540
atcctttgtg ccctcctcgg cgacttcggt ggccttctgg ctgctagctt tgcgtccgtg    600
gcagatgtca gctccagtcg cagccgcacc ttcggatgg ccctgctgga agccagcatc     660
ggggtggctg ggatgctggc aagcctcctc gggggccact ggctccgggc ccagggttat    720
gccaacccct tctggctggc cttggccttg ctgatagcca tgactctcta tgcagctttc    780
tgctttggtg agaccttaaa ggagccaaag tccacccggc tcttcacgtt ccgtcaccac    840
cgatccattg tccagctcta tgtggctccc gccccagaga agtccaggaa catttagcc     900 ctctactcac tggccatctt cgtggtgatc actgtgcact tggggcccca ggacatctta    960 acccttatg aactaagcac accctctgc tgggactcca aactaatcgg ctatggttct     1020
gcagctcagc atctcccta cctcaccagc ctgctggccc tgaagctcct gcagtactgc    1080
ctggccgatg cctgggtagc tgagatcggc ctggccttca acatcctggg gatggtggtc    1140
tttgcctttg ccactatcac gcctctcatg ttcacaggat atgggttgct tttcctgtca    1200
ttagtcatca cacctgtcat ccgggctaaa ctctccaagc tggtgagaga gacagagcag    1260
ggtgctctct tttctgctgt ggcctgtgtg aatagcctgg ccatgctgac ggcctccggc    1320
atcttcaact cactctaccc agccactctg aactttatga aggggttccc cttcctcctg    1380
ggagctggcc tcctgctcat cccggctgtt ctgattggga tgctggaaaa ggctgatcct    1440
cacctcgagt tccagcagtt tccccagagc ccctgatctg cctggaccag aagacagagg    1500
gcaagaggag caaagtgaac accaagcaac tggaggtctg cagctggaag cccagcccac    1560
agcaggacaa gcaactcttg tctaagggca gtgctctctt tggacgaggt agtcaagaga    1620
gaccaaggca ccaccccatc cacagctgac ccagcctctg tctaggatct agaatcataa    1680
cccacacagg cccactgcag acaggtggc agaggagcta tttgggacag gagtcagttc     1740 tcccttctg ctatccatca cttataaccc cacaggccag aggagaggtc ctgagagagg     1800
tgacacttca gggaccagag gcagcacgag ggctggcatc tctccttcca gcccaaactg    1860
cacagcccca accaggttcc caacacgtgt agcagtcatc agccattcct taacaatgaa    1920
tgtggtacct ggttagtgcc agccttggga aggagggagg gaggtaagag gggcttggtg    1980
atctctggag gaagagtgtt gcctttgctg tggttgggga atcgatcctt ggctatggcc    2040
tacccactcc cctggctgaa gagtgccaat cattacaaat cagcttcagc aaactgaaac    2100
aaaccttctg gtgccttggg cttgggggcc ctctgttttc ctgctcccag tctgcctgcc    2160
atacgttaga caacagaagc tgctgggctg ggcaggagcc ctgagctgcc tggtggattg    2220
gtaccaagtg gggccagcca gggcttctac tgactcgctg tgcaaccttg agcaagcccc    2280
actaggaacg gctagatcag caatgcccca aattgttgaa tcgtggtgat cacatttgga    2340
tggacaagtt aggaaactta gctgattctc tgagatactt cccacttcct catacattct    2400
acaatgagat gcctctcttc atgggcctgg ggaaaggatg aatgagtgtg gctggacttt    2460
tgacctttaa tgtccctgag cagttcttgg cccttgggga aagtagggg gaggatctgg     2520 ctgactcagc cccaaccgag gggtagcagc tgcagcccag ccaagcagaa caccctggcc    2580
ctacagacct gtgtctgagc aggctttgga ggaaaggcca cttctgagtc ctctgtctca    2640
ggagaagcca ggcctaggtg cttgacctgg tgatctgagc tgtgttttgtc ctagtatggg    2700 tggcagtcac ctctgaacac actggccttg gcttagagga ggcttgtgac ttcagctgtt    2760
```

```
ccagctgggg ctggatgctg gactctgatt ccctcagaga dacagaagat cgggcagagg   2820
tcaaccagaa ggccacacag ggcagtggac aacagtggag ggtataccaa atagaaataa   2880
aacgcaggaa acctctctga atactgccct tggggacctc aggagggagt gggactgatt   2940
ggagacaaag agccagaaat catcccctgg agatactcag acactgtatt gttattggcg   3000
ctgtcctgtg agggcagtgt ccaggctgcc ctgcttgtca tatccatgcc ctggctctgg   3060
ccccggtgag cacttgtgct gcatgaggaa aggaggatca ggtgggtca aaaccaaagc    3120 atcgaggctg gcactggcca agacagactc tggcagggag gggagtggaa ggaaggagcc   3180
ccaaacctgg agtgagacct ttgactttct gatgatgtgg ccaagaacta ggagtcacct   3240
ggccagcaca gccaagagtg gggctggggg cgccagcttt aaggtgtcaa cacctggccc   3300
ttgcggggaa agagccttca gcagccccca cggcctggag cctgggttta ttggagggtg   3360 cttctcttacc ctctgaaccc agtggaggag ggggcaatgg gatattcctg ctctgtatgg  3420
cctctgggtc agcttttgt tgcaaaatcc tatccccgc tgctagattc tttgaagcaa     3480
gggagaagca atagcccagc ctcagaatga ttctcaggaa agcaattcca ctgccagtgg   3540
actgggtgcc aggaggccta ggtctggatc tggggctgcc actaatgaca ggaaagtggg   3600
cttatcctca acctttctga gcctcagtgt cattatctgt aaaatgggga tgataatacc   3660
aggtagagtt gctctgatga ctggagacca tggagcggag tgtttgggaa atggcaaaga   3720
tttgtgaggg cttcgtgctt tagagatttg ctacccttaa ccaccagcat cagctcacct   3780
gggaatctgt aagaaatgca gagtcctagg ccccacccca gatctcctga ttttaacaac   3840
attcccaggt gacttggatg catgttaaag ttggagaagc tgccctaagt gacaacccttt  3900 tgccttttca ggactttgcc tctttccaca gagctgcagg ttctgtctag ctgcttttta    3960
ctgccatggg ggctgcctgg tccctgagta agcagtgggt agccctggat ggctgagggg    4020
ctggggaagc cagctgggcc agaccaggaa ggagcctgag gcacagcacc aaggcatggg    4080
gtagggtggg ctttgaggca cggcctcccc atgcccagac ccaggcccaa acaggaggct    4140
cctgtgcacc agcaagtgca gcaaagctgg ctgcagtgac aaggaagtca gagggagggc    4200
tggtttgcct caaccctcgc cctggatgtg gcaaaagata ccacaccgaa ggaagctgta    4260
ggggatctgg gacttagtca ggctagctaa gggcactgag tgattacagg caaggccac     4320 agagcggcag gaagttgtaa gtgcaggggc caggcacagt ctgagtggag agccatgatg    4380
gcactcatcc ctggctggct cctgggccca ggcctttgct cagaatacag tgcccaggcc    4440
cgcctgggca ttgccttaat tcctgtctga ggctgccttc cttcatcctc ctcaagctga    4500
ctgctatcag caggagaagg gaatgcagaa ccaccccccac cccaactcca gtgtctccag   4560
aactgagcag ggaccctccc catgacggag acagacaacc caatggcagg gcctggggga    4620
gttctaacct cccgtgccca agcctgactt ccttccctc tccagatact gaggaaagtg     4680
ggttggaggt gggccatgag ggtgggggac agggggaggg agagccattt cctaagaaga    4740
gcccaggttg tctcagccca gggagactgg tttcaggagc tgttccttca gaaaggacga    4800
tggaaatgga agtcacagca gggctgggga actgggggact ggttaggttg gacccatggg   4860
tgcagcaccc tccaaactgg tgtcagagcc tgcagatgag tcccgggagg agcggccctg    4920
caggaagcgg atgatcttct caatggtggc ctcctggtat tcgtgggacc acctgtgggc    4980
acaggagcca atgtggttca gacagctggg cagagggagc tgctagtcag ctgtttgccc    5040
acactctgcc tgtcatggtg atttgtaccc tacccccctg gtcccagggc cctggggctc    5100
```

-continued

```
acttgatacc gttgaaagta agcacagcct gcatgtcctc aggcaggacc tggggctcag    5160
gccactcgaa gccatcaatg atgggcacaa tgttcttgcc gcagcttaaa gcagtcacaa    5220
tctcctggag aaagaaagga aaggaggaag ataccctgt acccatctag ggacccttgt     5280
agccaggcag gtgctgggag gcccactggc ccgaggctgg gcccagggca ggacaccagt    5340
cctgatgtcc accttgatgt ctaccttaac ccttgtagtg taataaaaaa taaatatttt    5400
tcctttgccc agagttcctg gcacagagct gctaaaaccc ttggaatctc ttgagtgatg    5460
agtgtctttg tatgctaaag agatgattcc ccactggggg cccgggggggt gctatggggg   5520
tagcctagat agtttcagga agagggctgg tcaccaggga gaccagggca tgactagagg    5580
attggaactt tcagccccac ctcccagcct ccagagaggt gctggagatt gagttcaatc    5640
accaatggcc aatgatttaa tcaatcatgc ctacataatg gaacctccat aaaaaccccc    5700
aaacaagggg ttttgaagag cctccaggtt gataaacagg tgtaggtgct gggaaggtgg    5760
tagaaggcat ggcatccaca cctccaccct ccatacgtag agatcctatg tatctcttcc    5820
atttggctat tcttgagctg tgtcctttat aactgtgaaa ttaaataatt cagctgggca    5880
tggtgggtca cgcctgtaat cccaacactt tgggaggctg aggcaggagg atcacttgag    5940
cccaggattt tgagattaat aatattattt attactatta ttcaagcttt gttaaatcaa    6000
acctaaagct cttggaactt taagttattc tgagccttga caggaattgg tctctgcagc    6060
ctgagtcatg gggcatgcag ctgcaacttc cacctatttt tttttttttct gtaattactt   6120
aggaagacca aatggcacca gagataagac tcccttagat ccccacttag atcaccaccc    6180
tttctcaggg ggtaataaag tcatcttcct tggaatgtag caatctataa ccaatcaaag    6240
cactgtaaca tacgcactgg tcttgtatgg aaaatgttgt aatcctgcta aaattcctct    6300
ctctttgcct gtggaagtga aaccttaact tctccagttt ggaatgctca ccccatgcct    6360
ttggagtcaa tgcttactgg gtggctattc tcaaactttg cactcaaaga aactctatac    6420
ttagtcttat tttctgaatc tcattattta aggttgacat aataaacaac taatagtaag    6480
taaagtgaaa aaaaaaaaaa aaaaa                                          6505
```

<210> SEQ ID NO 2
<211> LENGTH: 459
<212> TYPE: PRT
<213> ORGANISM: Homo sapiens

<400> SEQUENCE: 2

```
Met Glu Gly Ser Ala Ser Pro Pro Glu Lys Pro Arg Ala Arg Pro Ala
1               5                   10                  15

Ala Ala Val Leu Cys Arg Gly Pro Val Glu Pro Leu Val Phe Leu Ala
                20                  25                  30

Asn Phe Ala Leu Val Leu Gln Gly Pro Leu Thr Thr Gln Tyr Leu Trp
            35                  40                  45

His Arg Phe Ser Ala Asp Leu Gly Tyr Asn Gly Thr Arg Gln Arg Gly
        50                  55                  60

Gly Cys Ser Asn Arg Ser Ala Asp Pro Thr Met Gln Glu Val Glu Thr
65                  70                  75                  80

Leu Thr Ser His Trp Thr Leu Tyr Met Asn Val Gly Gly Phe Leu Val
                85                  90                  95

Gly Leu Phe Ser Ser Thr Leu Leu Gly Ala Trp Ser Asp Ser Val Gly
                100                 105                 110

Arg Arg Pro Leu Leu Val Leu Ala Ser Leu Gly Leu Leu Leu Gln Ala
            115                 120                 125
```

```
Leu Val Ser Val Phe Val Gln Leu Gln Leu His Val Gly Tyr Phe
    130                 135                 140

Val Leu Gly Arg Ile Leu Cys Ala Leu Leu Gly Asp Phe Gly Gly Leu
145                 150                 155                 160

Leu Ala Ala Ser Phe Ala Ser Val Ala Asp Val Ser Ser Ser Arg Ser
                165                 170                 175

Arg Thr Phe Arg Met Ala Leu Leu Glu Ala Ser Ile Gly Val Ala Gly
                180                 185                 190

Met Leu Ala Ser Leu Leu Gly Gly His Trp Leu Arg Ala Gln Gly Tyr
                195                 200                 205

Ala Asn Pro Phe Trp Leu Ala Leu Ala Leu Leu Ile Ala Met Thr Leu
    210                 215                 220

Tyr Ala Ala Phe Cys Phe Gly Glu Thr Leu Lys Glu Pro Lys Ser Thr
225                 230                 235                 240

Arg Leu Phe Thr Phe Arg His His Arg Ser Ile Val Gln Leu Tyr Val
                245                 250                 255

Ala Pro Ala Pro Glu Lys Ser Arg Lys His Leu Ala Leu Tyr Ser Leu
                260                 265                 270

Ala Ile Phe Val Val Ile Thr Val His Phe Gly Ala Gln Asp Ile Leu
            275                 280                 285

Thr Leu Tyr Glu Leu Ser Thr Pro Leu Cys Trp Asp Ser Lys Leu Ile
    290                 295                 300

Gly Tyr Gly Ser Ala Ala Gln His Leu Pro Tyr Leu Thr Ser Leu Leu
305                 310                 315                 320

Ala Leu Lys Leu Leu Gln Tyr Cys Leu Ala Asp Ala Trp Val Ala Glu
                325                 330                 335

Ile Gly Leu Ala Phe Asn Ile Leu Gly Met Val Val Phe Ala Phe Ala
                340                 345                 350

Thr Ile Thr Pro Leu Met Phe Thr Gly Tyr Gly Leu Leu Phe Leu Ser
                355                 360                 365

Leu Val Ile Thr Pro Val Ile Arg Ala Lys Leu Ser Lys Leu Val Arg
    370                 375                 380

Glu Thr Glu Gln Gly Ala Leu Phe Ser Ala Val Ala Cys Val Asn Ser
385                 390                 395                 400

Leu Ala Met Leu Thr Ala Ser Gly Ile Phe Asn Ser Leu Tyr Pro Ala
                405                 410                 415

Thr Leu Asn Phe Met Lys Gly Phe Pro Phe Leu Leu Gly Ala Gly Leu
                420                 425                 430

Leu Leu Ile Pro Ala Val Leu Ile Gly Met Leu Glu Lys Ala Asp Pro
    435                 440                 445

His Leu Glu Phe Gln Gln Phe Pro Gln Ser Pro
    450                 455

<210> SEQ ID NO 3
<211> LENGTH: 2018
<212> TYPE: DNA
<213> ORGANISM: Homo sapiens

<400> SEQUENCE: 3
gccccacgcc acgcgtcgct ggtcccaggc agcgagtcgc tcgcgcgccc cgccgcccgc      60
ctggcgacag ctccgccgcg cacgcacatg gaggggagcg cgagcccccc ggaaaagccc     120
cgcgcccgcc ctgcggctgc cgtgctgtgc cggggcccgg tagagccgct ggtcttcctg     180
gccaactttg ccttggtcct gcagggcccg ctcaccacgc agtatctgtg gcaccgcttc     240
```

-continued

```
agcgccgacc tcggctacaa tggcacccgc caaagggggg gctgcagcaa ccgcagcgcg    300
gaccccacca tgcaggaagt ggagacccct acctcccact ggaccctcta catgaacgtg    360
ggcggcttcc tggtggggct cttctcgtcc accctgctgg agcttggag cgacagtgtg     420 ggccgccgcc cgctgctagt gctggcctcg ctgggcctgc tgctccaggc cctagtgtcc    480
gtttttgtgg tgcagctgca gctccacgtc ggctacttcg tgctgggtcg catcctttgt    540
gccctcctcg gcgacttcgg tggccttctg gctgctagct ttgcgtccgt ggcagatgtc    600
agctccagtc gcagccgcac cttccggatg gccctgctgg aagccagcat cggggtggct    660
gggatgctgg caagcctcct cgggggccac tggctccggg cccagggtta tgccaacccc    720
ttctggctgg ccttggcctt gctgatagcc atgactctct atgcagcttt ctgctttggt    780
gagaccttaa aggagccaaa gtccacccgg ctcttcacgt tccgtcacca ccgatccatt    840
gtccagctct atgtggctcc cgccccagag aagtccagga acatttagc cctctactca    900 ctggccatct tcgtggtgat cactgtgcac tttggggccc aggacatctt aacccttat    960 gaactaagca caccctctg ctgggactcc aaactaatcg ctatggttc tgcagctcag    1020 catctcccct acctcaccag cctgctggcc ctgaagctcc tgcagtactg cctggccgat    1080
gcctgggtag ctgagatcgg cctggccttc aacatcctgg ggatggtggt cttttgccttt    1140 gccactatca cgcctctcat gttcacaggt gctctctttt ctgctgtggc ctgtgtgaat    1200
agcctggcca tgctgacggc ctccggcatc ttcaactcac tctacccagc cactctgaac    1260
tttatgaagg ggttcccctt cctcctggga gctggcctcc tgctcatccc ggctgttctg    1320
attgggatgc tggaaaaggc tgatcctcac ctcgagttcc agcagtttcc ccagagcccc    1380
tgatctgcct ggaccagaag acagagggca agaggagcaa agtgaacacc aagcaactgg    1440
aggtctgcag ctggaagccc agcccacagc aggacaagca actcttgtct aagggcagtg    1500
ctctctttgg acgaggtagt caagagagac caaggcacca ccccatccac agctgaccca    1560
gcctctgtct aggatctaga atcataaccc acacaggccc actgcaggac aggtggcaga    1620
ggagctattt gggacaggag tcagttctcc ctttctgcta tccatcactt ataaccccac    1680
aggccagagg agaggtcctg agagaggtga cacttcaggg accagaggca gcacgagggc    1740
tggcatctct ccttccagcc caaactgcac agccccaacc aggttcccaa cacgtgtagc    1800
agtcatcagc cattccttaa caatgaatgt ggtacctggt tagtgccagc cttgggaagg    1860
agggagggag gtaagagggg cttggtgatc tctggaggaa gagtgttgcc tttgctgtgg    1920
ttggggaatc gatccttggc tatggcctac ccactcccct ggctgaagag tgccaatcat    1980
tacaaatcag cttcagcaaa ctgaaaaaaa aaaaaaaa                            2018
```

<210> SEQ ID NO 4
<211> LENGTH: 431
<212> TYPE: PRT
<213> ORGANISM: Homo sapiens

<400> SEQUENCE: 4

Met Glu Gly Ser Ala Ser Pro Pro Glu Lys Pro Arg Ala Arg Pro Ala
1               5                   10                  15

Ala Ala Val Leu Cys Arg Gly Pro Val Glu Pro Leu Val Phe Leu Ala
                20                  25                  30

Asn Phe Ala Leu Val Leu Gln Gly Pro Leu Thr Thr Gln Tyr Leu Trp
            35                  40                  45

His Arg Phe Ser Ala Asp Leu Gly Tyr Asn Gly Thr Arg Gln Arg Gly

|  |  |  | 50 |  |  |  | 55 |  |  |  | 60 |  |  |  |
|---|---|---|---|---|---|---|---|---|---|---|---|---|---|---|

Gly Cys Ser Asn Arg Ser Ala Asp Pro Thr Met Gln Glu Val Glu Thr
65                  70                  75                  80

Leu Thr Ser His Trp Thr Leu Tyr Met Asn Val Gly Gly Phe Leu Val
                85                  90                  95

Gly Leu Phe Ser Ser Thr Leu Leu Gly Ala Trp Ser Asp Ser Val Gly
            100                 105                 110

Arg Arg Pro Leu Leu Val Leu Ala Ser Leu Gly Leu Leu Leu Gln Ala
            115                 120                 125

Leu Val Ser Val Phe Val Gln Leu Gln Leu His Val Gly Tyr Phe
130                 135                 140

Val Leu Gly Arg Ile Leu Cys Ala Leu Leu Gly Asp Phe Gly Gly Leu
145                 150                 155                 160

Leu Ala Ala Ser Phe Ala Ser Val Ala Asp Val Ser Ser Ser Arg Ser
                165                 170                 175

Arg Thr Phe Arg Met Ala Leu Leu Glu Ala Ser Ile Gly Val Ala Gly
            180                 185                 190

Met Leu Ala Ser Leu Leu Gly Gly His Trp Leu Arg Ala Gln Gly Tyr
            195                 200                 205

Ala Asn Pro Phe Trp Leu Ala Leu Ala Leu Leu Ile Ala Met Thr Leu
210                 215                 220

Tyr Ala Ala Phe Cys Phe Gly Glu Thr Leu Lys Glu Pro Lys Ser Thr
225                 230                 235                 240

Arg Leu Phe Thr Phe Arg His His Arg Ser Ile Val Gln Leu Tyr Val
                245                 250                 255

Ala Pro Ala Pro Glu Lys Ser Arg Lys His Leu Ala Leu Tyr Ser Leu
            260                 265                 270

Ala Ile Phe Val Val Ile Thr Val His Phe Gly Ala Gln Asp Ile Leu
            275                 280                 285

Thr Leu Tyr Glu Leu Ser Thr Pro Leu Cys Trp Asp Ser Lys Leu Ile
            290                 295                 300

Gly Tyr Gly Ser Ala Ala Gln His Leu Pro Tyr Leu Thr Ser Leu Leu
305                 310                 315                 320

Ala Leu Lys Leu Leu Gln Tyr Cys Leu Ala Asp Ala Trp Val Ala Glu
                325                 330                 335

Ile Gly Leu Ala Phe Asn Ile Leu Gly Met Val Val Phe Ala Phe Ala
            340                 345                 350

Thr Ile Thr Pro Leu Met Phe Thr Gly Ala Leu Phe Ser Ala Val Ala
            355                 360                 365

Cys Val Asn Ser Leu Ala Met Leu Thr Ala Ser Gly Ile Phe Asn Ser
370                 375                 380

Leu Tyr Pro Ala Thr Leu Asn Phe Met Lys Gly Phe Pro Phe Leu Leu
385                 390                 395                 400

Gly Ala Gly Leu Leu Leu Ile Pro Ala Val Leu Ile Gly Met Leu Glu
                405                 410                 415

Lys Ala Asp Pro His Leu Glu Phe Gln Gln Phe Pro Gln Ser Pro
            420                 425                 430

<210> SEQ ID NO 5
<211> LENGTH: 459
<212> TYPE: PRT
<213> ORGANISM: mouse

<400> SEQUENCE: 5

```
Met Glu Gly Arg Val Ser Ser Val Gly Ser Pro His Ser Phe Leu Asn
1               5                   10                  15

Ala Pro Val Leu Phe Arg Gly Pro Val Glu Pro Leu Val Phe Leu Ala
            20                  25                  30

Asn Phe Ala Leu Val Leu Gln Gly Pro Leu Thr Thr Gln Tyr Leu Trp
        35                  40                  45

His Arg Phe Ser Thr Glu Leu Gly Tyr Asn Gly Thr Arg His Arg Glu
    50                  55                  60

Asn Cys Gly Asn Gln Ser Ala Asp Pro Leu Met Lys Glu Val Glu Thr
65                  70                  75                  80

Leu Thr Ser His Trp Thr Leu Tyr Met Asn Val Gly Gly Phe Leu Val
                85                  90                  95

Gly Leu Phe Trp Ser Thr Leu Leu Gly Ala Trp Ser Asp Arg Val Gly
            100                 105                 110

Arg Arg Pro Leu Leu Val Leu Ala Ser Leu Gly Leu Leu Leu Gln Ala
        115                 120                 125

Val Val Ser Ile Phe Val Val Gln Leu Glu Leu His Val Gly Phe Phe
    130                 135                 140

Val Leu Gly Arg Ala Leu Cys Ala Leu Leu Gly Asp Phe Asn Gly Leu
145                 150                 155                 160

Leu Ala Ala Ser Phe Ala Ser Val Ala Asp Val Ser Ser Asn His Ser
                165                 170                 175

Arg Thr Phe Arg Met Ala Leu Leu Glu Ala Cys Ile Gly Val Ala Gly
            180                 185                 190

Thr Leu Ala Ser Leu Leu Gly Gly His Trp Leu Arg Ala Gln Gly Tyr
        195                 200                 205

Ala Asn Pro Phe Trp Leu Ala Leu Ala Leu Leu Ile Val Met Ala Leu
    210                 215                 220

Tyr Ala Ala Phe Cys Phe Gly Glu Thr Val Lys Glu Pro Lys Ser Thr
225                 230                 235                 240

Arg Leu Phe Thr Leu Arg His His Arg Ser Ile Ala Arg Leu Tyr Val
                245                 250                 255

Val Pro Ala Pro Glu Lys Ser Arg Met His Leu Ala Leu Tyr Ser Leu
            260                 265                 270

Ala Ile Phe Val Val Val Thr Val His Phe Gly Ala Gln Asp Ile Leu
        275                 280                 285

Thr Leu Tyr Glu Leu Ser Ala Pro Leu Cys Trp Asp Ser Lys Leu Ile
    290                 295                 300

Gly Tyr Gly Ser Ala Ala Gln His Leu Pro Tyr Leu Thr Ser Leu Leu
305                 310                 315                 320

Gly Leu Arg Leu Leu Gln Phe Cys Leu Ala Asp Thr Trp Val Ala Glu
                325                 330                 335

Ile Gly Leu Ala Phe Asn Ile Leu Gly Met Val Val Phe Ala Phe Ala
            340                 345                 350

Thr Ile Thr Pro Leu Met Phe Thr Gly Tyr Gly Leu Leu Phe Leu Ser
        355                 360                 365

Leu Val Thr Thr Pro Val Ile Arg Ala Lys Leu Ser Lys Leu Val Ser
    370                 375                 380

Glu Ser Glu Gln Gly Ala Leu Phe Ser Ala Val Ala Cys Val Asn Ser
385                 390                 395                 400

Leu Val Met Leu Met Ala Ser Gly Ile Phe Asn Ser Ile Tyr Pro Ala
                405                 410                 415

Thr Leu Asn Phe Met Lys Gly Phe Pro Phe Leu Leu Gly Ala Gly Leu
```

```
                420              425              430
Leu Phe Ile Pro Ala Ile Leu Ile Gly Val Leu Glu Lys Val Asn Pro
    435                  440                  445

His Pro Glu Phe Gln Gln Phe Pro Gln Ser Pro
    450                  455

<210> SEQ ID NO 6
<211> LENGTH: 11171
<212> TYPE: DNA
<213> ORGANISM: Homo sapiens

<400> SEQUENCE: 6
```

| | | | | | |
|---|---|---|---|---|---|
| acctctaccc | tagtgggtac | tgcaggctct | ggctctggga | tgagccacac | cctgtcccat | 60 |
| tcctgatgag | ggaccttggc | ctctcctagc | cttagttctt | tatctaagaa | ataattccaa | 120 |
| ggatttagcc | aagtacccct | ccctcactgc | agctgaccta | actgggccaa | gcttttgtgt | 180 |
| aagtggtagg | gaggagttgg | aaggggaggg | aggagagtgg | agccaatcca | gaggcttgaa | 240 |
| tgtttaatgt | ggaatttcct | ctctctaggg | gaccacaggt | gggggcagct | gcaggggga | 300 |
| ggttattcag | ttcactagta | tctagccagc | acctacccat | cctgagtctc | ggactcctgg | 360 |
| ctcaggggag | gtggggtagc | taacaagctc | caacaggccc | aggcacagtc | acagtggcca | 420 |
| gaattggagc | catccatcct | cccaagaatc | aggcctgtca | ggacctgcct | ccagaaaccc | 480 |
| actcagctgc | tctgttctca | gggaaggtgg | cctttcctga | ttctgctccc | cctacctcca | 540 |
| gccctgaat | tagcacccctt | ggagttcaaa | actattttcc | acggttggaa | ttttgtatca | 600 |
| attagtagga | ttctttgact | attttttcctc | tcccaccatt | ctagaaacta | acgggcctgg | 660 |
| tgagggcttt | gtctatttcc | tttcctgttg | tggtcccgga | gtcccccagc | acagtgcctg | 720 |
| gcacgtaagg | ggcactcagt | aaatgagctg | aatgaatgaa | agataggga | gtaaggaagg | 780 |
| taatgctgtt | cctttttaca | ggcaataaaa | cagaggccca | gacagggtct | gacctcctca | 840 |
| gcagcagagc | aggtgactgc | cttctggcct | aattcctata | atgggagcca | cccaggagca | 900 |
| taggttcaca | cccaaggacc | tcccaggccc | tccccatct | tctctaaggg | aactgcagag | 960 |
| ccaggccctg | cctgacccca | gaaacaagac | tagtttccca | ggaaaagatc | ctagggcagg | 1020 |
| agtggagcaa | gtgacagctt | gttttttatt | ttattttat | tttatatttt | ttgagacagg | 1080 |
| gtcttgctct | gtcacccagg | ctggagtgca | gtggtgcgat | ctcagcccac | tgcaacctct | 1140 |
| gcctcctggg | ctcaattgat | cctcccacct | cagccacccg | agtacctggg | actacaggta | 1200 |
| tctgctacta | cgcctggcta | attttgtgt | atttttgta | gagacagggt | tttaccatgt | 1260 |
| tgcccagatt | ggtctcgaac | tcctgggttc | aagcgatcca | tgcgcctcag | cctccaaaag | 1320 |
| tgctgggatt | acaggtgtga | gccaccactc | ccagacgtga | cagcctgtta | atagcaataa | 1380 |
| tagcactttg | aatataccag | acactgcttt | tccacaactt | tttgagacat | gttttgttag | 1440 |
| caactccatt | ttacagatga | aaaaacagag | gctcagggtg | gtaagtggca | tgccgaaggt | 1500 |
| agtggcagag | cctaggtgtt | ccagcccagg | cagctgggct | cagcccactc | cgatcctctc | 1560 |
| cagctgcctc | tctgttacag | cgcagaacat | cagcagcatc | aggagtcatg | tgctcttcca | 1620 |
| gctctgcctt | gagtacccga | tgacctcgtt | tcctcagcgg | tagatagcga | tggttaatat | 1680 |
| tggctagcct | gtagagttat | cgggagacca | acgcacaaaa | agggtttaat | accgtgccca | 1740 |
| gcacatagta | agtggtcaat | acatgttaat | tgttgatatt | cttgttatct | gtggtgtgtc | 1800 |
| tgggccggga | gggagggctg | cagggcggtg | tctacgcaca | ctttacaggt | gaggtcatcc | 1860 |
| cgcgggctgg | gggtgccggg | cccctcgctg | gcccacgccc | agccaggtgc | accgcggcg | 1920 |

```
agagtccggt ggcctcaggt cacaggcccc tccccgccgg acatttaagg agggacgccg    1980
ggcgcaggcg cagacagcgc aagccccacg ccacgcgtcg ctggtcccag gcagcgagtc    2040
gctcgcgcgc cccgccgccc gcctggcgac agctccgccg cgcacgcaca tggaggggag    2100
cgcgagcccc ccggaaaagc cccgcgcccg ccctgcggct gccgtgctgt gccggggccc    2160
ggtagagccg ctggtcttcc tggccaactt tgccttggtc ctgcagggcc cgctcaccac    2220
gcagtatctg tggcaccgct tcagcgccga cctcggctac aatggcaccc gccaaagggg    2280
gggctgcagc aaccgcagcg cggaccccac catgcaggta gcgggcggc gaggagcctg    2340
gcaggtggag ggcctggtc tggagcgtgg gggcagcgga ggggcgggc ctgcgtaatg    2400
gtagtggcgg gtaactggag ggagggtgca ttttggatgg tgggcgggac cagagcaaag    2460
gggcctgacc gagaacctca gcgggtggga tgcgaaaagc tgagctaaag tctggccttg    2520
caggttaaca aaagggggg gaaaggaaag ggaatggggc cttggtccat gtccttcccc    2580
ctctccactg gcagattttg aaagctgtgc taagattctc tgaggtttag ggctccaaag    2640
gaagtcctca tccctgtagc tcccgggatg gcgaggattt ggggattgtg aacccagag    2700
tgaggaaccg caccctggtc attgtgcccc tacaggaagt ggagacccctt acctcccact    2760
ggaccctcta catgaacgtg ggcggcttcc tggtgggggct cttctcgtcc acctgctgg    2820
gagcttggag cgacagtgtg ggccgccgcc cgctgctagt gctggcctcg ctgggcctgc    2880
tgctccaggc cctagtgtcc gttttttgtgg tgcagctgca gctccacgtc ggctacttcg    2940
tgctgggtcg catcctttgt gccctcctcg gcgacttcgg tggccttctg gctgctagct    3000
ttgcgtccgt ggcagatgtc agctccagtc gcagccgcac cttccggatg gccctgctgg    3060
aagccagcat cggggtggct gggatgctgg caagcctcct cggggggccac tggctccggg    3120
cccagggtta tgccaacccc ttctggctgg ccttggcctt gctgatagcc atgactctct    3180
atgcagcttt ctgctttggt gagaccttaa aggagccaaa gtccacccgg ctcttcacgt    3240
tccgtcacca ccgatccatt gtccagctct atgtggctcc cgccccagag aagtccagga    3300
aacatttagc cctctactca ctggccatct tcgtggtgat cactgtgcac tttgggccc    3360
aggacatctt aaccctttat gaactaagca caccctctg ctgggactcc aaactaatcg    3420
gctatggttc tgcagctcag catctcccct acctcaccag cctgctggcc ctgaagctcc    3480
tgcagtactg cctggccgat gcctgggtag ctgagatcgg cctggccttc aacatcctgg    3540
ggatggtggt ctttgccttt gccactatca cgcctctcat gttcacaggt aaagtgtgtg    3600
ggctcaggga cagcttgtcc cagaggcact gggtaagaac tggggccgg ccactcactg    3660
cccccagatg tggttcattc ctgtgtcttt ggaaacatag ttatgccccc agcctgcact    3720
ggagaacaga caactaagaa atccctcaaa aatgccatct ttgatacatg gaaaatatag    3780
accttcagta gctaaagtaa ttaacccact gttatcaacc attaatattg ttagtaatat    3840
agagcaaaag acaaaagtgt ggctcataca ctaattgctt taccccttgg cctcccaccg    3900
cctattcata tgttcttaaa caaagtccat gccattaatg cctggtactc acttctctga    3960
taagaatcac aggacctacc tcaaatacCC ttagtcagct tctttgggtt ttttaaaaac    4020
cagtcttctc ggaccacaga tatgaaaattc ctgcttcagt tcctcttctc ctctttctcc    4080
ttctcctttc cctcctcact tcctcccctt cttttttga tgggagaggg tcaacaggcc    4140
agtaaatgag gaagttaact ttttaaaatt tttatttgat tgatgtattt agagacaggg    4200
tctcgctttg ttacccaggc tagagtgcag tggcacgatc atggctcact gcagcctcat    4260
```

```
cccccgggcc cagatgatcc tcccaccttg gcctctctag tagctgggac cactggtgca   4320
cattaccaca ccttgctaat ttttgtattt tttatagaga tggggtcctc accattttgc   4380
ccagtccagg tctctaactc ctgagctcaa ggatccgcct gcctcagcct cccaaagtgt   4440
tgggattaca ggcatgagcc accgtgcccg gctttagtta acttttttta aagggacaga   4500
tttattttga tagagcccta aaatgtgctg tgtatagtca acaatacaat aatcacagat   4560
ttcttaactc aactgcttgt ctgacaatta agcagaaggg aacctttccc tcctgctgat   4620
ggccctgggg gatgcagaga tgataaagat gctgtcattg ctctgggtcg gggggaggtc   4680
tcaacagagt gggatttgag gggcctgaca ctgctagggt ccctggatgc ctcatcgtat   4740
accttctttg gaggatccac tgtcctgtag gagtttgcag ttttgctgag gagtcagcag   4800
tcgcacaggg agagaaatgg ttatgaagaa acaggaagc ctgtaagtaa ctgaatgcaa   4860
agggaaaagg aactcccatt tgctgtgtcc ctatgccatg ctcttcatag atgttacctt   4920
tttacctcat gtattggttc cctgagattg ctgtaatgac ataccacaaa cttgggggct   4980
taacacaaca gaaacatatt ctctcacagt tctggaggcc agaagtccaa agtcagtacc   5040
accgggctga atggaagcag tcagcaggca gtgctccctt gcaagcctcc aggagagaac   5100
gtgtttctca tttcttccag cttctggggc tgctggcatt ccttggcttg ggcggccat   5160
caccagtctc tgcctctgtg ctcacattga ctctcctcct ctttgtgcct tctcaattct   5220
gtcggtgcca aatctccgtc tgctttcctc ttataaagat atgtgtgacg catttaggg   5280
cccaacctaa tccaggataa ctctgctctc tcaggaggct taactgcaca cctgcataga   5340
ctcatttцcc aaataaggta gtatttacag gttccagggc tatgaatctg atgccattgg   5400
gcaccattat tcagcctcct atgcctcaga accatcctgt gatgaaggcc ttattatctt   5460
cctcatacag ggagtcagga tcagagaggg taagtacccc aggccacaca gataatatgt   5520
aatggcatca ggttttgaac tcagggctga ctccaaagcc catgcttgtt ttctgtgccc   5580
tgccatatcc ctactaagtg ccaagtgggt gggtgatgcc tgctgtgacc acaagaggtt   5640
cagacaagaa agcaatcaat gggaattagc attcattcat gagagctagc aggtggccaa   5700
gcccagacaa gggcagtctc cattcctcct tgactactgt cttcccaccc tcaccatcaa   5760
ggaagttctt cctgggtcta acctaagccc cacatgggt atggatagga gctctgctgc   5820
ctttcccttg gacgcccctc tccccagccc cattttcctg atgagtgttt gtttctccac   5880
aggatatggg ttgcttttcc tgtcattagt catcacacct gtcatccggg ctaaactctc   5940
caagctggtg agagagacag agcagggtga gtgtcagaac ccacctgtgt ctggttcctc   6000
atgtccagtg ctgcccgaaa cgggctgatg ggcagccatg gctggggaa cagcttgcct   6060
tcccccctct caccctggag aagtaagtgg ccaaaacaaa cacatttctg tgaaattgcc   6120
cacaatgggc agaggatcat gccaccttgg attttcaaac cgcagagttg ggatttgcag   6180
tcagcagagc acaattatgt tctttctaga taaccagagc agaggattta ctctctgcag   6240
acctcagctt ttccgtctgt aagatgggtg tggtgatgcc agagttccct gtttctctgg   6300
ggtcagcgtg tacaagccca gaagtgaaca accttgtgac atgggtttca ttttccacag   6360
ttgacagata aagaaacaga gacccagggg gttacattgg ctcacccaag gttactcagt   6420
aaatggtgga gctaggatgc aaacctacgt ctgtgtttaa aagcagctgg tctcaggatc   6480
tgggttttag tccgagccct gccacaggcc tgtttcttca tctgtgatgt gggtggtttg   6540
cтттгтgatga catcacagac ccctctagat gtgacagaat ttaatctcaa cttctgttgg   6600
gttgttgcac aтттттgтaaa ctgtgggttc tcctggtata tctataaaga acagcttctc   6660
```

-continued

```
cagcctctgg gtctttatgc cccagtctgg aaacattcat cttttttccat ctgtcctgga    6720
atgaggatct gatgatgaca gagactctgg tgccatacag agcccactgt gggttctggt    6780
gtccccagaa tccatgtgtc ttcattcatt cacctaaact ttttttccca gcactttctc    6840
tgtgcccaga gatgtcaaga gaaacaggag aaaagaacag cccttactaa ctagctactt    6900
ccaggggacc aggcccagtg atgggtgatt tccatgtgaa cttaatgttg ctcacaatct    6960
aggaaatagg tattatcctt atttagcaga aggaggaaca ggaacccaaa ggataagaag    7020
ctattcagtg gtgacaccgc tatgaatatt ggaactgatc agaccagcag ttaatcccaa    7080
acaggagatg attccaaaga ggataaacca gaaaaaagcc atttccatca agctttcatc    7140
agacaatatc acatgtactt ttttttttct tttatgtgct gggttctgtc agatcacatg    7200
tacttttaat gtggatttaa tagcagccat ttgtttagta gcccctctgt gccagctact    7260
gtccacatat gaccttactg aatccttgtc acagtacatg atgtagcagg atttactggt    7320
gaggaagggg agacataggt taagtgacta ctcccggtca cacagctgtg aggtggtggt    7380
gccagagttg gaatatggcc ctttcggact ccagagtatg gtatttattt cttcacaggt    7440
gctctctttt ctgctgtggc ctgtgtgaat agcctggcca tgctgacggc ctccggcatc    7500
ttcaactcac tctacccagc cactctgaac tttatgaagg ggttcccctt cctcctggga    7560
gctggcctcc tgctcatccc ggctgttctg attgggtaat gcagggccct gaacccatgc    7620
tcataatgga gccctttctc ttaaaagttt cctcttctcc tcccaaccag aaatggcagc    7680
ttcattcctg gaatccttac cctctgggtg tcttgtccca ggttgcccct ctccttgcag    7740
atggctgcct aatcctccag gagccatttt ccaagggcga gatggcgagc taggtggagg    7800
aaggatcagg ctaacattgc tgcttggcaa ggctgtgttc tctatcccag ttcccctatt    7860
tccctccatt cccatttat agatggaact atggcagcag aactgtgtta aagggaaggc    7920
caggaagctt tgtcagctag ttgtggctgg gccacaggct agcttgaccc gctgactttt    7980
tcctgtatga tattaagaat tatatttcat ggccgggcgt ggaggctctt gcctgtaatc    8040
ccgatcctgt gggaggctga ggcaggagga ccacttgagc ccgggaattc aagatcagcc    8100
tgggcaacat agcaagacct tgtctgtata aaaaatttaa aaaatcaccc aggcatggtg    8160
gtatgcactg gtagtcccag ctactaagga ggctgaggca ggaggatcac ttgagcccag    8220
gagttcaagg gtacagtgag ctatgattat gtcactgccc tccagcctgg acaacagagc    8280
aagaccctgt ctcttaaaaa aaaaaaagtt attttccaga gccatgtccc tggatattgt    8340
cctccagctc tcagcttctc agcttgggga aggaggaggt tcaggagagc tacctggacc    8400
agcccacccc agtaaatcct gtgtcacttc tccagacagg ccttgagggt tccccacatg    8460
aaatccaaac tctctctctg gtctctcaca ggatgctgga aaaggctgat cctcacctcg    8520
agttccagca gtttccccag agccctgat ctgcctggac cagaagacag agggcaagag    8580
gagcaaagtg aacaccaagc aactggaggt ctgcagctgg aagcccagcc cacagcagga    8640
caagcaactc ttgtctaagg gcagtgctct ctttggacga ggtagtcaag agagaccaag    8700
gcaccacccc atccacagct gacccagcct ctgtctagga tctagaatca taacccacac    8760
aggcccactg caggacaggt ggcagaggag ctatttggga caggagtcag ttctcccttt    8820
ctgctatcca tcacttataa ccccacaggc cagaggagag gtcctgagag aggtgacact    8880
tcagggacca gaggcagcac gagggctgga atctctcctt ccagcccaaa ctgcacagcc    8940
ccaaccaggt tcccaacacg tgtagcagtc atcagccatt ccttaacaat gaatgtggta    9000
```

```
cctggttagt gccagccttg ggaaggaggg agggaggtaa gaggggcttg gtgatctctg    9060
gaggaagagt gttgcctttg ctgtggttgg ggaatcgatc cttggctatg gcctacccac    9120 tccctggct gaagagtgcc aatcattaca aatcagcttc agcaaactga aacaaacctt    9180
ctggtgcctt gggctttggg gccctctgtt ttcctgctcc cagtctgcct gccatacgtt    9240
agacaacaga agctgctggg ctgggcagga ccctgagct gcctggtgga ttggtaccaa    9300
gtggggccag ccagggcttc tactgactcg ctgtgcaacc ttgagcaagc cccactagga    9360
acggctagat cagcaatgcc ccaaattgtt gaatcgtggt gatcacattt ggatggacaa    9420
gttaggaaac ttagctgatt ctctgagata cttcccactt cctcatacat tctacagtga    9480
gatgcctctc ttcatgggcc tggggaaagg atgaatgagt gtggctggac ttttgacctt    9540
taatgtccct gagcagttct tggcccttgg ggagaagtag gggaggatc tggctgactc    9600 agccccaacc gaggggtagc agctgcagcc cagccaagca gaacaccctg gccctacaga    9660
cctgtgtctg agcaggcttt ggaggaaagg ccacttctga gtcctctgtc tcaggagaag    9720
ccaggcctag gtgcttgacc tggtgatctg agctgtgttt gtcctagtat gggtggcagt    9780
cacctctgaa cacactggcc ttggcttaga ggaggcttgt gacttcagct gttccagctg    9840
gggctggatg ctggactctg attccctcag agagacagaa gatcgggcag aggtcaacca    9900
gaaggccaca cagggcagtg gacaacagtg gagggtatac caaatagaaa taaaatgcag    9960
gaaacctctc tgaatactgc ccttggggac ctcaggaggg agtgggactg attggagaca    10020
aagagccaga aatcatcccc tggagatact cagacactgt attgttattg gcgctgtcct    10080
gtgagggcag tgtccaggct gccctgcttg tcatatccat gccctggctc tggccccggt    10140
gagcacttgt gctgcatgag gaaaggagga tcaggtgggg tcaaaaccaa agcatcgagg    10200
ctggcactgg ccaagacaga ctctggcagg gaggggagtg gaaggaagga gccccaaacc    10260
tggagtgaga cctttgactt tctgatgatg tggccaagaa ctaggagtca cctggccagc    10320
acagccaaga gtggggctgg gggcgcagcc agctttaagg tgtcaacacc tggcccttgc    10380
ggggaaagag ccttcagcag cccccacggc ctggagcctg ggtttattgg agggtgctttt   10440 cttaccctct gaacccagtg gaggagggg caatgggata ttcctgctct gtatggcctc    10500
tgggtcagct ttttgttgca aaatcctatc ccccgctgct agattctttg aagcaaggga    10560
gaagcaatag cccagcctca gaatgattct caggaaagca attccactgc cagtggactg    10620
ggtgccagga ggcctaggtc tggatctggg gctgccacta atgacaggaa agtgggctta    10680
tcctcaacct ttctgagcct cagtgtcatt atctgtaaaa tggggatgat aataccaggt    10740
agagttgctc tgatgactgg agaccatgga gcggagtgtt tgggaaatgg caaagatttg    10800
tgagggcttc gtgctttaga gatttgctac ccttaaccac cagcatcagc tcacctggga    10860
atctgtaaga aatgcagagt cctaggcccc accccagatc tcctgatttt aacaacattc    10920
ccaggtgact tggatgcatg ttaaagttgg agaagctgcc ctaagtgaca acccctttgcc   10980 ttttcaggac tttgcctctt tccacagagc tgcaggttct gtctaggctg cttttactgc    11040
catgggggct gcctggtccc tgagtaagca gtgggtagcc ctggatggct gagggctgg    11100 ggaagccagc tgggccagac caggaaggag cctgaggcac agcaccaagg catggggtag    11160
ggtgggcttt g                                                          11171

<210> SEQ ID NO 7
<211> LENGTH: 31
<212> TYPE: DNA
<213> ORGANISM: artificial sequence
```

```
<220> FEATURE:
<223> OTHER INFORMATION: forward primer for G21 open reading frame

<400> SEQUENCE: 7
tatagatctc accatggagg ggagcgcgag c                              31

<210> SEQ ID NO 8
<211> LENGTH: 29
<212> TYPE: DNA
<213> ORGANISM: artificial sequence
<220> FEATURE:
<223> OTHER INFORMATION: reverse primer for G21 open reading frame

<400> SEQUENCE: 8
tatagatctc aggggctctg gggaaactg                                 29

<210> SEQ ID NO 9
<211> LENGTH: 20
<212> TYPE: DNA
<213> ORGANISM: artificial sequence
<220> FEATURE:
<223> OTHER INFORMATION: forward primer for quantitative PCR of PCFT
      cDNA

<400> SEQUENCE: 9
atgcagcttt ctgctttggt                                           20

<210> SEQ ID NO 10
<211> LENGTH: 20
<212> TYPE: DNA
<213> ORGANISM: artificial sequence
<220> FEATURE:
<223> OTHER INFORMATION: reverse primer for quantitative PCR of PCFT
      cDNA

<400> SEQUENCE: 10
ggagccacat agagctggac                                           20

<210> SEQ ID NO 11
<211> LENGTH: 20
<212> TYPE: DNA
<213> ORGANISM: artificial sequence
<220> FEATURE:
<223> OTHER INFORMATION: forward primer for quantitative PCT of PCFT
      cDNA - pair 2

<400> SEQUENCE: 11
ctgtcatccg ggctaaactc                                           20

<210> SEQ ID NO 12
<211> LENGTH: 20
<212> TYPE: DNA
<213> ORGANISM: artificial sequence
<220> FEATURE:
<223> OTHER INFORMATION: reverse primer for quantitative PCT of PCFT
      cDNA - pair 2

<400> SEQUENCE: 12
aggccacagc agaaaagaga                                           20

<210> SEQ ID NO 13
<211> LENGTH: 20
<212> TYPE: DNA
<213> ORGANISM: artificial sequence
<220> FEATURE:
<223> OTHER INFORMATION: forward primer for quantitative PCT of G3PDH
      cDNA
```

```
<400> SEQUENCE: 13
cgaccacttt gtcaagctca                                                    20

<210> SEQ ID NO 14
<211> LENGTH: 20
<212> TYPE: DNA
<213> ORGANISM: artificial sequence
<220> FEATURE:
<223> OTHER INFORMATION: reverse primer for quantitative PCR of G3PDH
      cDNA

<400> SEQUENCE: 14
ccctgttgct gtagccaaat                                                    20

<210> SEQ ID NO 15
<211> LENGTH: 17
<212> TYPE: DNA
<213> ORGANISM: artificial sequence
<220> FEATURE:
<223> OTHER INFORMATION: forward primer for quantitative PCR of
      beta-actin cDNA

<400> SEQUENCE: 15
cgtgctgctg accgagc                                                       17

<210> SEQ ID NO 16
<211> LENGTH: 24
<212> TYPE: DNA
<213> ORGANISM: artificial sequence
<220> FEATURE:
<223> OTHER INFORMATION: reverse primer for quantitative PCT of
      beta-actin cDNA

<400> SEQUENCE: 16
gaaggtctca acatgatct gggt                                                24

<210> SEQ ID NO 17
<211> LENGTH: 27
<212> TYPE: DNA
<213> ORGANISM: artificial sequence
<220> FEATURE:
<223> OTHER INFORMATION: forward primer for PCR of exon 1 of the PCFT
      gene

<400> SEQUENCE: 17
tacgcacact ttacaggtga ggtcatc                                            27

<210> SEQ ID NO 18
<211> LENGTH: 26
<212> TYPE: DNA
<213> ORGANISM: artificial sequence
<220> FEATURE:
<223> OTHER INFORMATION: reverse primer for PCR of exon 1 of the PCFT
      gene

<400> SEQUENCE: 18
ccaaaatgca ccctccctcc agttac                                             26

<210> SEQ ID NO 19
<211> LENGTH: 26
<212> TYPE: DNA
<213> ORGANISM: artificial sequence
<220> FEATURE:
<223> OTHER INFORMATION: forward primer for PCR of exon 2 of the PCFT
      gene
```

```
<400> SEQUENCE: 19
ttctctgagg tttagggctc caaagg                                          26

<210> SEQ ID NO 20
<211> LENGTH: 26
<212> TYPE: DNA
<213> ORGANISM: artificial sequence
<220> FEATURE:
<223> OTHER INFORMATION: reverse primer for PCR of exon 2 of the PCFT
      gene

<400> SEQUENCE: 20
tagttgtctg ttctccagtg caggct                                          26

<210> SEQ ID NO 21
<211> LENGTH: 26
<212> TYPE: DNA
<213> ORGANISM: artificial sequence
<220> FEATURE:
<223> OTHER INFORMATION: forward primer for PCR of exon 3 of the PCFT
      gene

<400> SEQUENCE: 21
ttcctccttg actactgtct tcccac                                          26

<210> SEQ ID NO 22
<211> LENGTH: 26
<212> TYPE: DNA
<213> ORGANISM: artificial sequence
<220> FEATURE:
<223> OTHER INFORMATION: reverse primer for PCR of exon 3 of the PCFT
      gene

<400> SEQUENCE: 22
tctgctgact gcaaatccca actctg                                          26

<210> SEQ ID NO 23
<211> LENGTH: 26
<212> TYPE: DNA
<213> ORGANISM: artificial sequence
<220> FEATURE:
<223> OTHER INFORMATION: forward primer for PCR of exon 4 of the PCFT
      gene

<400> SEQUENCE: 23
tagcaggatt tactggtgag gaaggg                                          26

<210> SEQ ID NO 24
<211> LENGTH: 26
<212> TYPE: DNA
<213> ORGANISM: artificial sequence
<220> FEATURE:
<223> OTHER INFORMATION: reverse primer for PCR of exon 4 of the PCFT
      gene

<400> SEQUENCE: 24
tgccaagcag caatgttagc ctgatc                                          26

<210> SEQ ID NO 25
<211> LENGTH: 26
<212> TYPE: DNA
<213> ORGANISM: artificial sequence
<220> FEATURE:
<223> OTHER INFORMATION: forward primer for PCR of exon 5 of the PCFT
      gene

<400> SEQUENCE: 25
```

```
tattgtcctc cagctctcag cttctc                                          26

<210> SEQ ID NO 26
<211> LENGTH: 26
<212> TYPE: DNA
<213> ORGANISM: artificial sequence
<220> FEATURE:
<223> OTHER INFORMATION: reverse primer for PCR of exon 5 of the PCFT
      gene

<400> SEQUENCE: 26
aaggttgcac agcgagtcag tagaag                                          26

<210> SEQ ID NO 27
<211> LENGTH: 20
<212> TYPE: DNA
<213> ORGANISM: artificial sequence
<220> FEATURE:
<223> OTHER INFORMATION: forward primer for PCR of exon 3 of PCFT
      cDNA

<400> SEQUENCE: 27
cagctcagca tctcccctac                                                 20

<210> SEQ ID NO 28
<211> LENGTH: 24
<212> TYPE: DNA
<213> ORGANISM: artificial sequence
<220> FEATURE:
<223> OTHER INFORMATION: reverse primer for PCR of exon 3 of PCFT cDNA

<400> SEQUENCE: 28
aagagagcac tgcccttaga caag                                            24

<210> SEQ ID NO 29
<211> LENGTH: 20
<212> TYPE: DNA
<213> ORGANISM: artificial sequence
<220> FEATURE:
<223> OTHER INFORMATION: forward primer for PCR of full length open
      reading frame of PCFT cDNA

<400> SEQUENCE: 29
cgtcaccttc gtccctccg                                                  20

<210> SEQ ID NO 30
<211> LENGTH: 20
<212> TYPE: DNA
<213> ORGANISM: artificial sequence
<220> FEATURE:
<223> OTHER INFORMATION: reverse primer for PCR of full length open
      reading frame of PCFT cDNA

<400> SEQUENCE: 30
tagcaggata agcggaggcc                                                 20

<210> SEQ ID NO 31
<211> LENGTH: 1380
<212> TYPE: DNA
<213> ORGANISM: Homo sapiens

<400> SEQUENCE: 31
atggagggga gcgcgagccc cccggaaaag ccccgcgccc gccctgcggc tgccgtgctg      60
tgccggggcc cggtagagcc gctggtcttc ctggccaact ttgccttggt cctgcagggc     120
```

```
                                                -continued
ccgctcacca cgcagtatct gtggcaccgc ttcagcgccg acctcggcta caatggcacc      180
cgccaaaggg ggggctgcag caaccgcagc gcggacccca ccatgcagga agtggagacc      240
cttacctccc actggaccct ctacatgaac gtgggcggct tcctggtggg gctcttctcg      300
tccaccctgc tgggagcttg gagcgacagt gtgggccgcc gcccgctgct agtgctggcc      360
tcgctgggcc tgctgctcca ggccctagtg tccgttttg tggtgcagct gcagctccac       420
gtcggctact tcgtgctggg tcgcatcctt tgtgccctcc tcggcgactt cggtggcctt      480
ctggctgcta gctttgcgtc cgtggcagat gtcagctcca gtcgcagccg caccttccgg      540
atggccctgc tggaagccag catcggggtg gctgggatgc tggcaagcct cctcgggggc      600
cactggctcc gggcccaggg ttatgccaac cccttctggc tggccttggc cttgctgata      660
gccatgactc tctatgcagc tttctgcttt ggtgagacct aaaggagcc aaagtccacc       720 cggctcttca cgttccgtca ccaccgatcc attgtccagc tctatgtggc tcccgcccca     780
gagaagtcca ggaaacattt agccctctac tcactggcca tcttcgtggt gatcactgtg     840
cactttgggg cccaggacat cttaacccttc tatgaactaa gcacacccct ctgctgggac     900
tccaaactaa tcggctatgg ttctgcagct cagcatctcc cctacctcac cagcctgctg     960
gccctgaagc tcctgcagta ctgcctggcc gatgcctggg tagctgagat cggcctggcc    1020
ttcaacatcc tggggatggt ggtctttgcc tttgccacta tcacgcctct catgttcaca    1080
ggatatgggt tgcttttcct gtcattagtc atcacacctg tcatccgggc taaactctcc    1140
aagctggtga gagagacaga gcagggtgct ctcttttctg ctgtggcctg tgtgaatagc    1200
ctggccatgc tgacggcctc cggcatcttc aactcactct acccagccac tctgaacttt   1260
atgaaggggt tccccttcct cctgggagct ggcctcctgc tcatcccggc tgttctgatt    1320
gggatgctgg aaaaggctga tcctcacctc gagttccagc agtttcccca gagcccctga   1380
```